United States Patent
Hyde et al.

(10) Patent No.: US 10,402,927 B2
(45) Date of Patent: Sep. 3, 2019

(54) EVIDENCE-BASED HEALTHCARE INFORMATION MANAGEMENT PROTOCOLS

(75) Inventors: Roderick A. Hyde, Redmond, WA (US); Edward K. Y. Jung, Bellevue, WA (US); Jordin T. Kare, Seattle, WA (US); Eric C. Leuthardt, St Louis, MO (US); Royce A. Levien, Lexington, MA (US); Richard T. Lord, Tacoma, WA (US); Robert W. Lord, Seattle, WA (US); Mark A. Malamud, Seattle, WA (US); John D. Rinaldo, Jr., Bellevue, WA (US); Dennis J. Rivet, Chesapeake, VA (US); Clarence T. Tegreene, Bellevue, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 692 days.

(21) Appl. No.: 13/374,748

(22) Filed: Jan. 9, 2012

(65) Prior Publication Data
US 2013/0173297 A1 Jul. 4, 2013

Related U.S. Application Data

(63) Continuation-in-part of application No. 13/374,750, filed on Jan. 9, 2012, which is a continuation-in-part of application No. 13/374,744, filed on Jan. 9, 2012, now abandoned, which is a continuation-in-part of application No. 13/374,747, filed on Jan. 9, 2012, (Continued)

(51) Int. Cl.
*G16H 40/60* (2018.01)
*G06Q 50/24* (2012.01)
*G06Q 10/10* (2012.01)
*G06Q 50/18* (2012.01)
*G16H 10/60* (2018.01)

(52) U.S. Cl.
CPC ............ *G06Q 50/24* (2013.01); *G06Q 10/10* (2013.01); *G06Q 50/18* (2013.01); *G16H 10/60* (2018.01)

(58) Field of Classification Search
CPC .................. G06Q 50/22; G06Q 50/24; G06F 19/322–327; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00
See application file for complete search history.

(56) References Cited

U.S. PATENT DOCUMENTS 3,843,841 A 10/1974 Rubinstein
5,537,314 A 7/1996 Kanter
(Continued)

OTHER PUBLICATIONS

U.S. Appl. No. 13/199,053, Hyde et al.
(Continued)

*Primary Examiner* — John A Pauls

(57) ABSTRACT

Structures and protocols are presented for signaling a decision (processing or transmitting a medical record or other resource, e.g.) conditionally, at least partly based on one or more performance indicia (excess hospital readmissions, e.g.) or therapeutic determinants (prior success, e.g.) or privacy considerations (patient consent, e.g.).

29 Claims, 21 Drawing Sheets

Related U.S. Application Data which is a continuation-in-part of application No. 13/374,745, filed on Jan. 9, 2012, which is a continuation-in-part of application No. 13/374,519, filed on Dec. 30, 2011.

(56) References Cited

U.S. PATENT DOCUMENTS

| | | |
|---|---|---|
| 5,612,869 A | 3/1997 | Letzt et al. |
| 5,724,025 A | 3/1998 | Tavori |
| 5,902,234 A | 5/1999 | Webb |
| 5,945,651 A | 8/1999 | Chorosinski et al. |
| 5,954,641 A | 9/1999 | Kehr et al. |
| 5,991,429 A | 11/1999 | Coffin et al. |
| 6,000,828 A | 12/1999 | Leet |
| 6,014,626 A | 1/2000 | Cohen |
| 6,038,333 A | 3/2000 | Wang |
| 6,094,573 A | 7/2000 | Heinonen et al. |
| 6,108,709 A | 8/2000 | Shinomura et al. |
| 6,111,946 A | 8/2000 | O'Brien |
| 6,112,074 A | 8/2000 | Pinder |
| 6,122,485 A | 9/2000 | Archer |
| 6,124,136 A | 9/2000 | Kell |
| 6,134,014 A | 10/2000 | Tzu et al. |
| 6,137,914 A | 10/2000 | Ligtenberg et al. |
| 6,161,095 A | 12/2000 | Brown |
| 6,167,398 A | 12/2000 | Wyard et al. |
| 6,185,573 B1 | 2/2001 | Angelucci et al. |
| 6,198,383 B1 | 3/2001 | Sekura et al. |
| 6,198,695 B1 | 3/2001 | Kirton et al. |
| 6,205,326 B1 | 3/2001 | Tell et al. |
| 6,211,791 B1 | 4/2001 | Ponce de Leon et al. |
| 6,266,645 B1 | 7/2001 | Simpson |
| 6,307,937 B1 | 10/2001 | Dillon et al. |
| 6,310,554 B1 | 10/2001 | Carrell |
| 6,310,556 B1 | 10/2001 | Green et al. |
| 6,336,048 B1 | 1/2002 | Bonnet |
| 6,338,039 B1 | 1/2002 | Lonski et al. |
| 6,366,809 B1 | 4/2002 | Olson et al. |
| 6,371,931 B1 | 4/2002 | Guillen |
| 6,373,392 B1 | 4/2002 | Au |
| 6,375,038 B1 | 4/2002 | Daansen et al. |
| 6,380,858 B1 | 4/2002 | Yarin et al. |
| 6,392,747 B1 | 5/2002 | Allen et al. |
| 6,397,181 B1 | 5/2002 | Li et al. |
| 6,400,304 B1 | 6/2002 | Chubbs, III |
| 6,405,165 B1 | 6/2002 | Blum et al. |
| 6,421,726 B1 | 7/2002 | Kenner et al. |
| 6,424,729 B1 | 7/2002 | Soon |
| 6,437,707 B1 | 8/2002 | Johnson |
| 6,442,485 B2 | 8/2002 | Evans |
| 6,452,487 B1 | 9/2002 | Krupinski |
| 6,473,824 B1 | 10/2002 | Kreissig et al. |
| 6,513,014 B1 | 1/2003 | Walker et al. |
| 6,514,200 B1 | 2/2003 | Khouri |
| 6,519,327 B1 | 2/2003 | Cannon et al. |
| 6,536,189 B1 | 3/2003 | Murray |
| 6,553,341 B1 | 4/2003 | Mullaly et al. |
| 6,561,811 B2 | 5/2003 | Rapoza et al. |
| 6,575,901 B2 | 6/2003 | Stoycos et al. |
| 6,594,519 B2 | 7/2003 | Stoycos et al. |
| 6,636,592 B2 | 10/2003 | Marchand et al. |
| 6,650,751 B1 | 11/2003 | Becker |
| 6,655,545 B1 | 12/2003 | Sonneborn |
| 6,655,583 B1 | 12/2003 | Walsh et al. |
| 6,656,122 B2 | 12/2003 | Davidson et al. |
| 6,665,558 B2 | 12/2003 | Kalgren et al. |
| 6,671,548 B1 | 12/2003 | Mouchawar et al. |
| 6,693,512 B1 | 2/2004 | Frecska et al. |
| 6,697,456 B2 | 2/2004 | Chan et al. |
| 6,699,124 B2 | 3/2004 | Suchocki |
| 6,700,604 B1 | 3/2004 | Murata et al. |
| 6,704,595 B2 | 3/2004 | Bardy |
| 6,721,921 B1 | 4/2004 | Altman |
| 6,726,634 B2 | 4/2004 | Freeman |
| 6,738,613 B1 | 5/2004 | Ogawa et al. |
| 6,739,508 B2 | 5/2004 | Ushioda et al. |
| 6,748,687 B2 | 6/2004 | Riley |
| 6,768,420 B2 | 7/2004 | McCarthy et al. |
| 6,790,668 B1 | 9/2004 | Ferreira et al. |
| 6,791,477 B2 | 9/2004 | Sari et al. |
| 6,799,165 B1 | 9/2004 | Boesjes |
| 6,807,532 B1 | 10/2004 | Kolls |
| 6,831,993 B2 | 12/2004 | Lemelson et al. |
| 6,832,245 B1 | 12/2004 | Isaacs et al. |
| 6,839,403 B1 | 1/2005 | Kotowski et al. |
| 6,882,278 B2 | 4/2005 | Winings et al. |
| 6,893,396 B2 | 5/2005 | Schulze et al. |
| 6,901,347 B1 | 5/2005 | Murray et al. |
| 6,920,699 B2 | 7/2005 | Reusing et al. |
| 6,926,667 B2 | 8/2005 | Khouri |
| 6,944,599 B1 | 9/2005 | Vogel et al. |
| 6,952,678 B2 | 10/2005 | Williams et al. |
| 6,957,076 B2 | 10/2005 | Hunzinger |
| 6,973,371 B1 | 12/2005 | Benouali |
| 6,978,177 B1 | 12/2005 | Chen et al. |
| 6,980,958 B1 | 12/2005 | Surwit et al. |
| 6,981,080 B2 | 12/2005 | Thompson et al. |
| 6,985,206 B2 | 1/2006 | Anderson et al. |
| 6,988,132 B2 | 1/2006 | Horvitz |
| 6,988,498 B2 | 1/2006 | Berthon-Jones et al. |
| 7,002,454 B1 | 2/2006 | Gustafson |
| 7,016,854 B2 | 3/2006 | Himes |
| 7,020,458 B2 | 3/2006 | Bossemeyer, Jr. et al. |
| 7,031,734 B2 | 4/2006 | Kim |
| 7,034,934 B2 | 4/2006 | Manning |
| 7,042,338 B1 | 5/2006 | Weber |
| 7,046,162 B2 | 5/2006 | Dunstan |
| 7,047,083 B2 | 5/2006 | Gunderson et al. |
| 7,054,688 B1 | 5/2006 | Uhrenius et al. |
| 7,062,073 B1 | 6/2006 | Tumey et al. |
| 7,068,992 B1 | 6/2006 | Massie et al. |
| 7,069,085 B2 | 6/2006 | Cao et al. |
| 7,076,235 B2 | 7/2006 | Esque et al. |
| 7,087,036 B2 | 8/2006 | Busby et al. |
| 7,092,566 B2 | 8/2006 | Krumm |
| 7,100,210 B2 | 8/2006 | Kuo et al. |
| 7,107,095 B2 | 9/2006 | Manolas |
| 7,114,954 B2 | 10/2006 | Eggert et al. |
| 7,119,814 B2 | 10/2006 | Meron et al. |
| 7,127,493 B1 | 10/2006 | Gautier |
| 7,132,238 B2 | 11/2006 | Danenberg |
| 7,163,151 B2 | 1/2007 | Kiiskinen |
| 7,170,823 B2 | 1/2007 | Fabricius et al. |
| 7,172,124 B2 | 2/2007 | Wang et al. |
| 7,177,684 B1 | 2/2007 | Kroll et al. |
| 7,181,192 B2 | 2/2007 | Panasik et al. |
| 7,181,375 B2 | 2/2007 | Rao et al. |
| 7,203,633 B2 | 4/2007 | Gabele et al. |
| 7,204,805 B2 | 4/2007 | Dean |
| 7,223,246 B2 | 5/2007 | Don |
| 7,233,745 B2 | 6/2007 | Loechner |
| 7,239,275 B2 | 7/2007 | Dybdal et al. |
| 7,242,462 B2 | 7/2007 | Huang |
| 7,246,619 B2 | 7/2007 | Truschel et al. |
| 7,257,158 B1 | 8/2007 | Figueredo et al. |
| 7,260,205 B1 | 8/2007 | Murphy et al. |
| 7,263,493 B1 | 8/2007 | Provost et al. |
| 7,269,787 B2 | 9/2007 | Amitay et al. |
| 7,271,728 B2 | 9/2007 | Taylor et al. |
| 7,272,571 B2 | 9/2007 | Tuttrup et al. |
| 7,283,566 B2 | 10/2007 | Siemens et al. |
| 7,283,807 B2 | 10/2007 | Bossemeyer, Jr. et al. |
| 7,286,894 B1 | 10/2007 | Grant et al. |
| 7,287,031 B1 | 10/2007 | Karpf et al. |
| 7,289,651 B2 | 10/2007 | Vining et al. |
| 7,293,645 B2 | 11/2007 | Harper et al. |
| 7,295,120 B2 | 11/2007 | Waldner et al. |
| 7,313,515 B2 | 12/2007 | Crouch et al. |
| 7,319,378 B1 | 1/2008 | Thompson et al. |
| 7,319,876 B2 | 1/2008 | Jha et al. |
| 7,330,101 B2 | 2/2008 | Sekura |
| 7,335,106 B2 | 2/2008 | Johnson |
| 7,345,574 B2 | 3/2008 | Fitzgibbon |

(56) References Cited

U.S. PATENT DOCUMENTS

| | | |
|---|---|---|
| 7,346,523 B1 | 3/2008 | Provost et al. |
| 7,346,555 B2 | 3/2008 | Rippingale et al. |
| 7,346,642 B1 | 3/2008 | Briggs et al. |
| 7,366,571 B2 | 4/2008 | Armstrong |
| 7,369,476 B2 | 5/2008 | Kravtchenko et al. |
| 7,370,069 B2 | 5/2008 | Chambers et al. |
| 7,373,318 B2 | 5/2008 | Kutsumi et al. |
| 7,373,342 B2 | 5/2008 | Cragun et al. |
| 7,376,700 B1 | 5/2008 | Clark et al. |
| 7,385,516 B2 | 6/2008 | Contractor |
| 7,386,101 B2 | 6/2008 | Pugliese |
| 7,389,245 B1 | 6/2008 | Ashford et al. |
| 7,394,011 B2 | 7/2008 | Huffman |
| 7,395,214 B2 | 7/2008 | Shillingburg |
| 7,395,216 B2 | 7/2008 | Rosenfeld et al. |
| 7,403,656 B2 | 7/2008 | Koga |
| 7,415,414 B2 | 8/2008 | Azara et al. |
| 7,417,205 B2 | 8/2008 | Faries, Jr. et al. |
| 7,433,827 B2 | 10/2008 | Rosenfeld et al. |
| 7,433,834 B2 | 10/2008 | Joao |
| 7,438,072 B2 | 10/2008 | Izuchukwu |
| 7,443,787 B2 | 10/2008 | Karino et al. |
| 7,444,291 B1 | 10/2008 | Prasad et al. |
| 7,454,067 B1 | 11/2008 | Pati |
| 7,454,299 B2 | 11/2008 | Bolz |
| 7,460,052 B2 | 12/2008 | Zemany et al. |
| 7,461,000 B2 | 12/2008 | Davis et al. |
| 7,464,043 B1 | 12/2008 | Dussia |
| 7,465,551 B2 | 12/2008 | Blumenthal et al. |
| 7,469,155 B2 | 12/2008 | Chu |
| 7,481,370 B2 | 1/2009 | Davis et al. |
| 7,483,721 B1 | 1/2009 | Vesikivi |
| 7,484,048 B2 | 1/2009 | Whitehouse |
| 7,485,095 B2 | 2/2009 | Shusterman |
| 7,487,114 B2 | 2/2009 | Florance et al. |
| 7,487,774 B2 | 2/2009 | Acker |
| 7,488,291 B2 | 2/2009 | Cho et al. |
| 7,490,048 B2 | 2/2009 | Joao |
| 7,493,281 B2 | 2/2009 | Vogel et al. |
| 7,508,298 B2 | 3/2009 | Pisz et al. |
| 7,511,260 B2 | 3/2009 | Sannomiya et al. |
| 7,525,425 B2 | 4/2009 | Diem |
| 7,526,123 B2 | 4/2009 | Moon et al. |
| 7,529,214 B2 | 5/2009 | Omae et al. |
| 7,533,353 B2 | 5/2009 | Dvorak et al. |
| 7,536,301 B2 | 5/2009 | Jaklitsch et al. |
| 7,536,360 B2 | 5/2009 | Stolfo et al. |
| 7,539,500 B2 | 5/2009 | Chiang |
| 7,539,656 B2 | 5/2009 | Fratkina et al. |
| 7,545,257 B2 | 6/2009 | Brue |
| 7,546,524 B1 | 6/2009 | Bryar et al. |
| 7,548,158 B2 | 6/2009 | Titus et al. |
| 7,552,039 B2 | 6/2009 | Dodds |
| 7,555,159 B2 | 6/2009 | Pishva |
| 7,555,444 B1 | 6/2009 | Wilson et al. |
| 7,557,728 B1 | 7/2009 | Bicheno et al. |
| 7,558,961 B2 | 7/2009 | Sharma et al. |
| 7,573,369 B2 | 8/2009 | Hayles, Jr. et al. |
| 7,580,832 B2 | 8/2009 | Allamanche et al. |
| 7,580,952 B2 | 8/2009 | Logan et al. |
| 7,587,369 B2 | 9/2009 | Ginter et al. |
| 7,590,275 B2 | 9/2009 | Clarke et al. |
| 7,590,547 B2 | 9/2009 | Lagadec et al. |
| 7,592,859 B2 | 9/2009 | Hastings |
| 7,599,892 B1 | 10/2009 | Berger et al. |
| 7,605,688 B1 | 10/2009 | Seah |
| 7,610,556 B2 | 10/2009 | Guo et al. |
| 7,613,620 B2 | 11/2009 | Salwan |
| 7,616,594 B2 | 11/2009 | Roberts et al. |
| 7,617,162 B2 | 11/2009 | Saini |
| 7,624,027 B1 | 11/2009 | Stern et al. |
| 7,624,051 B2 | 11/2009 | Gellman |
| 7,624,447 B1 | 11/2009 | Horowitz et al. |
| 7,627,334 B2 | 12/2009 | Cohen et al. |
| 7,627,577 B1 | 12/2009 | Lee et al. |
| 7,630,544 B1 | 12/2009 | Zhou |
| 7,630,762 B2 | 12/2009 | Sullivan et al. |
| 7,630,913 B2 | 12/2009 | Kay |
| 7,635,846 B2 | 12/2009 | Chi et al. |
| 7,639,396 B2 | 12/2009 | Bezryadin |
| 7,640,175 B1 | 12/2009 | Prasad et al. |
| 7,643,465 B2 | 1/2010 | Lorek et al. |
| 7,643,828 B2 | 1/2010 | Malladi et al. |
| 7,644,055 B2 | 1/2010 | Furst et al. |
| 7,647,049 B2 | 1/2010 | Engdahl et al. |
| 7,650,321 B2 | 1/2010 | Krishnan et al. |
| 7,650,811 B2 | 1/2010 | Matsui et al. |
| 7,653,457 B2 | 1/2010 | Bloom |
| 7,653,594 B2 | 1/2010 | Davis |
| 7,664,339 B2 | 2/2010 | Turski |
| 7,664,659 B2 | 2/2010 | Lancaster et al. |
| 7,668,647 B2 | 2/2010 | Barber et al. |
| 7,668,747 B2 | 2/2010 | Murphy et al. |
| 7,668,843 B2 | 2/2010 | Ertoz et al. |
| 7,671,795 B2 | 3/2010 | Rofougaran |
| 7,680,260 B2 | 3/2010 | Abramson et al. |
| 7,681,231 B2 | 3/2010 | Combs et al. |
| 7,682,025 B2 | 3/2010 | Sur et al. |
| 7,689,705 B1 | 3/2010 | Lester et al. |
| 7,693,653 B2 | 4/2010 | Hussain et al. |
| 7,696,751 B2 | 4/2010 | Molyneaux et al. |
| 7,698,154 B2 | 4/2010 | Marchosky |
| 7,703,691 B2 | 4/2010 | Patel et al. |
| 7,706,034 B2 | 4/2010 | Monga et al. |
| 7,706,068 B2 | 4/2010 | Takaaki |
| 7,707,044 B2 | 4/2010 | Graves et al. |
| 7,707,047 B2 | 4/2010 | Hasan et al. |
| 7,707,624 B2 | 4/2010 | Tomkow |
| 7,715,659 B2 | 5/2010 | Zhao et al. |
| 7,716,378 B2 | 5/2010 | Chen et al. |
| 7,725,253 B2 | 5/2010 | Foxlin |
| 7,730,005 B2 | 6/2010 | Gilliam et al. |
| 7,739,115 B1 | 6/2010 | Pettay et al. |
| 7,739,126 B1 | 6/2010 | Cave et al. |
| 7,742,193 B2 | 6/2010 | Kaltenbach et al. |
| 7,743,099 B2 | 6/2010 | Szeto |
| 7,752,058 B2 | 7/2010 | Sasaki et al. |
| 7,753,091 B2 | 7/2010 | Ozanne et al. |
| 7,775,329 B2 | 8/2010 | Eckenstein et al. |
| 7,778,483 B2 | 8/2010 | Messina et al. |
| 7,778,752 B1 | 8/2010 | Hunt et al. |
| 7,778,792 B2 | 8/2010 | Huang et al. |
| 7,778,816 B2 | 8/2010 | Reynar |
| 7,783,023 B2 | 8/2010 | Balk et al. |
| 7,783,379 B2 | 8/2010 | Beane et al. |
| 7,787,692 B2 | 8/2010 | Noguchi et al. |
| 7,787,693 B2 | 8/2010 | Siegemund |
| 7,793,835 B1 | 9/2010 | Coggeshall et al. |
| 7,797,145 B2 | 9/2010 | Dodds |
| 7,805,318 B1 | 9/2010 | Kuhn |
| 7,809,192 B2 | 10/2010 | Gokturk et al. |
| 7,809,378 B2 | 10/2010 | Contractor |
| 7,809,559 B2 | 10/2010 | Kushner et al. |
| 7,813,481 B1 | 10/2010 | Hursey et al. |
| 7,826,310 B2 | 11/2010 | Unkrich |
| 7,826,965 B2 | 11/2010 | Sadri et al. |
| 7,827,043 B2 | 11/2010 | Tahan |
| 7,827,234 B2 | 11/2010 | Eisenberger et al. |
| 7,828,554 B2 | 11/2010 | Fustolo |
| 7,831,559 B1 | 11/2010 | Mohan et al. |
| 7,835,506 B2 | 11/2010 | Groff et al. |
| 7,836,073 B2 | 11/2010 | Ahn |
| 7,844,363 B1 | 11/2010 | Mehdizadeh |
| 7,844,470 B2 | 11/2010 | Portnoy et al. |
| 7,844,837 B2 | 11/2010 | Youssef |
| 7,847,970 B1 | 12/2010 | McGrady |
| 7,847,989 B2 | 12/2010 | Blonde et al. |
| 7,849,398 B2 | 12/2010 | Dabet et al. |
| 7,853,586 B1 | 12/2010 | Patel et al. |
| 7,853,626 B2 | 12/2010 | Jung et al. |
| 7,856,137 B2 | 12/2010 | Yonezawa et al. |
| 7,856,142 B2 | 12/2010 | Ferman et al. |
| 7,856,289 B2 | 12/2010 | Schanin et al. |
| 7,860,281 B2 | 12/2010 | Pfister et al. |

(56) References Cited

U.S. PATENT DOCUMENTS

| | | |
|---|---|---|
| 7,860,552 B2 | 12/2010 | Borsook et al. |
| 7,860,732 B2 | 12/2010 | Elizabeth et al. |
| 7,860,935 B2 | 12/2010 | Lee et al. |
| 7,865,171 B2 | 1/2011 | Karlsson |
| 7,865,566 B2 | 1/2011 | Ashtekar et al. |
| 7,869,807 B2 | 1/2011 | Shimizu |
| 7,873,189 B2 | 1/2011 | Jee et al. |
| 7,885,687 B2 | 2/2011 | Serceki et al. |
| 7,887,493 B2 | 2/2011 | Stahmann et al. |
| 7,890,622 B2 | 2/2011 | Coca et al. |
| 7,894,448 B1 | 2/2011 | Lillibridge et al. |
| 7,894,812 B1 | 2/2011 | Durig et al. |
| 7,898,423 B2 | 3/2011 | Cavanaugh |
| 7,898,995 B2 | 3/2011 | Shahidi et al. |
| 7,899,677 B2 | 3/2011 | Kuo et al. |
| 7,899,739 B2 | 3/2011 | Allin et al. |
| 7,899,764 B2 | 3/2011 | Martin et al. |
| 7,903,880 B2 | 3/2011 | Wyatt et al. |
| 7,903,905 B2 | 3/2011 | Lapstun et al. |
| 7,908,518 B2 | 3/2011 | West, Jr. et al. |
| 7,911,482 B1 | 3/2011 | Mariano et al. |
| 7,912,201 B2 | 3/2011 | Martin et al. |
| 7,912,288 B2 | 3/2011 | Winn et al. |
| 7,913,162 B2 | 3/2011 | Hansen et al. |
| 7,916,137 B2 | 3/2011 | Pearman et al. |
| 7,916,707 B2 | 3/2011 | Fontaine |
| 7,917,377 B2 | 3/2011 | Rao et al. |
| 7,921,088 B1 | 4/2011 | Mittal |
| 7,924,149 B2 | 4/2011 | Mendelson |
| 7,925,058 B2 | 4/2011 | Lee et al. |
| 7,929,950 B1 | 4/2011 | Rao et al. |
| 7,932,830 B2 | 4/2011 | Campero et al. |
| 7,932,837 B2 | 4/2011 | Giesa et al. |
| 7,935,055 B2 | 5/2011 | Burckhardt |
| 7,940,602 B1 | 5/2011 | Korolenko |
| 7,940,744 B2 | 5/2011 | Lehotsky et al. |
| 7,940,982 B1 | 5/2011 | Shaick |
| 7,941,009 B2 | 5/2011 | Li et al. |
| 7,941,124 B2 | 5/2011 | Adamczyk et al. |
| 7,941,505 B2 | 5/2011 | Jaye |
| 7,942,817 B2 | 5/2011 | Zhang et al. |
| 7,949,191 B1 | 5/2011 | Ramkumar et al. |
| 7,949,643 B2 | 5/2011 | Kawale et al. |
| 7,957,966 B2 | 6/2011 | Takeuchi |
| 7,959,568 B2 | 6/2011 | Stahmann et al. |
| 7,962,283 B2 | 6/2011 | Zhang et al. |
| 7,962,350 B1 | 6/2011 | Provost et al. |
| 7,962,359 B2 | 6/2011 | Montoya |
| 7,966,532 B2 | 6/2011 | Bottelli et al. |
| 7,967,141 B2 | 6/2011 | Witczak |
| 7,969,143 B2 | 6/2011 | Gilboa |
| 7,970,552 B1 | 6/2011 | Stefanon et al. |
| 7,970,660 B2 | 6/2011 | Bezos et al. |
| 7,972,274 B2 | 7/2011 | Bardy |
| 7,973,820 B2 | 7/2011 | Ohara et al. |
| 7,975,913 B2 | 7/2011 | Kubota et al. |
| 7,976,171 B2 | 7/2011 | Kameoka et al. |
| 7,978,639 B2 | 7/2011 | Maltseff et al. |
| 7,979,086 B1 | 7/2011 | Jones et al. |
| 7,979,286 B2 | 7/2011 | Manning et al. |
| 7,979,289 B2 | 7/2011 | Callas |
| 7,979,585 B2 | 7/2011 | Chen et al. |
| 7,983,611 B2 | 7/2011 | Rao |
| 7,983,677 B2 | 7/2011 | Dacosta |
| 7,986,237 B2 | 7/2011 | Jung |
| 7,986,828 B2 | 7/2011 | Rao et al. |
| 7,986,940 B2 | 7/2011 | Lee et al. |
| 7,988,043 B2 | 8/2011 | Davis |
| 7,991,485 B2 | 8/2011 | Zakim |
| 7,996,074 B2 | 8/2011 | KenKnight et al. |
| 7,996,519 B1 | 8/2011 | Brown et al. |
| 8,000,528 B2 | 8/2011 | Ming et al. |
| 8,000,723 B2 | 8/2011 | Pande et al. |
| 8,000,892 B2 | 8/2011 | Banerjee |
| 8,000,979 B2 | 8/2011 | Blom |
| 8,002,144 B2 | 8/2011 | Percy |
| 8,005,263 B2 | 8/2011 | Fujimura et al. |
| 8,005,488 B2 | 8/2011 | Staffaroni et al. |
| 8,005,672 B2 | 8/2011 | Vierthaler et al. |
| 8,005,685 B1 | 8/2011 | Bird |
| 8,005,687 B1 | 8/2011 | Pederson et al. |
| 8,005,875 B2 | 8/2011 | Hickey et al. |
| 8,008,285 B2 | 8/2011 | Roberts et al. |
| 8,010,126 B2 | 8/2011 | Moton, Jr. et al. |
| 8,010,664 B2 | 8/2011 | Firminger et al. |
| 8,014,562 B2 | 9/2011 | Rhoads et al. |
| 8,015,006 B2 | 9/2011 | Kennewick et al. |
| 8,019,168 B2 | 9/2011 | Hanami |
| 8,023,485 B2 | 9/2011 | Shi et al. |
| 8,024,179 B2 | 9/2011 | Pulz et al. |
| 8,026,850 B2 | 9/2011 | Seong et al. |
| 8,027,784 B2 | 9/2011 | Geelen |
| 8,032,399 B2 | 10/2011 | Brown |
| 8,036,735 B2 | 10/2011 | Cazares et al. |
| 8,039,093 B2 | 10/2011 | Leenders et al. |
| 8,041,017 B2 | 10/2011 | Goldman et al. |
| 8,041,454 B2 | 10/2011 | Blust et al. |
| 8,041,570 B2 | 10/2011 | Mirkovic et al. |
| 8,044,798 B2 | 10/2011 | Icove et al. |
| 8,045,693 B2 | 10/2011 | Yao |
| 8,045,805 B2 | 10/2011 | Ramsay et al. |
| 8,045,929 B2 | 10/2011 | Twitchell, Jr. |
| 8,046,371 B2 | 10/2011 | O'Clair et al. |
| 8,049,597 B1 | 11/2011 | Murakami et al. |
| 8,055,240 B2 | 11/2011 | Kim |
| 8,056,118 B2 | 11/2011 | Piliouras |
| 8,060,562 B2 | 11/2011 | Chesley |
| 8,061,592 B1 | 11/2011 | Clem et al. |
| 8,064,884 B2 | 11/2011 | Wu et al. |
| 8,065,162 B1 | 11/2011 | Curry |
| 8,065,250 B2 | 11/2011 | Stephens |
| 8,065,347 B1 | 11/2011 | DeMeyer et al. |
| 8,065,669 B2 | 11/2011 | Donovan et al. |
| 8,068,008 B2 | 11/2011 | Connell, II et al. |
| 8,068,603 B2 | 11/2011 | Conrad et al. |
| 8,068,917 B2 | 11/2011 | Petersen et al. |
| 8,068,933 B2 | 11/2011 | Walker et al. |
| 8,069,080 B2 | 11/2011 | Rastogi |
| 8,069,213 B2 | 11/2011 | Bloch et al. |
| 8,069,236 B2 | 11/2011 | Agraharam et al. |
| 8,070,739 B2 | 12/2011 | Zinger et al. |
| 8,072,310 B1 | 12/2011 | Everhart |
| 8,073,013 B2 | 12/2011 | Coleman et al. |
| 8,073,711 B1 | 12/2011 | McCollum et al. |
| 8,074,007 B2 | 12/2011 | James |
| 8,078,606 B2 | 12/2011 | Slackman |
| 8,082,122 B2 | 12/2011 | No et al. |
| 8,083,406 B2 | 12/2011 | Bowers et al. |
| 8,140,592 B2 | 3/2012 | Scott et al. |
| 8,155,811 B2 | 4/2012 | Noffsinger et al. |
| 8,188,880 B1 | 5/2012 | Chi et al. |
| 8,203,640 B2 | 6/2012 | Kim et al. |
| 8,255,147 B2 | 8/2012 | Roberts et al. |
| 8,259,169 B2 | 9/2012 | Sugio et al. |
| 8,290,701 B2 | 10/2012 | Mason et al. |
| 8,295,556 B2 | 10/2012 | Ohtani et al. |
| 8,392,212 B2 | 3/2013 | Beraja et al. |
| 8,462,231 B2 | 6/2013 | Nusbaum |
| 8,510,133 B2 | 8/2013 | Peak et al. |
| 8,662,388 B2 | 3/2014 | Belkin |
| 8,694,334 B2 | 4/2014 | Ryan et al. |
| 8,700,423 B2 | 4/2014 | Eaton, Jr. et al. |
| 8,744,876 B2 | 6/2014 | Gross |
| 8,786,402 B2 | 7/2014 | Barnes |
| 2002/0032583 A1 | 3/2002 | Joao |
| 2002/0044043 A1 | 4/2002 | Chaco et al. |
| 2002/0169635 A1 | 11/2002 | Shillingburg |
| 2003/0036683 A1 | 2/2003 | Kehr et al. |
| 2003/0055685 A1 | 3/2003 | Cobb et al. |
| 2003/0212060 A1 | 11/2003 | Tollefson |
| 2003/0212314 A1 | 11/2003 | Takahashi et al. |
| 2004/0137539 A1 | 7/2004 | Bradford |
| 2004/0138724 A1 | 7/2004 | Sieracki et al. |
| 2005/0065815 A1 | 3/2005 | Mazar et al. |

(56) References Cited

U.S. PATENT DOCUMENTS

| | | | |
|---|---|---|---|
| 2005/0102159 A1 | 5/2005 | Mondshine | |
| 2006/0006999 A1* | 1/2006 | Walczyk | A61B 5/1113 340/539.27 |
| 2006/0106646 A1 | 5/2006 | Squilla et al. | |
| 2006/0122864 A1 | 6/2006 | Gottesman et al. | |
| 2006/0149591 A1 | 7/2006 | Hanf et al. | |
| 2006/0161457 A1 | 7/2006 | Rapaport et al. | |
| 2006/0181243 A1 | 8/2006 | Graves et al. | |
| 2006/0218011 A1 | 9/2006 | Walker et al. | |
| 2006/0224419 A1 | 10/2006 | Servizio et al. | |
| 2006/0285441 A1 | 12/2006 | Walker et al. | |
| 2007/0016443 A1 | 1/2007 | Wachman et al. | |
| 2007/0046476 A1 | 3/2007 | Hinkamp | |
| 2007/0179356 A1 | 8/2007 | Wessel | |
| 2007/0225350 A1 | 9/2007 | Anderson et al. | |
| 2008/0045806 A1 | 2/2008 | Keppler | |
| 2008/0103369 A1 | 5/2008 | Fabius et al. | |
| 2008/0149701 A1 | 6/2008 | Lane | |
| 2008/0306759 A1 | 12/2008 | Ilkin et al. | |
| 2009/0047645 A1 | 2/2009 | Dibenedetto et al. | |
| 2009/0119124 A1 | 5/2009 | Kambaloor | |
| 2009/0125324 A1 | 5/2009 | Keravich et al. | |
| 2009/0136094 A1 | 5/2009 | Driver et al. | |
| 2009/0206992 A1 | 8/2009 | Giobbi et al. | |
| 2009/0281825 A1 | 11/2009 | Larsen | |
| 2010/0054601 A1 | 3/2010 | Anbalagan et al. | |
| 2010/0138232 A1 | 6/2010 | Ryan et al. | |
| 2010/0145736 A1 | 6/2010 | Rohwer | |
| 2010/0161353 A1 | 6/2010 | Mayaud | |
| 2010/0205008 A1 | 8/2010 | Hua et al. | |
| 2010/0211531 A1 | 8/2010 | Roberts et al. | |
| 2010/0217623 A1 | 8/2010 | Schoenberg et al. | |
| 2010/0262430 A1 | 10/2010 | Gips et al. | |
| 2010/0268303 A1 | 10/2010 | Mitchell et al. | |
| 2010/0286490 A1 | 11/2010 | Koverzin | |
| 2010/0315225 A1 | 12/2010 | Teague | |
| 2010/0321180 A1* | 12/2010 | Dempsey et al. | 340/539.12 |
| 2010/0324936 A1 | 12/2010 | Vishnubhatla et al. | |
| 2011/0093296 A1 | 4/2011 | Klink | |
| 2011/0130635 A1 | 6/2011 | Ross | |
| 2011/0145012 A1 | 6/2011 | Nightingale et al. | |
| 2011/0166885 A1 | 7/2011 | Walker et al. | |
| 2011/0213625 A1 | 9/2011 | Joao | |
| 2011/0295622 A1* | 12/2011 | Farooq et al. | 705/3 |
| 2011/0295631 A1 | 12/2011 | Kennedy et al. | |
| 2011/0313788 A1 | 12/2011 | Amland et al. | |
| 2012/0046965 A1 | 2/2012 | Ryan et al. | |
| 2012/0072232 A1 | 3/2012 | Frankham et al. | |
| 2012/0095779 A1 | 4/2012 | Wengrovitz et al. | |
| 2012/0129139 A1 | 5/2012 | Partovi | |
| 2012/0265544 A1 | 10/2012 | Hwang et al. | |
| 2012/0296671 A1 | 11/2012 | Simons-Nikolova et al. | |
| 2012/0316896 A1 | 12/2012 | Rahman et al. | |
| 2013/0029768 A1 | 1/2013 | Eichstaedt et al. | |

OTHER PUBLICATIONS

U.S. Appl. No. 13/066,442, Hwang et al.

West, Darrell; "Enabling Personalized Medicine through Health Information Technology"; Center for Technology Innovation at Brookings; Jan. 28, 2011; pp. 1-20 plus cover page; The Brookings Institution.

U.S. Appl. No. 13/199,051, Hyde et al.

U.S. Appl. No. 13/066,444, Hwang et al.

Hines, Ph. D., Steve; "Reducing Avoidable Hospital Readmissions"; Florida Hospital Association Meeting; Jun. 4, 2010; 34 pages; Health Research and Educational Trust.

Excerpts from Google Search: "touch screen and touch input on image and recognize person in image"; Google Patents Search (as provided by Examiner) (best copy available); bearing a date of Nov. 19, 2015; pp 1-2; located at: https://www.google.com/search?q=touch+screen+and+touch+input+on+image+and+recognize+person+in+image&biw=1851&bih=1078&source=Int&tbs=pto . . . .

Google Search Excerpts: "medical devices and detect communication delay and automatic response and initiating communication"; Google Patents Search (as provided by Examiner) (best copy available); bearing a date of Oct. 13, 2016; 2 pages; located at: https://www.google.com/?tbm+pts#q=medical+devices+and+detect+communication+delay+and+automatic+response+and+initiating+communications&tbs=pt . . . .

Google Search Excerpts: "building camera and capture images and person"; Google Patents Search (as provided by Examiner); bearing a date of Feb. 28, 2017; pp. 1-2; Google.

Google Search Excerpts: "selecting a person on an image and verbally validate the person on the image"; Google Patents Search (as provided by Examiner); bearing a date of Feb. 28, 2017; pp. 1-2; Google.

Portable drug dispenser and remote authorization and controlling dispensation; Google patents search; Sep. 8, 2017; pp. 1-2.

\* cited by examiner

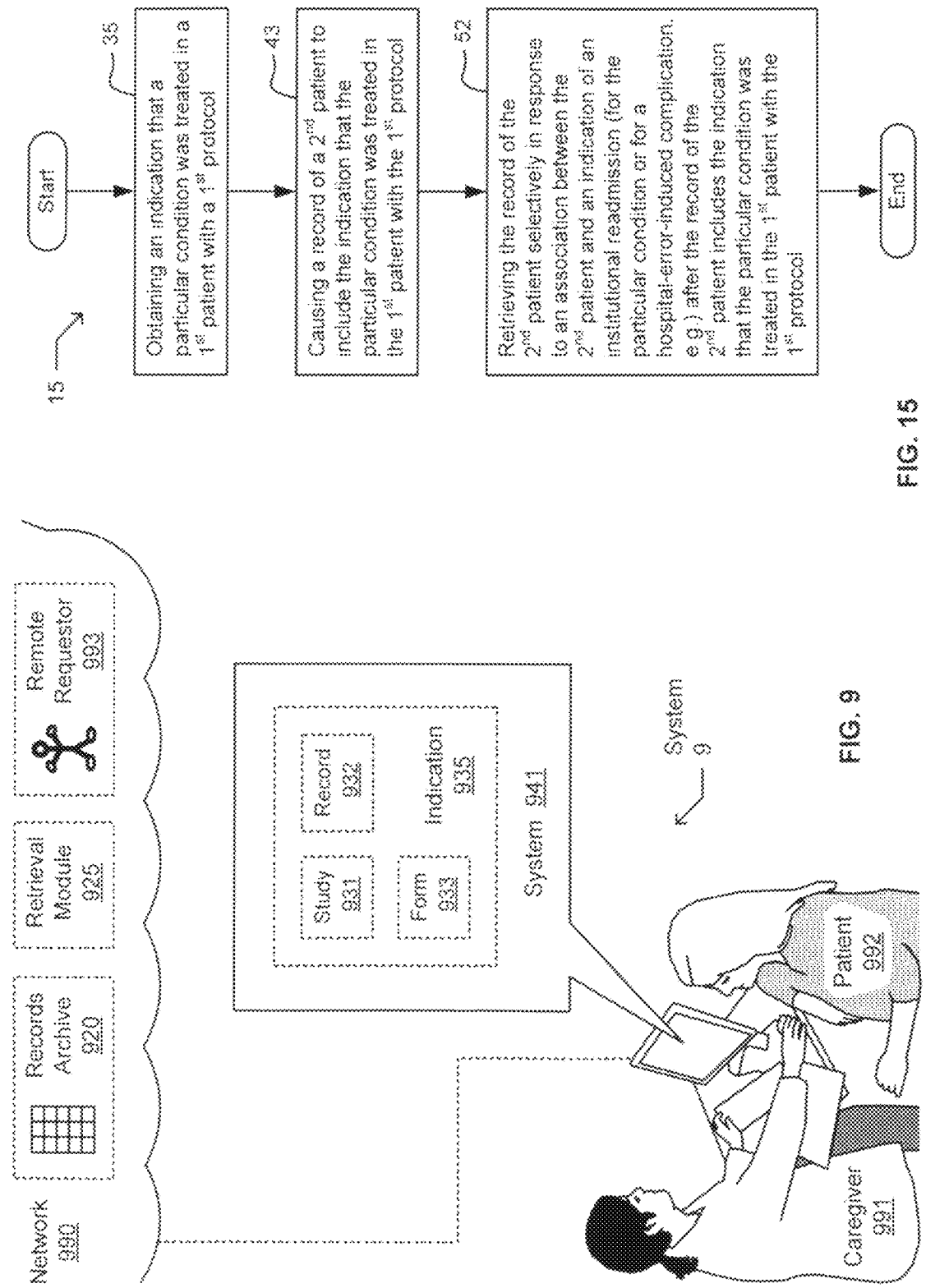

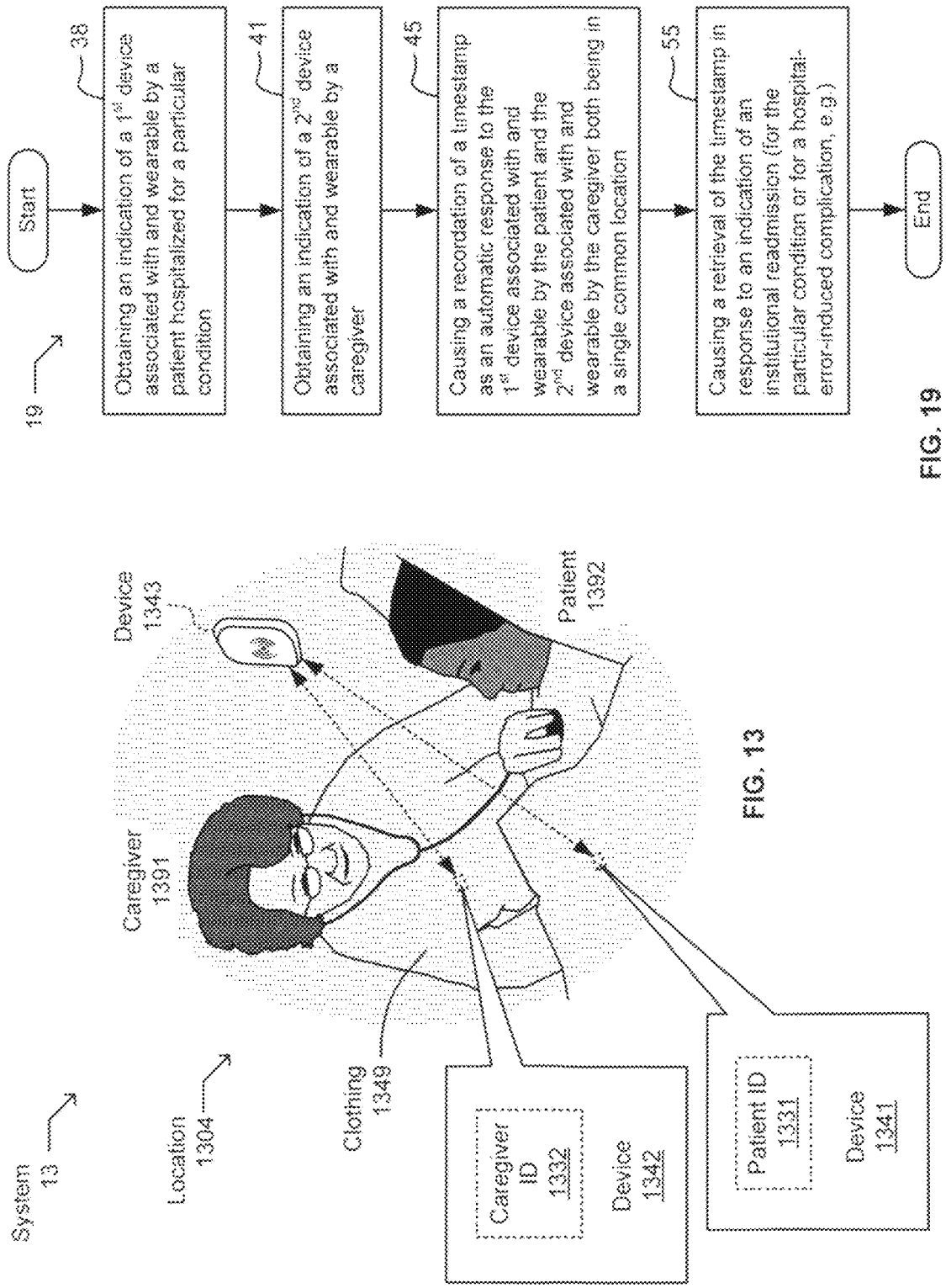

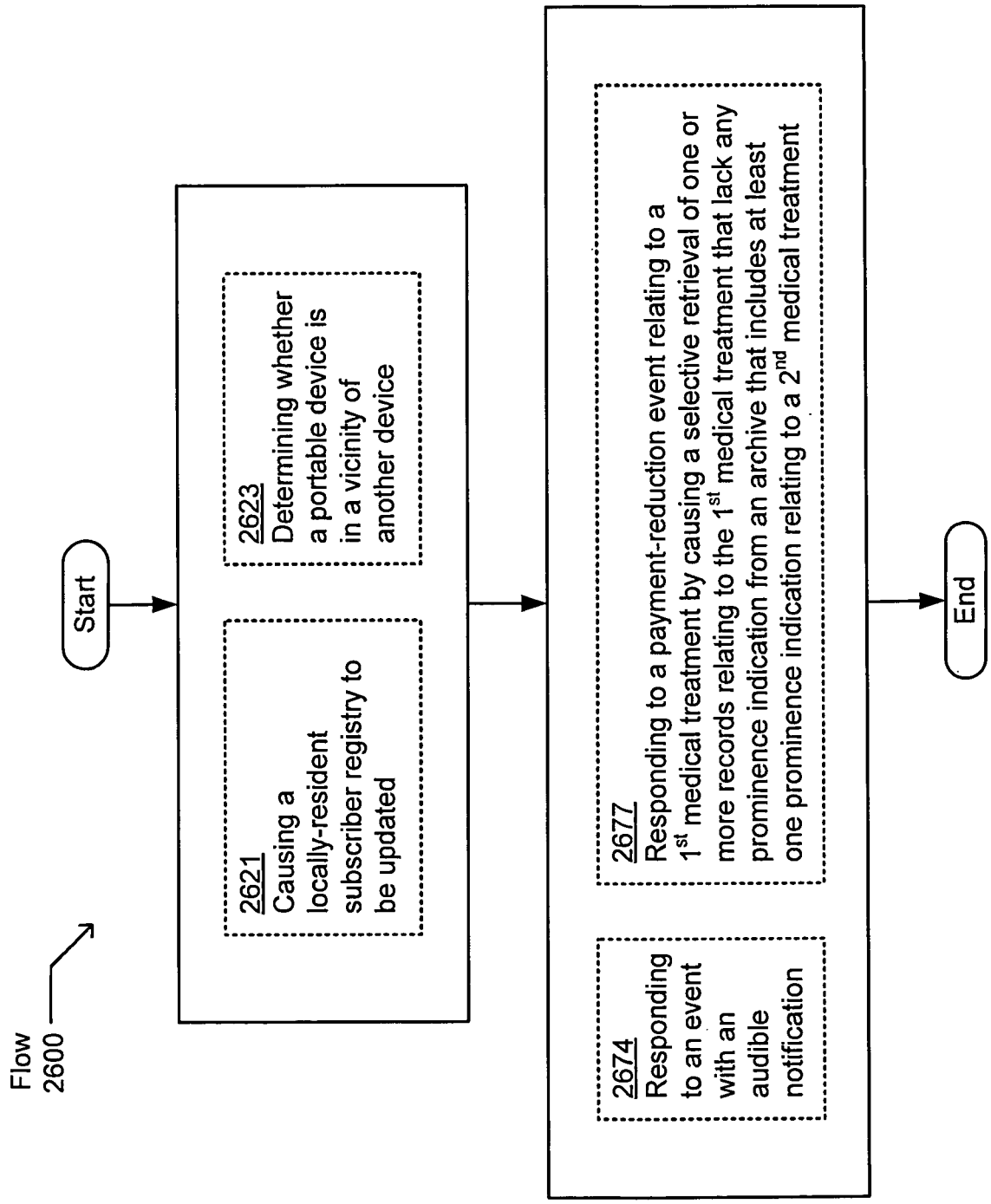

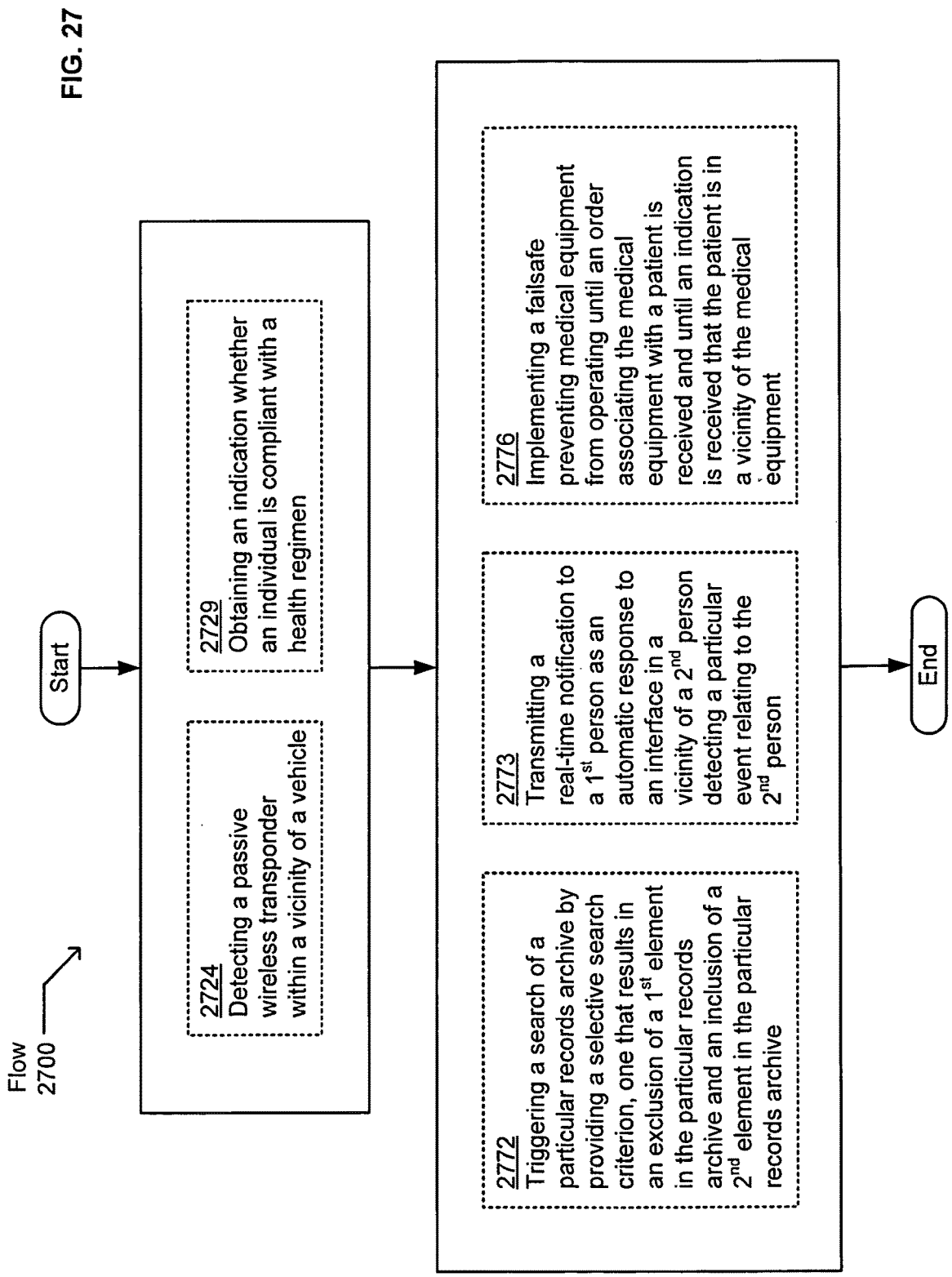

EVIDENCE-BASED HEALTHCARE INFORMATION MANAGEMENT PROTOCOLS

CROSS-REFERENCE TO RELATED APPLICATIONS

The present application is related to and claims the benefit of the earliest available effective filing date(s) from the following listed application(s) (the "Related applications") (e.g., claims earliest available priority dates for other than provisional patent applications or claims benefits under 35 USC § 119(e) for provisional patent applications, for any and all parent, grandparent, great-grandparent, etc. applications of the Related application(s)). All subject matter of the Related applications and of any and all parent, grandparent, great-grandparent, etc. applications of the Related applications, including any priority claims, is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 13/374,747, U.S. patent application Ser. No. 13/374,750, U.S. patent application Ser. No. 13/374,745, and U.S. patent application Ser. No. 13/374,744, each entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012, each of which is currently co-pending or is an application of which a currently co-pending application is entitled to the benefit of the filing date. Likewise the present application constitutes a continuation-in-part of U.S. patent application Ser. No. 13/374,519, also entitled EVIDENCE-BASED HEALTHCARE INFORMATION MANAGEMENT PROTOCOLS and naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 30 Dec. 2011, which is currently co-pending.

For purposes of the USPTO extra-statutory requirements, the present application claims benefit of priority of U.S. patent application Ser. No. 13/374,747, U.S. patent application Ser. No. 13/374,750, U.S. patent application Ser. No. 13/374,745, and U.S. patent application Ser. No. 13/374,744, each entitled EVIDENCE-BASED HEALTHCARE INFORMATION MANAGEMENT PROTOCOLS, naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 9 Jan. 2012, each of which was filed within the twelve months preceding the filing date of the present application or is an application of which a currently co-pending application is entitled to the benefit of the filing date. Likewise the present application claims benefit of priority of U.S. patent application Ser. No. 13/374,519, also entitled EVIDENCE-BASED HEALTHCARE INFORMATION MANAGEMENT PROTOCOLS and naming Roderick A. Hyde; Edward K. Y. Jung; Jordin T. Kare; Eric C. Leuthardt; Royce A. Levien; Richard T. Lord; Robert W. Lord; Mark A. Malamud; John D. Rinaldo, Jr.; Dennis J. Rivet; Clarence T. Tegreene; and Lowell L. Wood, Jr. as inventors, filed 30 Dec. 2011, which was filed within the twelve months preceding the filing date of the present application.

The United States Patent Office (USPTO) has published a notice to the effect that the USPTO's computer programs require that patent applicants reference both a serial number and indicate whether an application is a continuation, continuation-in-part, or divisional of a parent application. Stephen G. Kunin, Benefit of Prior-Filed Application, USPTO Official Gazette Mar. 18, 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant has provided designation(s) of a relationship between the present application and its parent application(s) as set forth above, but expressly points out that such designation(s) are not to be construed in any way as any type of commentary and/or admission as to whether or not the present application contains any new matter in addition to the matter of its parent application(s).

TECHNICAL FIELD

This disclosure relates to managing information in an evidence-based medical practice, particularly data relating to patients or to diagnostic or therapeutic treatments.

SUMMARY

An embodiment provides a method. In one implementation, the method includes but is not limited to causing an electronic record of a first protocol (comprising one or more instances of diagnostic evaluations, regimen implementations, or medical interventions, e.g.) for a particular condition (comprising one or more instances of injuries, complaints, or pathologies, e.g.) to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for causing an electronic record of a first protocol for a particular condition to be annotated with a scan of a document and circuitry for retrieving the electronic record of the first protocol after the electronic record of the first protocol is annotated with the scan of the document partly based on an indication of a first patient undergoing the first protocol and partly based on an indication of an institutional readmission.

In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to causing an electronic record of a first protocol for a particular condition to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for causing an electronic record of a first protocol for a particular condition to be annotated with a scan of a document and retrieving the electronic record of the first protocol after the electronic record of the first protocol is annotated with the scan of the document partly based on an indication of a first patient undergoing the first protocol and partly based on an indication of an institutional readmission. In addition to the foregoing, other system aspects are described in the claims, drawings, and text forming a part of the present disclosure.

An embodiment provides a method. In one implementation, the method includes but is not limited to obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication that a particular condition was treated in a first patient with a first protocol; circuitry for causing a record of a second patient to include the indication that the particular condition was treated in the first patient with the first protocol; and circuitry for retrieving the record of the second patient selectively in response to an association between the second patient and an indication of an institutional readmission after the record of the second patient includes the indication that the particular condition was treated in the first patient with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication that a particular condition was treated in a first patient with a first protocol; causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol. In addition to the foregoing, other system aspects are described in the claims, drawings, and text forming a part of the present disclosure.

An embodiment provides a method. In one implementation, the method includes but is not limited to obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication of a first protocol being employed in relation to a particular condition in a first patient; circuitry for requesting an effectiveness indication of the first protocol from an entity partly based on the entity validating the first protocol and partly based on a first communication delay associated with the first protocol, the first communication delay exceeding one hour; and circuitry for signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication of a first protocol being employed in relation to a particular condition in a first patient; requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol. In addition to the foregoing, other system aspects are described in the claims, drawings, and text forming a part of the present disclosure.

An embodiment provides a method. In one implementation, the method includes but is not limited to obtaining an association between a particular condition and a first protocol; causing a comparison between a threshold and a prominence indication of treating the particular condition with the first protocol after the association between the particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an association between a particular condition and a first protocol; circuitry for causing a comparison between a threshold and a prominence indication of treating the particular condition with the first protocol after the association between the particular condition and the first protocol is obtained; and circuitry for signaling a decision whether to caution a caregiver partly based on the association between the particular condition and the first protocol and partly based on the comparison between the threshold and the prominence indication of treating the particular condition with the first protocol. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an association between a particular condition and a first protocol; causing a comparison between a threshold and a prominence indication of treating the particular condition with the first protocol after the association between the particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an association between a particular condition and a first protocol; causing a comparison between a threshold and a prominence indication of treating the particular condition with the first protocol after the association between the particular condition and the first protocol is obtained; and signaling a decision whether to caution a caregiver partly based on the association between the particular condition and the first protocol and partly based on the comparison between the threshold and the prominence indication of treating the particular condition with the first protocol. In addition to the foregoing, other system aspects are described in the claims, drawings, and text forming a part of the present disclosure.

An embodiment provides a method. In one implementation, the method includes but is not limited to obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an association between a care administration space and a first device; circuitry for obtaining via a second device a patient consent conditionally authorizing a release of a first medical record, the second device being a mobile device; and circuitry for causing the first device to receive the first medical record partly based on the second device entering the care administration space and partly based on the patient consent authorizing the release of the first medical record. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an association between a care administration space and a first device; obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record. In addition to the foregoing, other system aspects are described in the claims, drawings, and text forming a part of the present disclosure.

An embodiment provides a method. In one implementation, the method includes but is not limited to obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other method aspects are described in the claims, drawings, and text forming a part of the present disclosure.

In one or more various aspects, related machines, compositions of matter, or manufactures of systems may include virtually any combination permissible under 35 U.S.C. § 101 of hardware, software, and/or firmware configured to effect the herein-referenced method aspects depending upon the design choices of the system designer.

An embodiment provides a system. In one implementation, the system includes but is not limited to circuitry for obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other system aspects are described in the claims, drawings, and text forming a part of the present disclosure.

An embodiment provides an article of manufacture including a computer program product. In one implementation, the article of manufacture includes but is not limited to a signal-bearing medium configured by one or more instructions related to obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other computer program product aspects are described in the claims, drawings, and text forming a part of the present disclosure.

An embodiment provides a system. In one implementation, the system includes but is not limited to a computing device and instructions. The instructions when executed on the computing device configure the computing device for obtaining an indication of a first device associated with and wearable by a patient hospitalized for a particular condition; obtaining an indication of a second device associated with and wearable by a caregiver; causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location. In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure. The foregoing is a summary and thus may contain simplifications, generalizations, inclusions, and/or omissions of detail; consequently, those skilled in the art will appreciate that the summary is illustrative only and is NOT intended to be in any way limiting. Other aspects, features,

BRIEF DESCRIPTION OF THE FIGURES

FIGS. 8-13 respectively depict exemplary environments in which one or more technologies may be configured to operate between or among respective devices.

FIG. 15 depicts a high-level logic flow of an operational process described with reference to FIG. 9.

FIG. 19 depicts a high-level logic flow of an operational process described with reference to FIG. 13.

FIG. 26 likewise depicts variants of earlier-presented flows.

FIG. 27 likewise depicts variants of earlier-presented flows.

DETAILED DESCRIPTION

Figure 1:
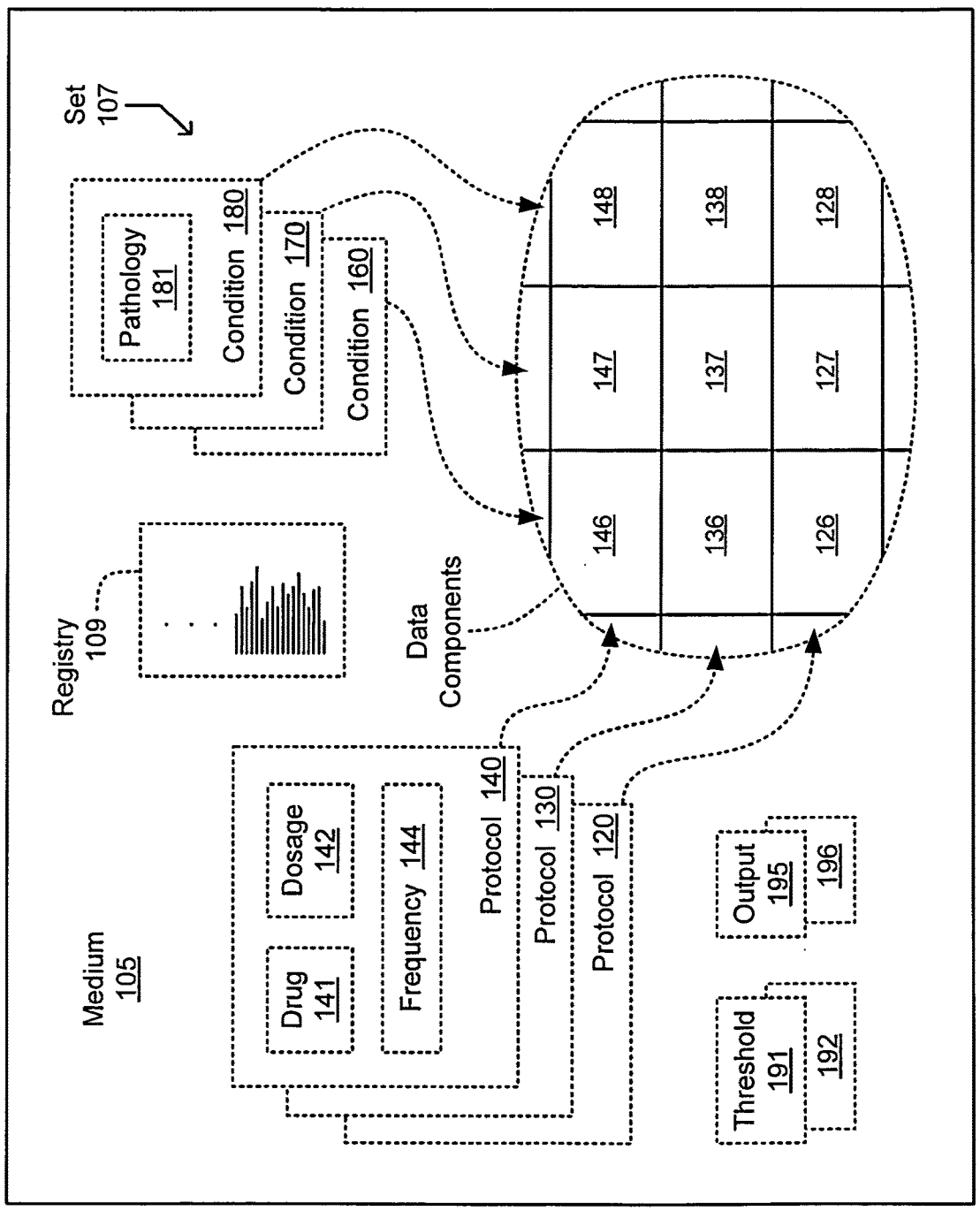
FIG. 1 depicts an exemplary environment in which one or more technologies may be implemented in one or more data-handling media.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described below. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

In a general sense, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

In a general sense, those skilled in the art will also recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will further recognize that at least a portion of the devices and/or processes described herein can be integrated into an image processing system. A typical image processing system may generally include one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system may be implemented utilizing suitable commercially available components, such as those typically found in digital still systems and/or digital motion systems.

Those skilled in the art will likewise recognize that at least some of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

With reference now to FIG. 1, shown is an example of a system 1 (a network subsystem, e.g.) in which one or more technologies may be implemented. One or more media 105 are configured to bear one or more instances of a registry 109 (of multiple subscribers, e.g.); organized informational data components relating to health-related protocols 120, 130, 140 relating to the treatment of various conditions 160, 170, 180 (symptoms or pathologies 181 or sets 107 thereof, e.g.); thresholds 191, 192; and outputs 195, 196. One or more such data components 126 relate specifically to the handling of condition 160 using protocol 120 prospectively or otherwise, for example, for one or more particular patients or more generally as described below. (Such sets 107 of pathologies 181 may comprise one or more of an addiction or chronic pain or major depression, for example.) One or more data components 127 likewise relate specifically to the handling of condition 170 using protocol 120 (MRI screening followed by magnetic stimulation therapy, e.g.). One or more data components 128 likewise relate specifically to the handling of condition 180 using protocol 120.

One or more data components 136 likewise relate specifically to the handling of condition 160 using protocol 130. One or more data components 137 likewise relate specifically to the handling of condition 170 (hypertension with major depression in a male of 50 years or older, e.g.) using protocol 130 (a series of ten weekly counseling sessions, e.g.). One or more data components 138 likewise relate specifically to the handling of condition 180 using protocol 130.

One or more data components 146 likewise relate specifically to the handling of condition 160 using protocol 140. One or more data components 147 likewise relate specifically to the handling of condition 170 (major depression, e.g.) using protocol 140. In some contexts, protocol 140 may comprise a particular drug 141 (sertraline, e.g.) taken at a particular dosage (50 milligrams, e.g.) with a particular frequency 144 (daily, e.g.). One or more data components 148 likewise relate specifically to the handling of condition 180 using protocol 140.

A wide variety of conditions 160, 170, 180 of interest may be identified using one or more common medical classification publications: the ICD (International Classification of Diseases); the ICSD (International Classification of Sleep Disorders); the NANDA (North American Nursing Diagnosis Association); the DSM-IV (Diagnostic and Statistical Manual of Mental Disorders); the Mendelian Inheritance in Man; and the SNOMED (Systematized Nomenclature of Human Medicine, D axis). In practical terms, records signaling such conditions may also comprise textual descriptors to locate misclassified or other data components 126, 137, 148 that signal such conditions 160, 170, 180 of interest (in a physician's remarks or other annotations relating to patients who have been readmitted to a hospital or psychiatric facility, e.g.).

Likewise a wide variety of protocols 120, 130, 140 (of diagnosis or treatment, e.g.) of interest may be identified using one or more common procedure codes in various publications: the ICHI (International Classification of Health Interventions); the ICPM (International Classification of Procedures in Medicine); the ICPC-2 (International Classification of Primary Care); the HCPCS (Healthcare Common Procedure Coding System); the ICD-10-PCS and the ICD-9-CM Volume 3 (International Classification of Diseases); the NIC (Nursing Interventions Classification); the NMDS (Nursing Minimum Data Set); the NOC (Nursing Outcomes Classification); the SNOMED (Systematized Nomenclature of Human Medicine, P axis); and the CPT (Current Procedural Terminology) codes. In practical terms, records signaling such protocols may also comprise DRG (Diagnosis Related Group) codes or textual descriptors to locate misclassified or other data components 126, 137, 148 that signal such protocols 120, 130, 140 of interest.

Figure 2:
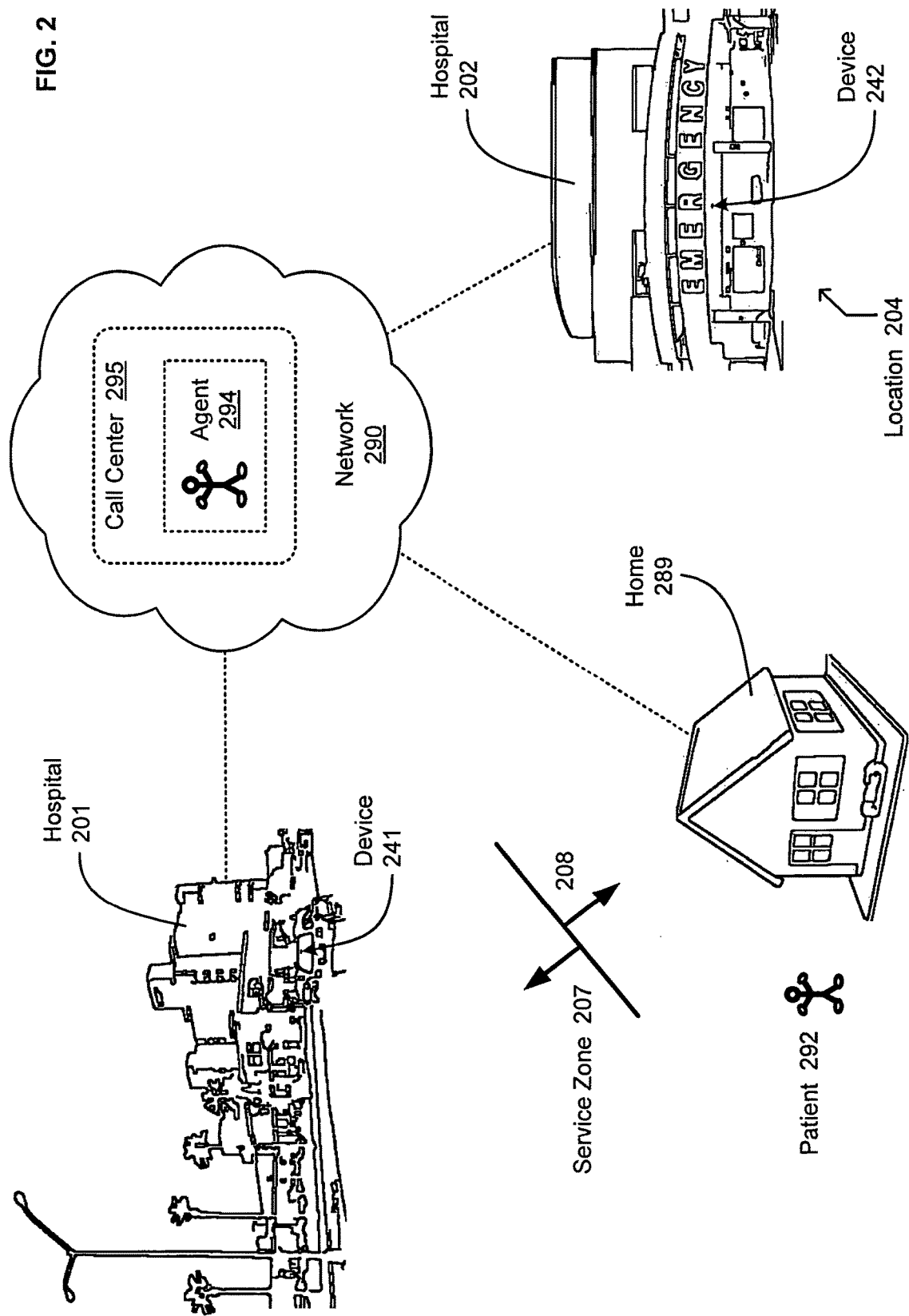
FIG. 2 depicts an exemplary environment in which one or more technologies may facilitate coordination between a hospital and one or more other facilities.

With reference now to FIG. 2, shown is an example of various institutions among which one or more technologies may be implemented. A motor vehicle bearing a mobile device 241 is shown in a vicinity of a hospital 201 on a network 290 (the Internet or a phone network, e.g.) shared with another hospital 202 and a home 289 of a patient 292. In some contexts, network 290 may include one or more call centers 295 operated by one or more agents 294 as described below. A stationary device 242 is configured to monitor a location 204 within which it resides (in or near an emergency room of hospital 202, e.g.). In the particular context as shown, hospital 201 is in one service zone 207 and hospital 202 is in a second service zone 208.

Figure 3:
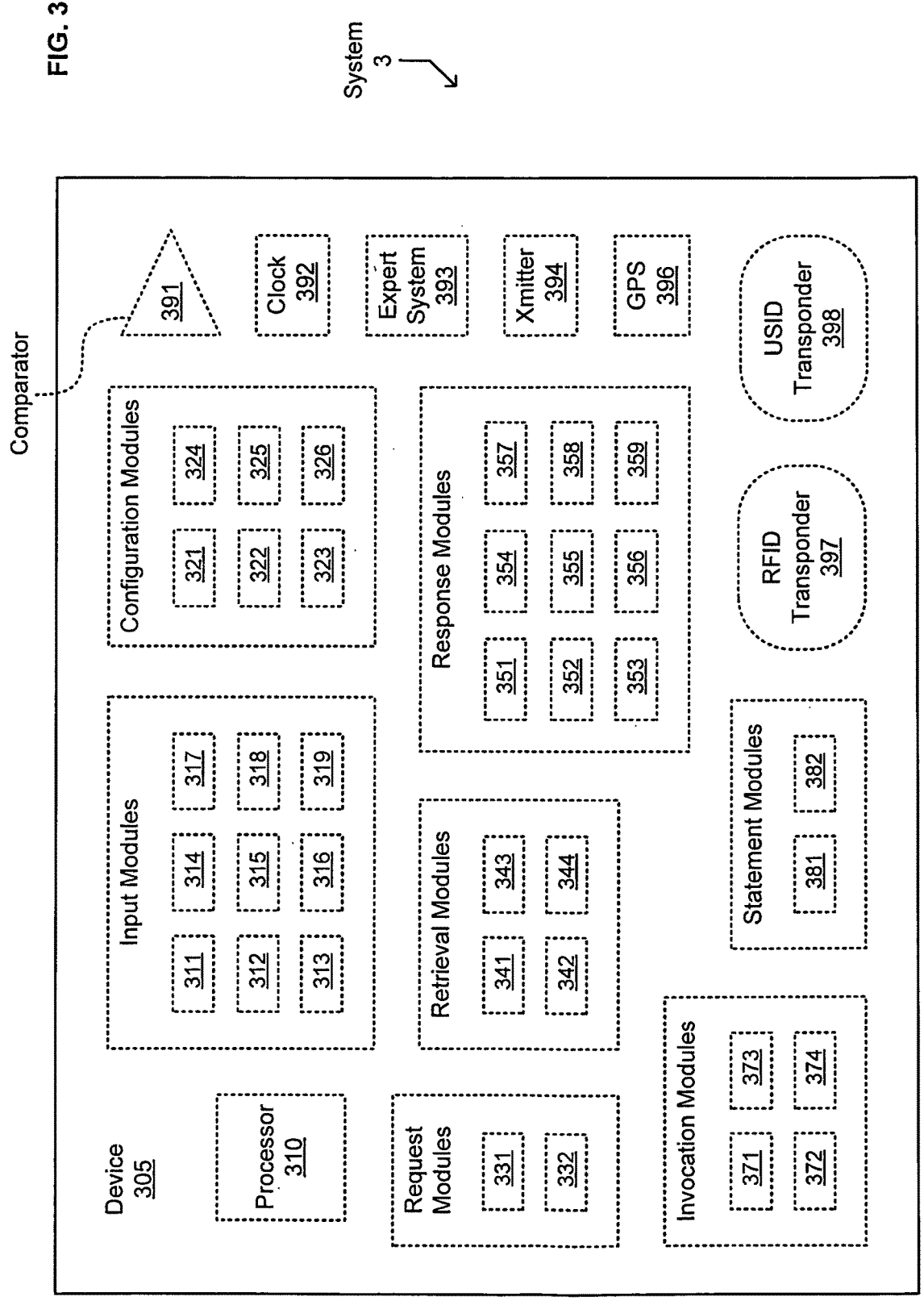
FIG. 3 depicts an exemplary environment in which one or more technologies may be implemented in a device.

With reference now to FIG. 3, shown is an example of a system 3 (a subsystem comprising network 290, e.g.) in which one or more technologies may be implemented. Device 305 may (optionally) include one or more instances of input modules 311, 312, 313, 314, 315, 316, 317, 318, 319; of configuration modules 321, 322, 323, 324, 325, 326; of request modules 331, 332; of retrieval modules 341, 342, 343, 344; of response modules 351, 352, 353, 354, 355, 356, 357, 358, 359; of invocation modules 371, 372, 373, 374; of statement modules 381, 382; of comparators 391; of clocks 392; of expert systems 393; of transmitters 394; of global positioning systems 396; of radio frequency identification (RFID) transponders 397; or of ultrasound identification (USID) transponders 398. In some contexts, moreover, a single component (an application-specific integrated circuit or device-executable software, e.g.) may implement two or more types of the modules described below. Input module 319, for example, may (optionally) be configured to implement more than one of input modules 311-318 (as an automatic response to device-detectable events as described below, e.g.). Response module 359 may likewise be configured to implement more than one of response modules 351-358 (in response to an activation signal from invocation module 374, e.g.). In many of the contexts described below, two or more instances of device 305 are configured to interact with one another or to include one or more media 105 as described below. See FIGS. 4-7, 20, and 21.

Figure 4:
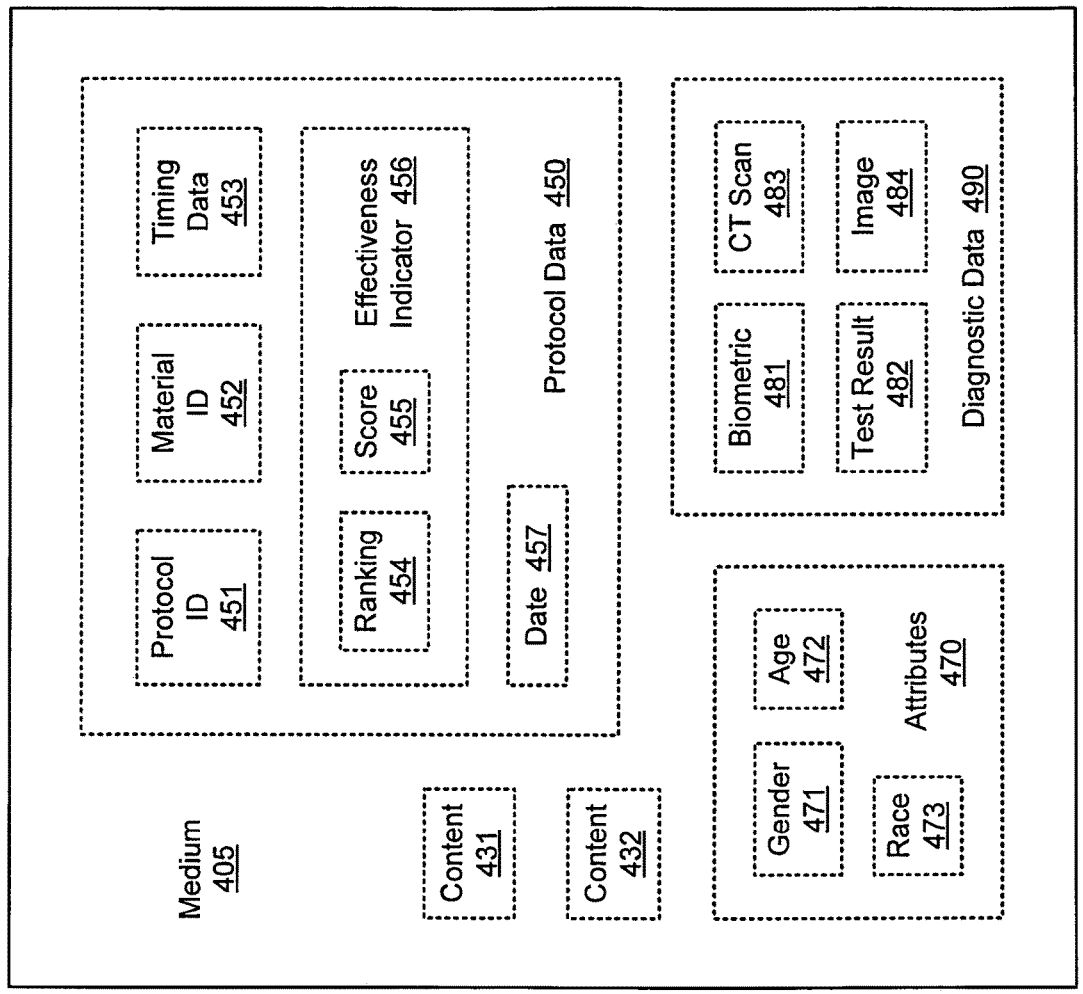
FIGS. 4-7 respectively depict other exemplary environments in which one or more technologies may be implemented in one or more data-handling media.

With reference now to FIG. 4, shown is an example of a system 4 (a network subsystem, e.g.) in which one or more technologies may be implemented. One or more media 405 are configured to bear one or more instances of content 431, 432; of protocol data 450; of patient attributes 470 (gender 471 or age 472 or race 473, e.g.); of biometrics 481, test results 482, computed tomography scans 483 or other images 484; or other such diagnostic data 490. Each of the data components 126-128, 136-138, 146-148 that pertain to a particular patient 292, for example, may (optionally) include one or more protocol identifiers 451, material identifiers 452 (of drugs, e.g.), timing data 453 (of dosages, e.g.), protocol effectiveness indicators 456 (such as rankings 454 or scores 455, e.g.), or dates 457 (of orders or enrollments or injuries or other major events, e.g.) as well as diagnostic data 490 relating to each selected protocol (documenting its rationale or apparent effect, e.g.).

Figure 5:
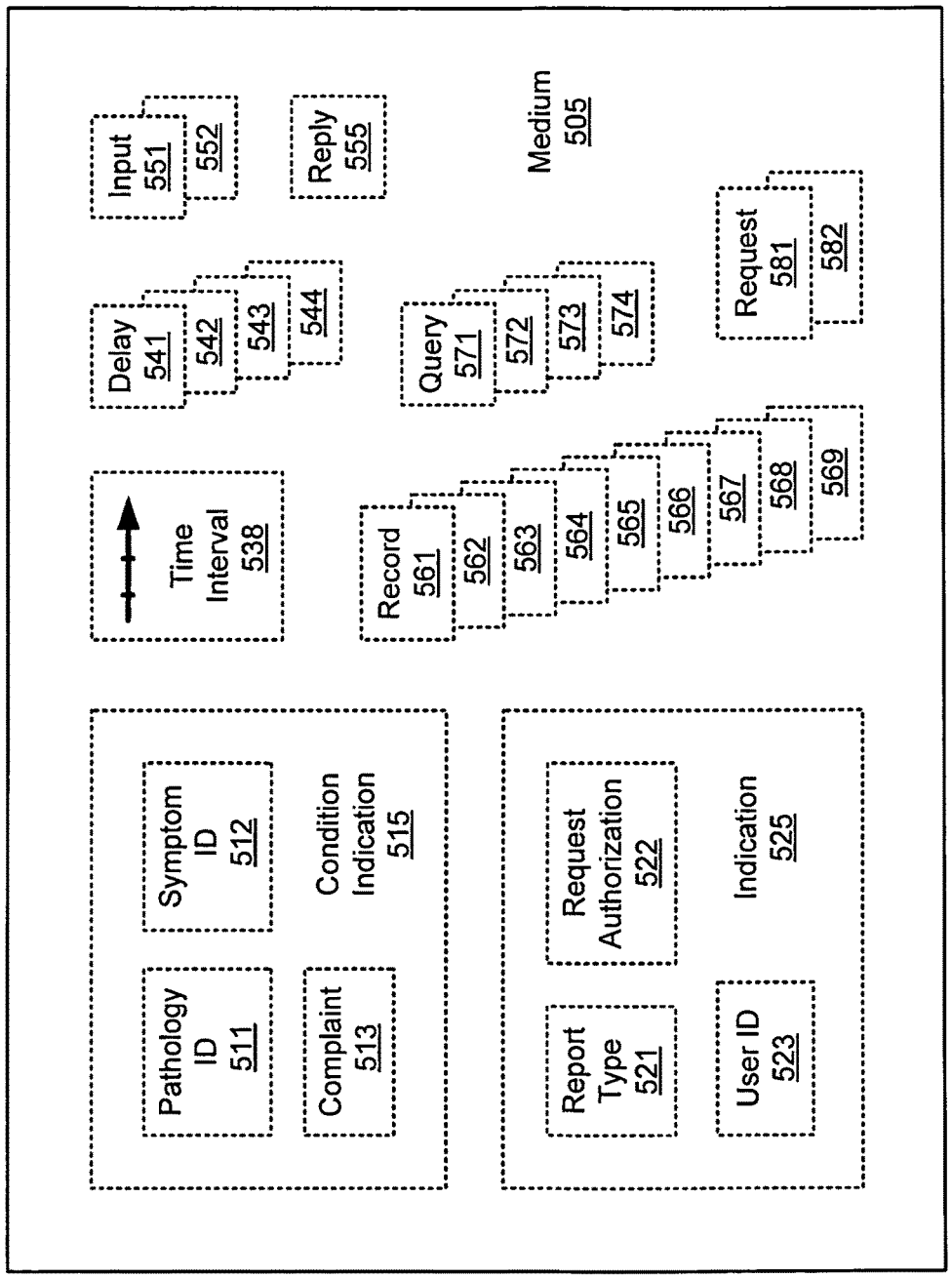

With reference now to FIG. 5, shown is an example of a system 5 (a network subsystem, e.g.) in which one or more technologies may be implemented. One or more media 505 are configured to bear one or more instances of pathology identifiers 511, symptom identifiers 512, complaints 513, or other such condition indications 515; of report types 521, request authorizations 522, user identifiers 523, or other such indications 525 (of excessive institutional readmissions or other apparently negative outcomes that warrant scrutiny, e.g.); of time intervals 538 or programmatic delays 541, 542, 543, 544; of inputs 551, 552 or replies 555; of records 561, 562, 563, 564, 565, 566, 567, 568, 569 relating to a particular patient or caregiver; of queries 571, 572, 573, 574 or requests 581, 582 as described below.

Figure 6:
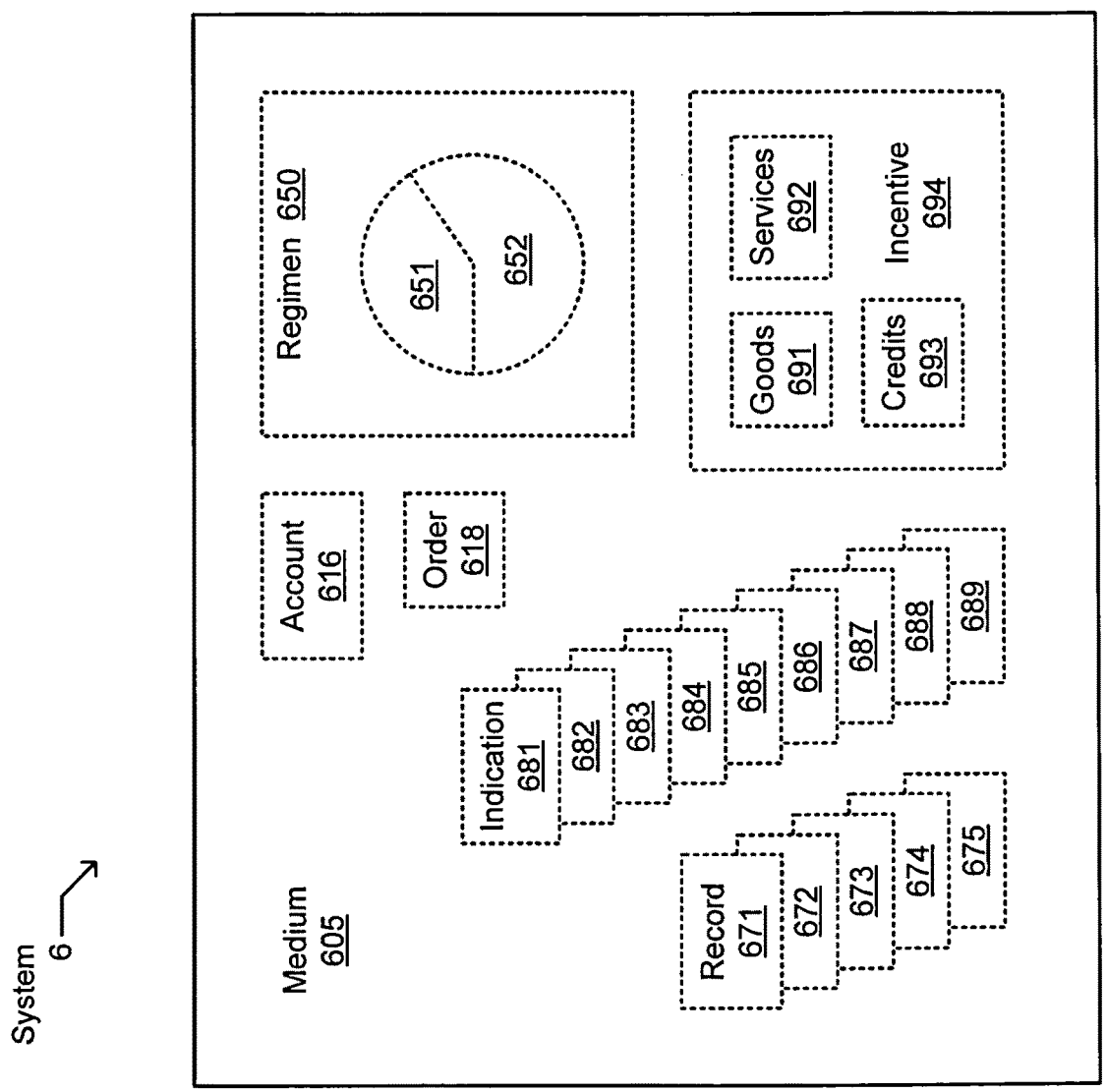

With reference now to FIG. 6, shown is an example of a system 6 (a network subsystem, e.g.) in which one or more technologies may be implemented. One or more media 605 are configured to bear one or more instances of accounts 616 (relating to funds or other inventories, e.g.); orders 618 (by a physician, e.g.); components 651, 652 of a regimen 650; records 671, 672, 673, 674, 675 relating to a particular patient or caregiver; indications 681, 682, 683, 684, 685, 686, 687, 688, 689 of various events or conditions relating to healthcare or information management; or of goods 691, services 692, credits 693, or other incentives 694 as described below.

Figure 7:
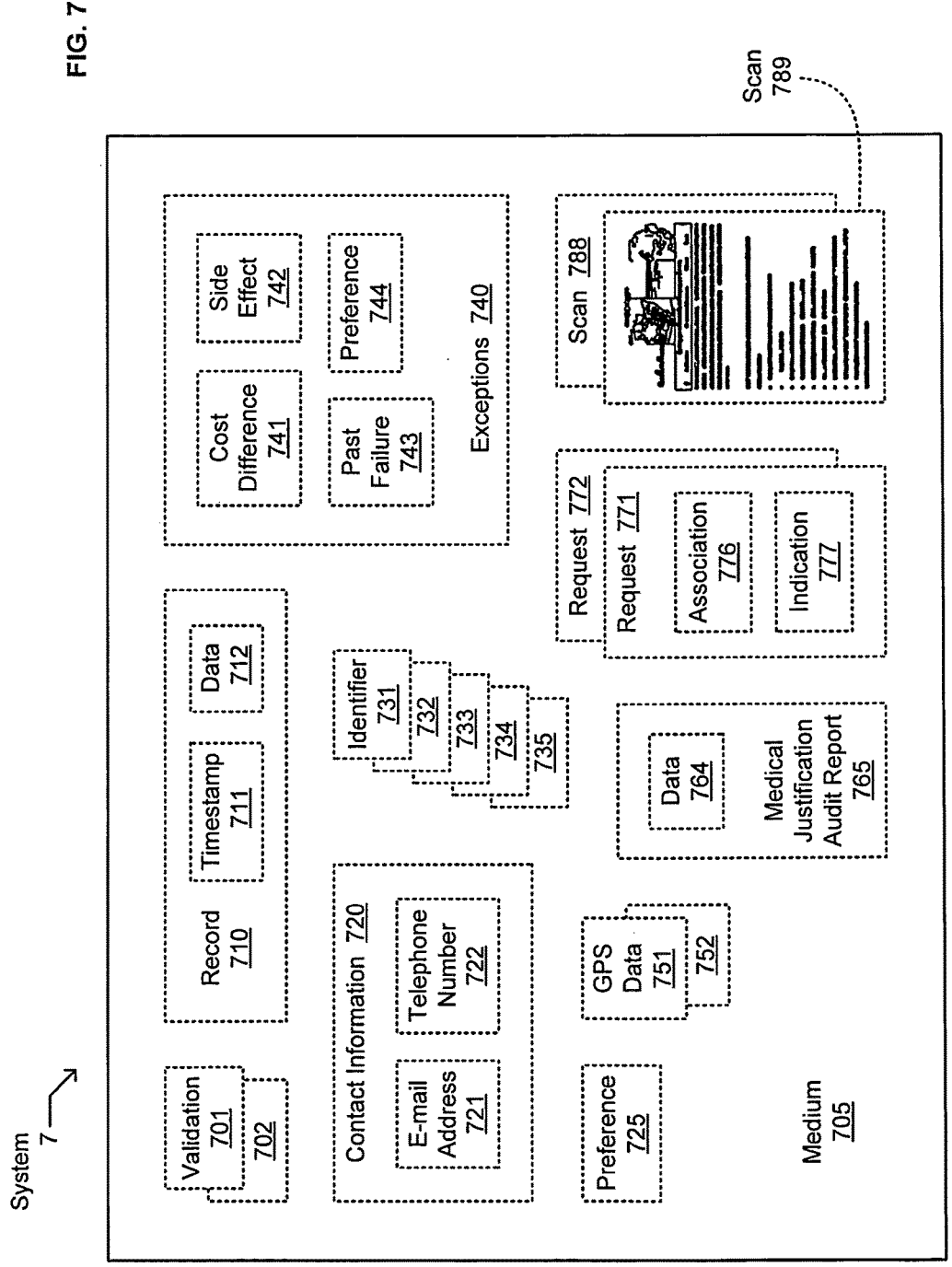

With reference now to FIG. 7, shown is an example of a system 7 (a network subsystem, e.g.) in which one or more technologies may be implemented. One or more media 705 are configured to bear one or more instances of validations 701, 702; records 710 (comprising timestamps 711 or other data 712 manifesting measurement or observation events, e.g.); e-mail addresses 721, telephone numbers 722, or other contact information 720 (of a care provider or administrator, e.g.); preferences 725 (of users of devices 305 as described below, e.g.); identifiers 731, 732, 733, 734, 735 (of devices or individuals, e.g.); coded or other digitally expressed exceptions 740 affecting treatment decisions (cost differences 741, side effects 742, past failures 743, or patient preferences 744, e.g.); global positioning system (GPS) data 751, 752 (of devices or individuals as described below, e.g.); data 764 comprising medical justification audit reports 765; indications 777 comprising requests 771, 772 (signaling an association 776 between a caregiver or patient and various indications 681-689 described below, e.g.); and scans 788, 789 (of documents supporting a course of treatment, e.g.).

Several variants described herein refer to device-detectable "implementations" such as one or more instances of computer-readable code, transistor or latch connectivity layouts or other geometric expressions of logical elements, firmware or software expressions of transfer functions implementing computational specifications, digital expressions of truth tables, or the like. Such instances can, in some implementations, include source code or other human-readable portions. Alternatively or additionally, functions of implementations described herein may constitute one or more device-detectable outputs such as decisions, manifestations, side effects, results, coding or other expressions, displayable images, data files, data associations, statistical correlations, streaming signals, intensity levels, frequencies or other measurable attributes, packets or other encoded expressions, or the like from invoking or monitoring the implementation as described herein.

In some embodiments, a "state" of a component may comprise "available" or some other such state-descriptive labels, an event count or other such memory values, a partial depletion or other such physical property of a supply device, a voltage, or any other such conditions or attributes that may change between two or more possible values irrespective of device location. Such states may be received directly as a measurement or other detection, in some variants, and/or may be inferred from a component's behavior over time. A distributed or other composite system may comprise vector-valued device states, moreover, which may affect dispensations or departures in various ways as exemplified herein.

"Received," "particular," "wearable," "portable," "precedent," "stationary," "audible," "conditional," "explicit," "prior," "extrinsic," "mobile," "specific," "partly," "local," "between," "passive," "associated," "effective," "single," "wireless," "any," "within," "automatic," "proximate," "remote," "common," "selective," "explicit," "resident," "employed," "detectable," "multiple," "in a vicinity," "affirmative," or other such descriptors herein are used in their normal yes-or-no sense, not as terms of degree, unless context dictates otherwise. In light of the present disclosure those skilled in the art will understand from context what is meant by "vicinity," by being "in" or "at" a detection region, by "remote," and by other such positional descriptors used herein. "For" is not used to articulate a mere intended purpose in phrases like "circuitry for" or "instruction for," moreover, but is used normally, in descriptively identifying special purpose circuitry or code.

In some embodiments, "signaling" something can include identifying, contacting, requesting, selecting, or indicating the thing. In some cases a signaled thing is susceptible to fewer than all of these aspects, of course, such as a task definition that cannot be "contacted."

In some embodiments, "status indicative" data can reflect a trend or other time-dependent phenomenon indicating some aspect of a subject's condition. Alternatively or additionally, a status indicative data set can include portions that have no bearing upon such status. Although some types of distillations can require authority or substantial expertise (e.g. making a final decision upon a risky procedure or other course of treatment), many other types of distillations can readily be implemented without undue experimentation in light of teachings herein.

In some embodiments, "causing" events can include triggering, producing or otherwise directly or indirectly bringing the events to pass. This can include causing the events remotely, concurrently, partially, or otherwise as a "cause in fact," whether or not a more immediate cause also exists.

Some descriptions herein refer to an "indication whether" an event has occurred. An indication is "positive" if it indicates that the event has occurred, irrespective of its numerical sign or lack thereof. Whether positive or negative, such indications may be weak (i.e. slightly probative), definitive, or many levels in between. In some cases the "indication" may include a portion that is indeterminate, such as an irrelevant portion of a useful photograph.

Figure 8:
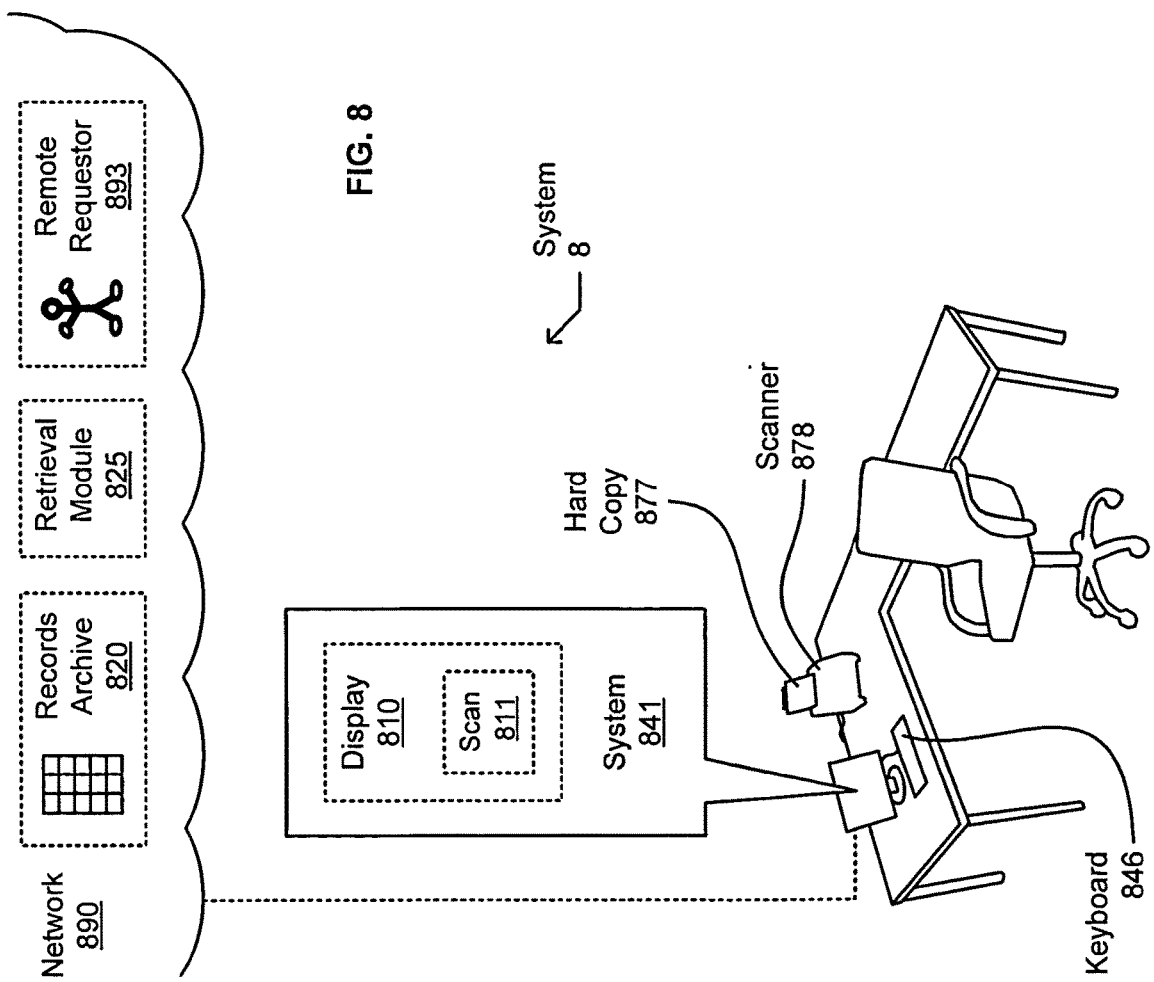

With reference now to FIG. 8, shown is an example of a system 8 (a subsystem of one or more networks 290, 890 described herein, e.g.) in which one or more technologies may be implemented. A desktop scanner 878 is configured to transmit a scan 811 of a hardcopy 877 (of a medical journal article, e.g.) to a local system 841 (comprising a display 810 and keyboard 846, e.g.) on one or more networks 290, 890 described herein. One such network 890 comprises a records archive 820 accessible by one or more retrieval modules 825 operable by a remote requestor 893 (remote from local system 841, e.g.).

Figure 14:
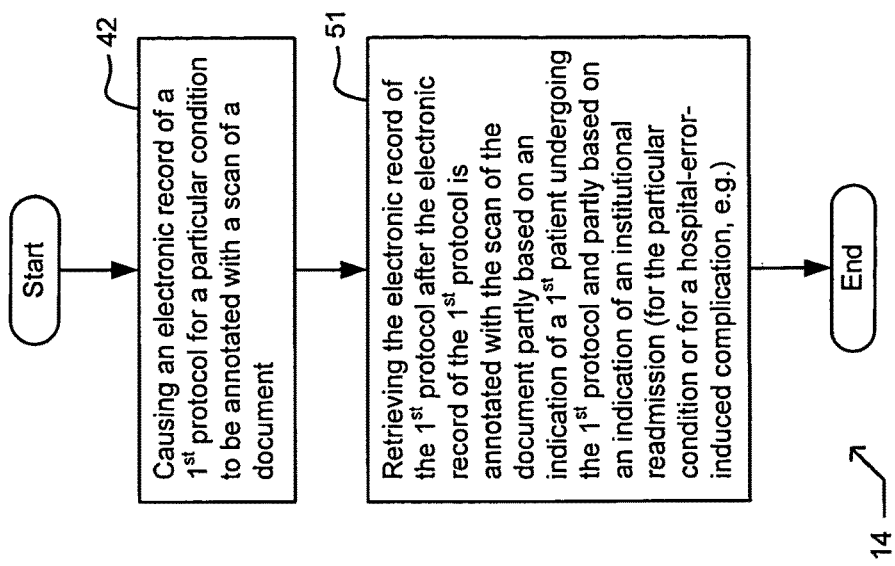
FIG. 14 depicts a high-level logic flow of an operational process described with reference to FIG. 8.

With reference now to FIG. 14, shown is a high-level logic flow 14 of an operational process. Intensive operation 42 describes causing an electronic record of a first protocol for a particular condition to be annotated with a scan of a document (e.g. configuration module 326 amending a digital record 569 of the first protocol to include a reference to or a copy of a digital scan 811 of a hard copy 877 in response to input module 314 receiving the reference to or the copy of the digital scan 811). This can occur, for example, in a context in which record 569 reflects patient 292 being admitted or having been admitted to hospital 201 for the treatment of a particular condition 170 by a specific protocol 120, in which network 290 is linked to network 890, in which one or more instances of device 305 reside on network 890 (implementing a computer workstation comprising system 841, e.g.), in which one or more input modules 311-319 receive the digital scan 811 as an automatic response to scanner 878 receiving the hard copy 877, and in which configuration module 326 fully implements the annotation (directly to a remote instance of record 569, e.g.) without any manual input (as an additional automatic response to scanner 878 receiving the hard copy 877, e.g.). Alternatively, input module 314 may be configured to confirm that a caregiver wants such annotation or to permit the caregiver to tune the annotation (by adding related notes or orders or by annotating other records 561-569 with the same scan 811, e.g.). In some variants, for example, the local user can confirm that the changes made to a local instance of record 569 (including a locally indicated or displayed scan 811, e.g.) should be written to a remote records archive 820 (into a data component 127 specifically associated with the protocol 120 and with the condition 170, e.g.) by responding affirmatively to a query 572 like "save changes to the current record?"

In light of teachings herein, numerous existing techniques may be applied for configuring special-purpose circuitry or other structures effective for annotating an electronic record as described herein without undue experimentation. See, e.g., U.S. Pat. No. 7,941,009 ("Real-time computerized annotation of pictures"); U.S. Pat. No. 7,913,162 ("System and method for collaborative annotation using a digital pen"); U.S. Pat. No. 7,847,970 ("System and method for reception analysis and annotation of prescription data"); U.S. Pat. No. 7,546,524 ("Electronic input device system and method using human-comprehensible content to automatically correlate an annotation of a paper document with a digital version of the document"); U.S. Pat. No. 7,373,342 ("Including annotation data with disparate relational data"); U.S. Pat. No. 7,286,894 ("Hand-held computer device and method for interactive data acquisition analysis annotation and calibration"); U.S. Pat. No. 7,269,787 ("Multi-document context aware annotation system"); U.S. Pat. No. 7,263,493 ("Delivering electronic versions of supporting documents associated with an insurance claim"); U.S. Pat. No. 6,839,403 ("Generation and distribution of annotation overlays of digital X-ray images for security systems"); U.S. Pat. No. 6,721,921 ("Method and system for annotating documents using an independent annotation repository"); U.S. Pat. No. 6,594,519 ("Distributed real time catalog-based annotation and documentation system for cardiology procedures"); U.S. Pat. No. 6,575,901 ("Distributed real time replication-based annotation and documentation system for cardiology procedures"); U.S. Pat. No. 6,397,181 ("Method and apparatus for voice annotation and retrieval of multimedia data").

Extensive operation 51 describes retrieving the electronic record of the first protocol after the electronic record of the first protocol is annotated with the scan of the document partly based on an indication of a first patient undergoing the first protocol and partly based on an indication of an institutional readmission (e.g. retrieval module 825 retrieving record 569 based on indications that patient 292 was treated for the particular condition 170 at hospital 201 and was released and later readmitted for the same condition 170). This can occur, for example, in a context in which record 569 includes a symptom identifier 512 or other indication 681 of the specific medical condition 170, in which record 569 also includes a color scan 811 of content 431 pertaining to the medical condition 170 presented in the form of a hard copy 877 (a research study provided by the patient 292 or a family member, e.g.), and in which such later readmission (for the particular condition or for a treatment of some harm to the patient resulting from a medical error that occurred during the prior hospitalization, e.g.) would otherwise trigger a reduction in payment for the "first" protocol or for other hospital services. In some contexts, for example, a Multidrug-Resistant Staphylococcus Aureus (MRSA) diagnosis that appears during a patient's hospital stay, or some other hospital-acquired condition, may be indicative of such medical error. Alternatively or additionally, such content 431 (in one or more media 105, 405 residing on network 890, e.g.) may pertain to one or more medical protocols 120, 130 under prospective consideration for treating the patient 292 and may be retained (as evidence of diligent decision-making or of why a course of treatment was not selected, e.g.).

In light of teachings herein, numerous existing techniques may be applied for configuring special-purpose circuitry or other structures effective for determining which patients have been treated or hospitalized for a particular condition as described herein without undue experimentation. See, e.g., U.S. Pat. No. 7,996,074 ("System and method for providing closely-followed cardiac therapy management through automated patient care"); U.S. Pat. No. 7,991,485 ("System and method for obtaining, processing and evaluating patient information for diagnosing disease and selecting treatment"); U.S. Pat. No. 7,942,817 ("Patient monitoring and treatment medical signal interface system"); U.S. Pat. No. 7,827,043 ("Method using a global server for providing patient medical histories to assist in the delivery of emergency medical services"); U.S. Pat. No. 7,698,154 ("Patient-controlled automated medical record, diagnosis, and treatment system and method"); U.S. Pat. No. 7,395,216 ("Using predictive models to continuously update a treatment plan for a patient in a health care location"); U.S. Pat. No. 7,395,214 ("Apparatus, device and method for prescribing, administering and monitoring a treatment regimen for a patient"); U.S. Pat. No. 7,204,805 ("Patient conditional diagnosis, assessment and symptom tracking system"); U.S. Pat. No. 7,069,085 ("Method and apparatus to produce, maintain and report information related to patient treatment using medical devices"); U.S. Pat. No. 6,726,634 ("System and method for determining a condition of a patient"); U.S. Pat. No. 6,405,165 ("Medical workstation for treating a patient with a voice recording arrangement for preparing a physician's report during treatment"); and U.S. Pat. No. 6,338,039 ("Method for automated collection of psychotherapy patient information and generating reports and treatment plans").

With reference now to FIG. 9, shown is an example of a system 9 (e.g. a subsystem of one or more networks 290, 990) in which one or more technologies may be implemented. A desktop system 941 is configured to display (to a caregiver 991 or other authorized entity, e.g.) one or more instances of studies 931, records 932, forms 933, or other such indications relating to a patient 992. Such records 932 may include various data components 127, 136, 148 relating to therapies (actually or potentially) being performed upon one or more patients 292, 992 as described herein. In some contexts, one or more such records 932 may be retrieved from or saved to records archive 920 (by one or more retrieval modules 925 in an implementation of device 305 described above, e.g.). Alternatively or additionally, a regional network 990 (e.g. for one or more hospitals 201, 202) containing such archives may be accessed (by a remote requestor 993, e.g.) as described herein.

With reference now to FIG. 15, shown is a high-level logic flow 15 of an operational process. Intensive operation 35 describes obtaining an indication that a particular condition was treated in a first patient with a first protocol (e.g. input module 316 receiving a medical record 932 or other specific indication 935 that protocol 120 was used for treating condition 170 in patient 292). This can occur, for example, in a context in which one or more such indications 935 comprise a data component 127 associated with protocol 120 and with condition 170, in which a second patient 992 or her caregiver 991 has access to some or all of the data component 127 (including the specific indication 935, e.g.), and in which condition 170 is described in data component 127 with a pathology identifier 511 ("fibromyalgia," e.g.) that has also been assigned to the "second" patient 992. In some variants, for example, one or more such data components 126-128, 136-138 may reside in one or more regional records archives 820, 920 accessible to authorized caregivers 991. Alternatively or additionally, one or more such indications 935 may be obtained from a published research study 931 (as a hard copy 877 to be scanned, e.g.) or entered into an online form 933 (with an identifier of a hospital 201 or a physician or protocol data 450 or other background information known to caregiver 991 about the "first" patient 292 or his/her prior treatment, e.g.).

In light of teachings herein, numerous existing techniques may be applied for configuring special-purpose circuitry or other structures effective for extracting an indication that a patient (mammal, e.g.) was treated for a particular condition as described herein without undue experimentation. See, e.g., U.S. Pat. No. 8,073,711 ("Method and system for obtaining health-related records and documents using an online location"); U.S. Pat. No. 8,065,347 ("Managing protocol amendments in electronically recorded clinical trials"); U.S. Pat. No. 7,972,274 ("System and method for analyzing a patient status for congestive heart failure for use in automated patient care"); U.S. Pat. No. 7,935,055 ("System and method of measuring disease severity of a patient before, during and after treatment"); U.S. Pat. No. 7,899,764 ("Medical ontologies for machine learning and decision support"); U.S. Pat. No. 7,552,039 ("Method for sample processing and integrated reporting of dog health diagnosis"); U.S. Pat. No. 7,533,353 ("Electronic system for collecting and automatically populating clinical order information in an acute care setting"); and U.S. Pat. No. 7,069,085 ("Method and apparatus to produce, maintain and report information related to patient treatment using medical devices").

Intensive operation 43 describes causing a record of a second patient to include the indication that the particular condition was treated in the first patient with the first protocol (e.g. configuration module 323 modifying a medical record 562 of the "second" patient 992 by including one or more specific indications 935 that protocol 120 was used for treating condition 170 in one or more prior patients 292, with or without identifying any particular "first" patient 292). This can occur, for example, in a context in which protocol 120 is not yet established as the preferred treatment for treating condition 170; in which the "first" and "second" patients have one or more attributes 470 (gender 471 or general age 472 or race 473, e.g.) in common; in which record 562 identifies one or more such attributes 470 but does not include other information that identifies the "first" patient 292. In addition to such considerations relating to patient privacy, tracking such information may be helpful in relation to other regulatory considerations. Under the healthcare system in the United States, for example, Section 4302 of Public Law 111-148 (the "Patient Protection and Affordable Care Act," sometimes called "Obamacare") "[r]equires federally conducted or supported healthcare programs or surveys to collect and report demographic data, including ethnicity, sex, primary language, and disability status, as well as data at the smallest geographic level possible, such as state or local, etc."

Referring again to FIGS. 1 & 9, moreover, in some contexts a caregiver 991 may determine a circumstance of the "second" patient falls into one or more identifiable exceptions 740 to a general practice of treating condition 170 with a more conventional protocol 140. In a context in which the conventional protocol 140 is characterized by one or more generally preferred drugs 141 and associated dosages 142, practice groups or facilities or modes (in-patient at hospital 201, e.g.), or frequencies of treatment (daily or weekly, e.g.), an unconventional protocol 120 may be warranted for one or more reasons of cost difference 741 (protocol 140 being too expensive for continued use, e.g.); side effects 742 (an allergy to drug 141 or drug interaction risk, e.g.); past failure 743 (having been ineffective for treating condition 170 in patient 992, e.g.); or a documented preference 744 (manifested by a waiver from "second" patient 992, e.g.). In some variants, therefore, it may be preferable for configuration module 323 to be operable for modifying medical record 562 to include such exceptions 740 in circumstance (optionally by querying caregiver 991 for such information, e.g.).

Extensive operation 52 describes retrieving the record of the second patient selectively in response to an association between the second patient and an indication of an institutional readmission after the record of the second patient includes the indication that the particular condition was treated in the first patient with the first protocol (e.g. retrieval module 925 requesting and providing medical record 562 in response to a remote requestor 993 initiating a medical justification audit report 765 indicating that the "second" patient 992 underwent multiple in-patient treatments for condition 170 during separate hospital stays). This can occur, for example, in a context in which operations 35 and 43 had both been performed; in which the retrieval is "selective" insofar that each instance of operation 52 retrieves less than all such records 561-569 (of billing, e.g.); in which caregiver 991 has reasonably and correctly relied upon the indication 935 as precedent (that the particular condition 170 was treated in the "first" patient 292 with protocol 120, e.g.) in her decision to recommend or administer protocol 120 to the "second" patient 992 in hospital 201; in which it is not self-evident that such administration was reasonable in the absence of the specific indication 935; and in which protocol 120 is ultimately not permanently effective at eradicating the particular condition 170. In the event that the "second" patient 992 is readmitted to hospital 202 later for further treatment of the particular condition 170 and that such readmission would otherwise trigger a reduction in payment for the services of caregiver 991 or of hospital 201, remembering and reacquiring the particular condition 170 (or some other adequate justification) may become an onerous and crucial task. In some contexts, a medical justification audit report 765 may include data 764 (where available) supporting care decisions made on behalf of many individuals each of whom was readmitted (hospitalized more than once for a particular condition, e.g.). Alternatively or additionally, in some contexts, such an association 776 (between the "second" patient 992 and an indication 777 of apparently-excessive institutional readmissions, e.g.) may be established by an electronic request 771 (received from remote requestor 993 and directly invoking retrieval module 925, e.g.). More generally, such actions taken with reference to one or more criteria are "selective" (as used in FIGS. 24-27 below, e.g.) if at least one of the criteria is used as a determinant in deciding which data components (records, e.g.) will not be included in or affected by the action.

Figure 10:
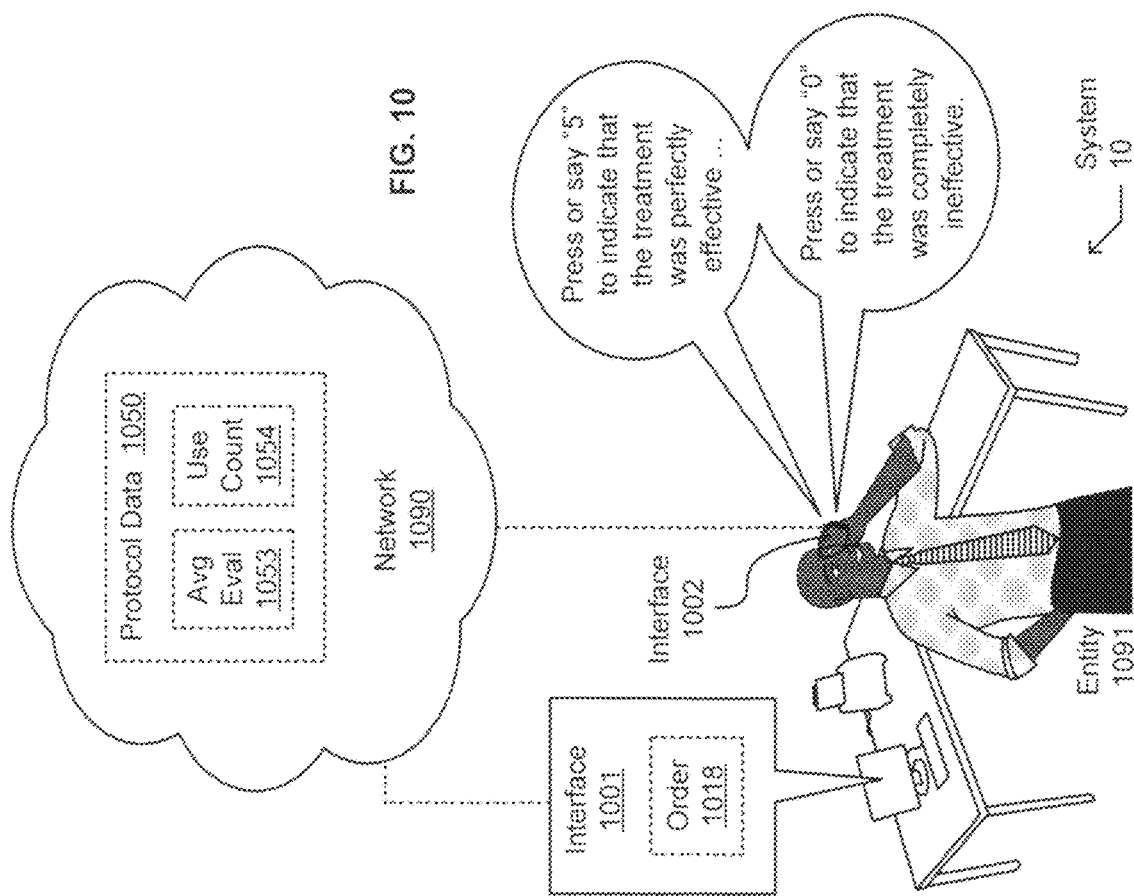

With reference now to FIG. 10, shown is an example of a system 10 in which one or more technologies may be implemented. One interface 1001 (e.g. a desktop system 841, 941) is configured for use (e.g. by a physician, administrator, or other authorized entity 1091) in entering and transmitting an order 1018 or other such content (of a protocol 130 or condition 170, e.g.) via one or more networks 1090 as described above. The one or more networks 1090 are also configured to contact entity 1091 (using contact information 720 for the same interface 1001 or another interface 1002 associated with the same entity 1091, e.g.) under some conditions as described herein, such as to request an indication of the effectiveness of a treatment (protocol 130, e.g.) that the entity might have tried or witnessed recently. In some contexts, this permits protocol data 1090 (average evaluations 1053 or use counts 1054, e.g.) to be generated or updated (on various instance of media 105, 405, 505, 605, 705 in network 1050, e.g.).

Figure 16:
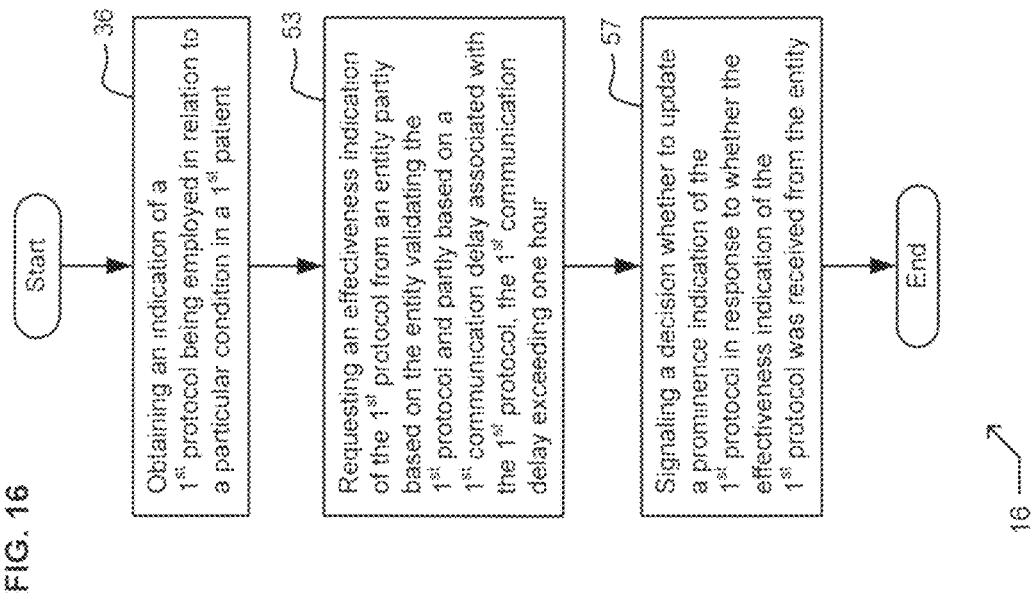
FIG. 16 depicts a high-level logic flow of an operational process described with reference to FIG. 10.

With reference now to FIG. 16, shown is a high-level logic flow 16 of an operational process. Intensive operation 36 describes obtaining an indication of a first protocol being employed in relation to a particular condition in a first patient (e.g. input module 313 receiving a record 564 indicating that an order 1018 was placed for a particular drug 141 or protocol 140 prescribed or purchased for the treatment of a particular condition 170 in patient 292). This can occur, for example, in a context in which device 305 includes one or more media 105 (on network 1090, e.g.) bearing an average evaluation 1053, use count 1054, or other such quantified protocol data 1050 as described below (as a data component 147 associated with the particular condition 170 and with the particular drug 141 or protocol 140, e.g.). In some contexts, moreover, input module may receive the indication as an inquiry into the prospect of treating condition 170 with one or more protocols 130, 140 and may record such inquiries in record 564. Alternatively or additionally, input module 313 and request module 332 may be configured to perform operation 36 jointly by initiating communication with someone generally familiar with the protocol 140 (a nurse or pharmacist who can administer the particular drug 141 or protocol 140, e.g.).

In light of teachings herein, numerous existing techniques may be applied for configuring special-purpose circuitry or other structures effective for motivating or monitoring voluntary participation in information management protocols as described herein without undue experimentation. See, e.g., U.S. Pat. No. 8,056,118 ("Systems and methods for universal enhanced log-in, identity document verification, and dedicated survey participation"); U.S. Pat. No. 7,828,554 ("System for delivering an educational program to a remote site and for monitoring participation therein"); U.S. Pat. No. 6,807,532 ("Method of soliciting a user to input survey data at an electronic commerce terminal"); and U.S. patent application Ser. No. 13/066,442 ("Cost-effective resource apportionment technologies suitable for facilitating therapies").

Extensive operation 53 describes requesting an effectiveness indication of the first protocol from an entity partly based on the entity validating the first protocol and partly based on a first communication delay associated with the first protocol, the first communication delay exceeding one hour (e.g. request module 331 asking one or more entities 1091 who validated the particular protocol for an effectiveness indicator 456 signaling how effective the particular protocol was for the treatment of condition 170 in patient 292). This can occur, for example, in a context in which an entity 1091 signals one or more validations 701, 702 of the treatment by prescribing, purchasing, administering, or authorizing the particular drug 141 or protocol 140 for the treatment of condition 170 in patient 292 and in which one or more data components 127, 137, 147 define respective communication delays 542, 543, 544 so that request module 331 transmits a query (by telephone or e-mail, e.g.) to the entity 1091 (practitioner or patient, e.g.) only after the treatment has probably failed or started to work. In a context in which a 10-day course of an antibiotic (as protocol 130, e.g.) would be expected to alleviate a fever (as condition 160, e.g.) in a few hours or days, for example, a corresponding communication delay 543 of about 5 days (within an order of magnitude, e.g.) will be appropriate for obtaining a score 455 (on a 0-5 scale, e.g.) or other effectiveness indicator 456 as a delayed automatic response to the ordering or administration of the antibiotic. In less urgent contexts, moreover, an expected delivery time (in hours or days, e.g.) may be included for some of the communication delays 541-544 (those for which a drug 141 or other material component of a protocol 140 is delivered to a patient's home 289, e.g.). Alternatively or additionally, request module 331 may be configured to send the same request to a particular entity 1091 via more than one interface 1001, 1002 (using both an e-mail address 721 and a telephone number 722 associated with a single identified entity 1091, e.g.).

In light of teachings herein, numerous existing techniques may be applied for configuring special-purpose circuitry or other structures effective for transmitting queries or other information requests as described herein without undue experimentation. See, e.g., U.S. Pat. No. 8,073,013 ("Method and apparatus for collecting survey data via the internet"); U.S. Pat. No. 7,962,359 ("Method and system for collecting and disseminating survey data over the internet"); U.S. Pat. No. 7,836,073 ("Method and system for transmitting pre-formulated query to database"); U.S. Pat. No. 7,590,547 ("Method for transmitting an anonymous request from a consumer to a content or service provider through a telecommunication network"); U.S. Pat. No. 7,529,214 ("Mobile node for transmitting a request for information which specifies a transfer device to be used"); U.S. Pat. No. 6,807,532 ("Method of soliciting a user to input survey data at an electronic commerce terminal"); and U.S. Pat. No. 6,513,014 ("Method and apparatus for administering a survey via a television transmission network").

Extensive operation 57 describes signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol (e.g. statement module 382 incrementing a use count 1054 in response to receiving a Facebook-style "like" signal from a patient 292 who used the protocol). This can occur, for example, in a context in which the patient 292 was the "entity" contacted in operation 53 (via contact information 720, e.g.); in which the patient 292 was sent a request for such a "like" signal after protocol 140 had enough time (to fail or start working, e.g.), in which a total count of such "like" signals is a "prominence indication" (of protocol 140, e.g.), in which the communication delay and the "first" patient's identity are recorded but not published, and in which a new best practice could not otherwise win widespread recognition within a year of someone devising the practice. In some contexts, for example, a nurse or other care provider familiar with one or more protocols 120, 130 (as they apply to condition 160, e.g.) can designate one or more corresponding delays (based on a success, when a difference is typically seen, or on a side effect onset or other symptom change distribution, e.g.). In a context in which protocol 120 comprises a spinal fusion, for example, a corresponding delay 2126 may be between 6 and 12 months. (See FIG. 21.) In a context in which protocol 130 comprises administering an antihypertensive (for condition 170, e.g.), a corresponding delay 2137 may be on the order of 1.0 months (within an order of magnitude, e.g.). Alternatively or additionally, statement module 382 may perform operation 57 by transmitting an average evaluation 1053 computed based on effectiveness-indicative numerical scores 455 received from each of several entities 1091. This can occur, for example, in a context in which multiple entities have each responded to a corresponding query 573 (like "We need to know how effective you thought this treatment was on a zero-to-five scale . . . please press or say '5' to indicate that the treatment was perfectly effective . . . please press or say '0' to indicate that the treatment was completely ineffective," e.g.) transmitted by request module 331 and in which such an average (as a rolling or inception-to-date average, e.g.) is a "prominence indication" of the treatment or other protocol.

In light of teachings herein, numerous existing techniques may be applied for configuring special-purpose circuitry or other structures effective for calculating and disseminating prominence indications as described herein without undue experimentation. See, e.g., U.S. Pat. No. 8,078,606 ("Rank-based estimate of relevance values"); U.S. Pat. No. 8,069,080 ("Methods for generating healthcare provider quality and cost rating data"); U.S. Pat. No. 8,065,669 ("Apparatus for automatically converting numeric data to a processor efficient format for performing arithmetic operations"); U.S. Pat. No. 8,046,371 ("Scoring local search results based on location prominence"); U.S. Pat. No. 7,949,643 ("Method and apparatus for rating user generated content in search results"); U.S. Pat. No. 7,865,171 ("Method and system for rating notification"); U.S. Pat. No. 7,826,965 ("Systems and methods for determining a relevance rank for a point of interest"); U.S. Pat. No. 7,730,005 ("Issue tracking system using a criteria rating matrix and workflow notification"); U.S. Pat. No. 7,630,913 ("Automated processing of medical data for disability rating determinations"); and U.S. Pat. No. 6,832,245 ("System and method for analyzing communications of user messages to rank users and contacts based on message content").

Figure 11:
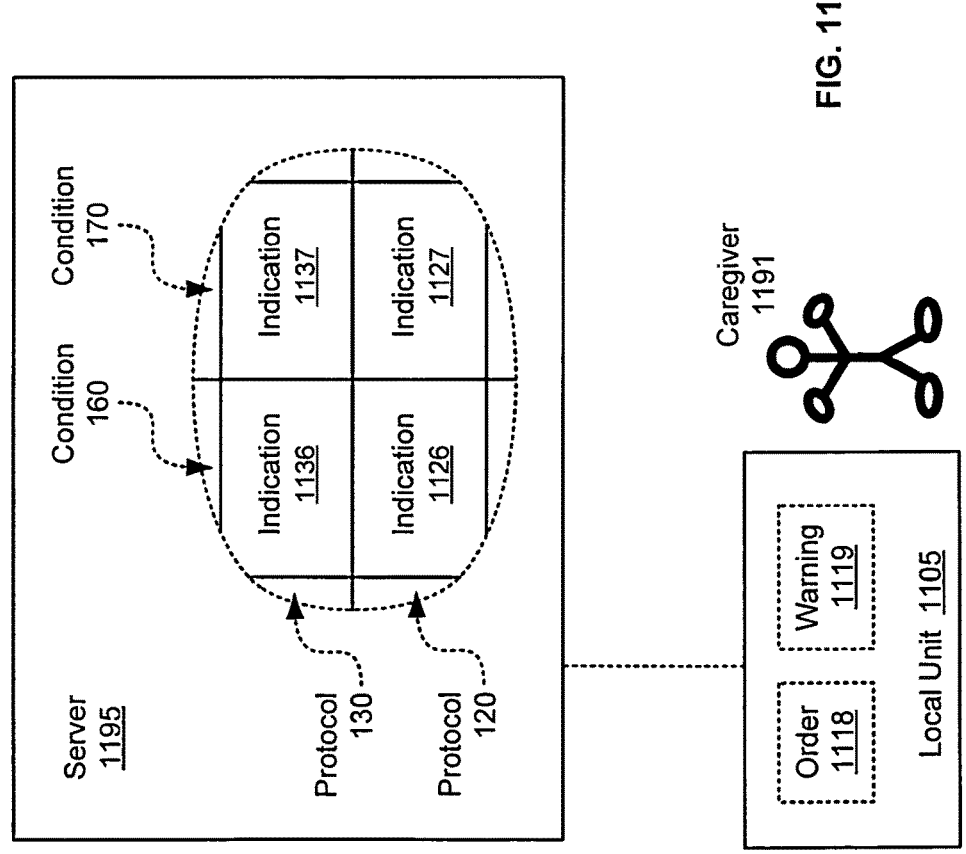

With reference now to FIG. 11, shown is an example of a system 11 (a subsystem of one or more networks described above, e.g.) in which one or more technologies may be implemented. A local unit 1105 owned or used by a caregiver 1191 may be configured to receive one or more orders 1018, 1118 or other indications 1126, 1127, 1136, 1137 each comprising corresponding data components 126, 127, 136, 137 that each relate to a corresponding specific combination of a condition 160, 170 and protocol 120, 130 for its treatment, as shown. In some contexts, one or more servers 1195 (residing in networks described herein, e.g.) or local circuitry may provide selective feedback (one or more warnings 1119, e.g.) relating to some such combinations (selected by caregiver 1191, e.g.).

Figure 17:
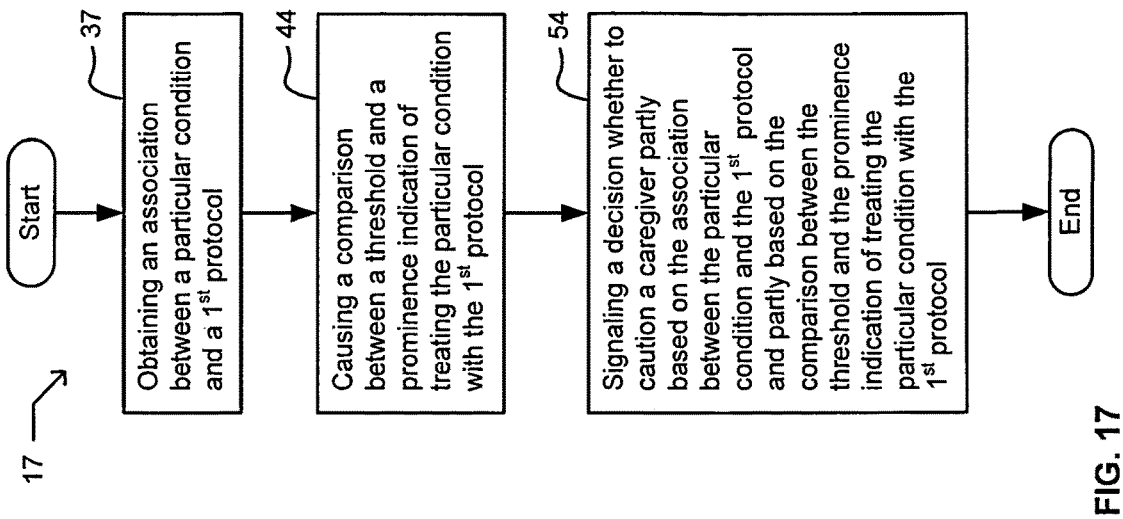
FIG. 17 depicts a high-level logic flow of an operational process described with reference to FIG. 11.

With reference now to FIG. 17, shown is a high-level logic flow 17 of an operational process. Intensive operation 37 describes obtaining an association between a particular condition and a first protocol (e.g. input module 311 receiving a record 563 indicating that an order 1118 was placed for a particular drug or protocol 130 prescribed or purchased for the treatment of a particular condition 160). This can occur, for example, in a context in which the protocol 130 includes administering prednisone daily by ingestion and in which the particular condition 160 is Bell's palsy, bone pain, carpal tunnel syndrome, muscular dystrophy, pulmonary fibrosis, or certain other off-label uses of prednisone. In some contexts, moreover, such protocols 120, 130, 140 may include other drugs or non-medicinal components (physical therapy or surgery, e.g.). Moreover input module 311 may, in some variants, be configured to be invoked by one or more queries 571-574 or other structured dialogs (permitting an expert system 393 to interact with a physician or other caregiver 1191 via local unit 1105, e.g.).

In light of teachings herein, numerous existing techniques may be applied for configuring special-purpose circuitry or other structures effective for searching for therapies or conditions that may apply to a patient as described herein without undue experimentation. See, e.g., U.S. Pat. No. 8,008,285 ("Droxidopa and pharmaceutical composition thereof for the treatment of fibromyalgia"); U.S. Pat. No. 8,005,687 ("System, method and computer program product for estimating medical costs"); U.S. Pat. No. 7,979,289 ("System and method for intelligent management of medical care"); U.S. Pat. No. 7,860,552 ("CNS assay for prediction of therapeutic efficacy for neuropathic pain and other functional illnesses"); U.S. Pat. No. 7,797,145 ("Animal health diagnostics"); U.S. Pat. No. 7,552,039 ("Method for sample processing and integrated reporting of dog health diagnosis"); U.S. Pat. No. 7,490,048 ("Apparatus and method for processing and/or for providing healthcare information and/or healthcare-related information"); U.S. Pat. No. 7,346,523 ("Processing an insurance claim using electronic versions of supporting documents"); U.S. Pat. No. 6,704,595 ("Automated method for diagnosing and monitoring the outcomes of atrial fibrillation"); and U.S. Pat. No. 6,014,626 ("Patient monitoring system including speech recognition capability").

Intensive operation 44 describes causing a comparison between a threshold and a prominence indication of treating the particular condition with the first protocol after the association between the particular condition and the first protocol is obtained (e.g. invocation module 373 triggering comparator 391 to generate an output 195 by comparing a prominence indication 1136 with a threshold 191). This can occur, for example, in a context in which one or more devices 305 (including media 105, 405, 505, 705, e.g.) reside in server 1195 and in which response module 351 selects the threshold 191 according to who initiates the association (as a function of a user identifier 523 of a specific caregiver 1191 or caregiver type, e.g.) or to what condition 160 or protocol 130 has been associated. In some contexts, for example, more esteemed caregivers or less hazardous conditions and protocols may warrant a threshold 192 corresponding to a lower prominence (signaling less scrutiny and more latitude in the caregiver's choice of treatment protocols, e.g.). Alternatively or additionally, invocation module 373 may trigger a comparison implemented in a formula (as a subtraction, e.g.). In some contexts, moreover, a less-prominent protocol may be requested by a patient 292 or warranted by the patient's situation. Alternatively or additionally, invocation module 373 may be configured to trigger a storage operation in which one or more instances of prominence indications 1136; thresholds 191; comparison results; quantifications of reputation or scrutiny or latitude (characterizing caregiver 1191, e.g.); or other output 195 are stored in one or more records 569-569, 671-675 as described herein (e.g. in a data component 136-138, 146-148 relating to an elected protocol 130, 140).

In light of teachings herein, numerous existing techniques may be applied for configuring special-purpose circuitry or other structures effective for selecting and applying thresholds or other criteria as described herein without undue experimentation. See, e.g., U.S. Pat. No. 8,069,236 ("Flow control of events based on threshold, grace period, and event signature"); U.S. Pat. No. 8,061,592 ("Overdraft threshold analysis and decisioning"); U.S. Pat. No. 8,005,685 ("Ranking air travel search results based upon user criteria"); U.S. Pat. No. 7,976,171 ("Projector cooling system with time dependent temperature threshold"); U.S. Pat. No. 7,898,995 ("Dynamic adjustment of inactivity timer threshold for call control transactions"); U.S. Pat. No. 7,894,448 ("Proving that a user profile satisfies selection criteria for targeted data delivery"); U.S. Pat. No. 7,849,398 ("Decision criteria for automated form population"); U.S. Pat. No. 7,742,193 ("Method for inspecting prints identifying differences exceeding a threshold"); U.S. Pat. No. 7,624,447 ("Using threshold lists for worm detection"); U.S. Pat. No. 7,592,859 ("Apparatus to compare an input voltage with a threshold voltage"); and U.S. Pat. No. 7,536,301 ("System and method for implementing real-time adaptive threshold triggering in acoustic detection systems").

Extensive operation 54 describes signaling a decision whether to caution a caregiver partly based on the association between the particular condition and the first protocol and partly based on the comparison between the threshold and the prominence indication of treating the particular condition with the first protocol (e.g. response module 356 transmitting an "obscure treatment option" warning 1119 to caregiver 1191 if the threshold 191 exceeds the prominence indication 1136 and otherwise not transmitting any such warning). This can occur, for example, in a context in which server 1195 is on several networks 290, 890, 990; in which searching various records archives 820, 920 can take several minutes or hours to determine a prominence indication 1136; in which local unit 1105 includes an e-mail or other text message display capability operable to deliver such warnings; in which a hospital 201 or field of practice uses a standard numerical threshold for all prominence indication comparisons; and in which the caregiver 1191 would otherwise select among several protocols 120, 130 for the particular condition(s) 160, 170 without knowing which of them had recently become popular in the caregiver's field of practice. In a context in which higher numerical indications 1126 signify more prominence and in which a threshold is set at 4, for example, such threshold may be met (sufficient to avoid triggering a cautionary message to caregiver 1191, e.g.) by determining either that 4 instances of condition 160 had been treated with protocol 120 (for an implementation incorporating a use count 1054, e.g.) or that one or more entities indicated the effectiveness of treating condition 160 with protocol 120 with an average evaluation of at least 4 (for an implementation incorporating an average evaluation 1053, e.g.). Alternatively or additionally, response module 356 may be configured to implement a conditional decision to caution a caregiver 1191 with one or more of a font effect (a bolding or bright color selectively applied for lower-prominence therapies, e.g.), audible warning 1119 (a tone, e.g.), or modal dialog box (displaying a message like "are you sure you want to order this unconventional treatment?" at local unit 1105 before finalizing order 1118, e.g.).

In light of teachings herein, numerous existing techniques may be applied for configuring special-purpose circuitry or other structures effective for implementing a conditional message as described herein without undue experimentation. See, e.g., U.S. Pat. No. 7,932,837 ("Conditional aircraft cabin warning and signalling system for determining the cabin status"); U.S. Pat. No. 7,002,454 ("System and method for warning an operator of a vehicle if the vehicle is operating in a condition that may result in drive belt failure"); U.S. Pat. No. 6,452,487 ("System and method for warning of a tip over condition in a tractor trailer or tanker"); U.S. Pat. No. 6,437,707 ("Detecting a low performance takeoff condition for aircraft for use with ground proximity warning systems"); U.S. Pat. No. 6,373,392 ("Alert device for providing a warning of a baby's condition which may lead to the onset of SIDS"); U.S. Pat. No. 6,310,556 ("Apparatus and method for detecting a low-battery power condition and generating a user perceptible warning"); U.S. Pat. No. 6,310,554 ("Severe weather detection apparatus and method of detecting and warning of severe weather conditions"); and U.S. Pat. No. 6,211,791 ("Warning system for excessive apparent temperature conditions").

Figure 12:
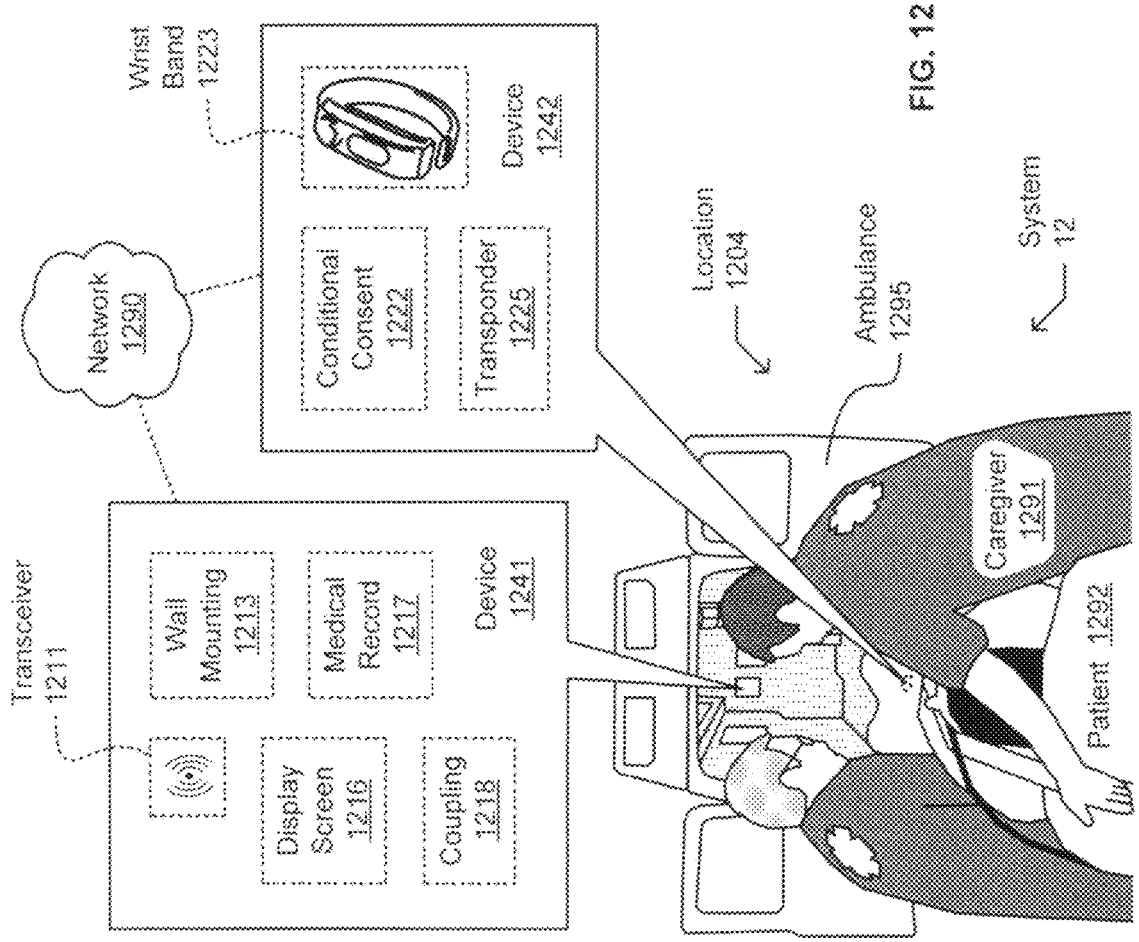

With reference now to FIG. 12, shown is an example of a system 12 (e.g. a subsystem of one or more networks 290, 890, 990, 1090, 1290) in which one or more technologies may be implemented. A motor vehicle or other device 1241 associated with a care administration space (a location 1204 inside or near ambulance 1295 configured to permit one or more caregivers 1291 to treat a patient 1292 in trauma, e.g.) may include one or more instances of wireless transceivers 1211, wall mountings 1213, display screens 1216, or couplings 1218 to external power. Also in some contexts, as described below, device 1241 may be configured to obtain and present one or more medical records 1217 (comprising one or more data components 126, 128 relating to an emergency protocol 120 or to a specific patient 1292 relayed via display screen 1216, e.g.). This can occur, for example, in a context in which a wrist band 1223 or other device 1242 worn or held by patient 1292 contains one or more implementations of conditional consent 1222 (configured by patient 1292 prior to an emergency, e.g.) or transponders 1225 as described below.

Figure 18:
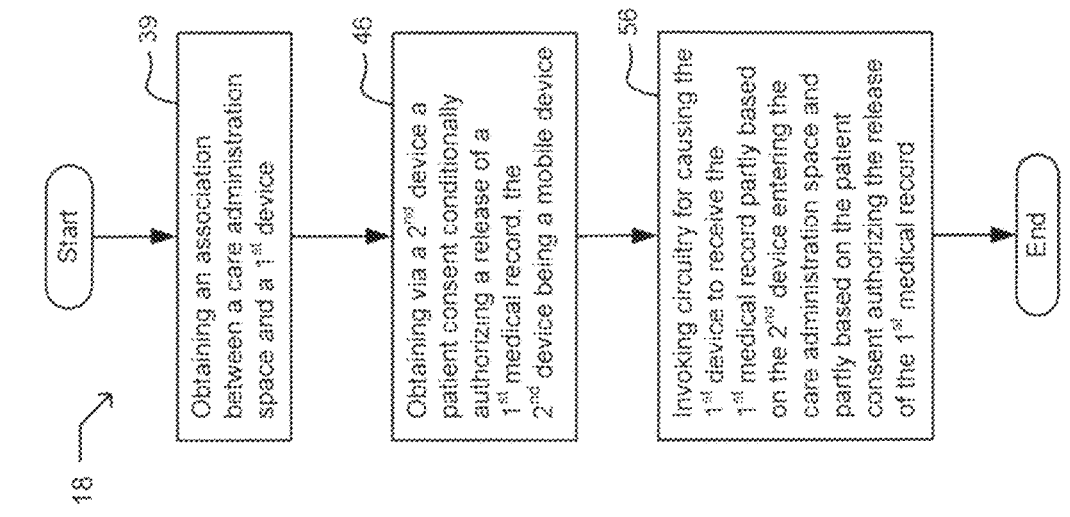
FIG. 18 depicts a high-level logic flow of an operational process described with reference to FIG. 12.

With reference now to FIG. 18, shown is a high-level logic flow 18 of an operational process. Intensive operation 39 describes obtaining an association between a care administration space and a first device (e.g. configuration module 322 making a record 568 in which an identifier 734 of the "first" device 242, 1241 is associated with an identifier 732 of an ambulance 1295 or other location 204 allocated to providing patients 292 medical care). This can occur, for example, in a context in which "first" device 242, 1241 includes a wall mounting 1213 fixing it in relation to the care administration space; in which the "first" device includes a wireless transmitter 394 or transceiver 1211 detectable by a "second" device as described below; and in which the care administration space is defined by the effective range of the wireless transmitter 394 or transceiver 1211. In some contexts, for example, such locations 204 may include an emergency room or urgent care clinic. Alternatively or additionally, a regional server 1195 or other stationary device in network 1290 may be configured to obtain GPS data 751 indicating a current position of an ambulance 1295 or other mobile care administration space that may then be compared with GPS data 752 indicating a current position of a device held or worn by patient 292 (e.g. through network 1290 in lieu of direct wireless transmission between proximate devices 1241, 1242). In some contexts, moreover, the "first" device may comprise an external power coupling 1218 configured to power the "first" device for an indefinite period (via a vehicle battery or similar source that is maintained daily, e.g.).

In light of teachings herein, numerous existing techniques may be applied for configuring special-purpose circuitry or other structures effective for configuring a device for direct or indirect wireless communication as described herein without undue experimentation. See, e.g., U.S. Pat. No. 7,986,940 ("Automatic wireless network linking method with security configuration and device thereof"); U.S. Pat. No. 7,940,744 ("System, apparatus and method for automated wireless device configuration"); U.S. Pat. No. 7,929,950 ("Dynamically configurable IP based wireless device and wireless networks"); U.S. Pat. No. 7,916,707 ("Identity-based wireless device configuration"); U.S. Pat. No. 7,885,687 ("Device for updating configuration information in a wireless network"); U.S. Pat. No. 7,778,752 ("System for connecting a telematics device to a vehicle using a wireless receiver configured to transmit diagnostic data"); U.S. Pat. No. 7,681,231 ("Method to wirelessly configure a wireless device for wireless communication over a secure wireless network"); U.S. Pat. No. 7,643,828 ("Method and apparatus for fast link setup in a wireless communication system"); U.S. Pat. No. 7,616,594 ("Wireless device discovery and configuration"); and U.S. Pat. No. 7,233,745 ("Field device configured for wireless data communication").

Intensive operation 46 describes obtaining via a second device a patient consent conditionally authorizing a release of a first medical record, the second device being a mobile device (e.g. input module 315 receiving pre-emergency input 551 from or about a patient 492 that includes a conditional consent 1222 permitting a release of the one or more medical records 567, 1217 of the patient's to a caregiver 991, 1291 that is contingent upon the occurrence of an emergency). This can occur, for example, in a context in which the patient 492 (who can, in some instances, be the same individual as one or more other identified patients depicted herein, e.g.) enters such pre-emergency input 551 (by a menu selection, e.g.) using a handheld device (the "second" device 1242, e.g.); in which the "occurrence of an emergency" is manifested as the "second" device entering the "care administration space" (e.g. location 204, 1204); and in which the authorization to release the "first" medical record would otherwise be much slower (due to trauma, e.g.). In some contexts, for example, the "first" device may be configured to include one or more media 105, 505 bearing such contingently-releasable medical records 1217 for most or all registered patients 992, 1292 (patients enrolled in registry 109, e.g.) in a region (county or state, e.g.) so that the "first" and "second" devices 1241, 1242 may easily interact directly and locally (not via network 1290, e.g.) with or without network 1290 being online. Alternatively or additionally, the "second" device may include a wrist band 1223 wearable by an at-risk patient 1292 (e.g. one suffering from dementia, epilepsy, or other medical conditions that make it more likely that a patient may be unable to consent to a records transfer).

In light of teachings herein, numerous existing techniques may be applied for configuring special-purpose circuitry or other structures effective for conducting a structured dialogue with a patient or caregiver as described herein without undue experimentation. See, e.g., U.S. Pat. No. 8,065,250 ("Methods and apparatus for predictive analysis"); U.S. Pat. No. 8,024,179 ("System and method for improving interaction with a user through a dynamically alterable spoken dialog system"); U.S. Pat. No. 7,610,556 ("Dialog manager for interactive dialog with computer user"); U.S. Pat. No. 7,539,656 ("System and method for providing an intelligent multi-step dialog with a user"); U.S. Pat. No. 7,461,000 ("System and methods for conducting an interactive dialog via a speech-based user interface"); and U.S. Pat. No. 7,114,954 ("Interaction education system for teaching patient care").

Extensive operation 56 describes invoking circuitry for causing the first device to receive the first medical record partly based on the second device entering the care administration space and partly based on the patient consent authorizing the release of the first medical record (e.g. invocation module 372 causing display screen 1216 of device 1241 to display medical record 1217 as an automatic response to the "second" device 1242 entering the care administration space and partly based on the prior configuration of above-described conditional consent 1222 (in operation 46, e.g.). In some contexts, for example, such configuration may have been implemented by a non-emergency caregiver 991 who provides the patient with the "second" device 1242. Alternatively or additionally, in some contexts, a local entity (a hospital 201 or ambulance company, e.g.) may own the first device, a patient may own the second device, and a third entity may own the invoked "circuitry."

In light of teachings herein, numerous existing techniques may be applied for configuring special-purpose circuitry or other structures effective for identifying wireless devices in a region of interest as described herein without undue experimentation. See, e.g., U.S. Pat. No. 7,903,905 ("Pen-shaped scanning device having a region identity sensor"); U.S. Pat. No. 7,869,807 ("Method of managing a code identifying a wireless device with conflict minimized in a wireless telecommunications system"); U.S. Pat. No. 7,319,876 ("System and method for using equipment identity information in providing location services to a wireless communication device"); U.S. Pat. No. 7,295,120 ("Device for verifying a location of a radio-frequency identification (RFID) tag on an item"); U.S. Pat. No. 6,791,477 ("Method and apparatus for identifying waypoints and providing keyless remote entry in a handheld locator device"); U.S. Pat. No. 6,693,512 ("Device location and identification system"); and U.S. Pat. No. 6,392,747 ("Method and device for identifying an object and determining its location").

With reference now to FIG. 13, shown is an example of a system 13 (e.g. a subsystem of one or more networks 290, 890, 990, 1090, 1290) in which one or more technologies may be implemented. As shown, caregiver 1391 wears a device 1342 (on a lanyard or clothing 1349, e.g.) configured to include a caregiver identifier 1332 that identifies her. Likewise patient 1331 wears a device 1341 configured to include a patient identifier 1331 that identifies him (on a gown or wrist band 1223, e.g.). In some variants, such wearable devices 1341, 1342 are configured to interact wirelessly (either with one another or with a wall-mounted device 1343, e.g.) as an automatic response to being in a common location (e.g. at location 1204, 1304).

With reference now to FIG. 19, shown is a high-level logic flow 19 of an operational process. Intensive operation 38 describes obtaining an indication of a first device associated with and wearable by a patient hospitalized for a particular condition (e.g. configuration module 322 associating a specific patient 1392 with a patient identifier 1331 on an article wearable by a patient 1392 who has been admitted to hospital 201 for a specific pathology 181 or complaint 513). This can occur, for example, in a context in which the article (a wrist band 1223, e.g.) is assigned to patient 1392 upon checking in to the hospital; in which configuration module 322 was invoked at that time (at patient intake, e.g.); and in which one or more instances of device 305 reside on one or more networks described herein (in a wall-mounted device 1343 or server 1195 of hospital 201, e.g.). Alternatively or additionally, a stationary device 1343 may perform operation 38 by detecting a device 1341 associated with patient 1392 in a given location 1304 (entering his hospital room, e.g.).

In light of teachings herein, numerous existing techniques may be applied for configuring special-purpose circuitry or other structures effective for permitting an identification of a person by a wearable article as described herein without undue experimentation. See, e.g., U.S. Pat. No. 8,068,008 ("Emergency responder credentialing system and method"); U.S. Pat. No. 8,049,597 ("Systems and methods for securely monitoring an individual"); U.S. Pat. No. 8,039,093 ("Method for preparing tamperproof ID documents"); U.S. Pat. No. 7,988,043 ("Fraud prevention in issuance of identification credentials"); U.S. Pat. No. 7,979,286 ("Patient-interactive healthcare management"); U.S. Pat. No. 7,975,913 ("Discernment card and a discernment card business system using the discernment card"); U.S. Pat. No. 7,481,370 ("Removable patient identification strap for blood recipient verification"); and U.S. Pat. No. 6,748,687 ("Multi-web business form having moisture proof wristband, identification labels and web joint").

Intensive operation 41 describes obtaining an indication of a second device associated with and wearable by a caregiver (e.g. configuration module 321 associating a specific caregiver 1391 with a caregiver identifier 1332 on an article wearable by the caregiver). This can occur, for example, in a context in which the article (on a badge or lanyard or in a wrist band or article of clothing 1349, e.g.) was assigned to caregiver 1391 upon arriving at the facility and in which configuration module 321 was invoked at that time. Alternatively or additionally, a stationary device 1343 (mounted on a wall, e.g.) may perform operation 41 by detecting a device 1342 associated with caregiver 1391 in a given location 1304 (entering her patient's hospital room, e.g.).

Intensive operation 45 describes causing a recordation of a timestamp as an automatic response to the first device associated with and wearable by the patient and the second device associated with and wearable by the caregiver both being in a single common location (e.g. configuration module 324 storing a timestamp 711 indicating when both caregiver 1391 and patient 1392 were together in location 1304). This can occur, for example, in a context in which timestamp 711 is generated from a digital clock 392; in which record 710 is initially aggregated at one or more devices 1341-1343 locally, in which one or more records archives 820, 920 later received record 710 in a batch data aggregation process, and in which the "single common location" is a hospital room or a detection range of one or more devices 1341-1343. In some implementations, for example, device 1341 may include one or more configuration modules 321-326 as described herein and may be configured to perform operations 38, 41, and 45 (in lieu of device 1343, e.g.). Alternatively or additionally, in some variants, device 1342 may likewise include one or more configuration modules 321-326 as described herein and may be configured to implement device 305 (e.g. operable to perform operations 38, 41, and 45).

In light of teachings herein, numerous existing techniques may be applied for configuring special-purpose circuitry or other structures effective for implementing an automatic timestamp and recordation as described herein without undue experimentation. See, e.g., U.S. Pat. No. 8,000,979 ("Automated patient management system"); U.S. Pat. No. 7,844,837 ("Electronic device and timer therefor with tamper event time stamp features and related methods"); U.S. Pat. No. 7,643,465 ("Method for insertion of time stamp into real time data within a wireless communications network"); U.S. Pat. No. 7,289,651 ("Image reporting method and system"); U.S. Pat. No. 7,283,566 ("Method and circuit for generating time stamp data from an embedded-clock audio data stream and a video clock"); U.S. Pat. No. 7,257,158 ("System for transmitting video images over a computer network to a remote receiver"); U.S. Pat. No. 7,100,210 ("Hood intrusion and loss of AC power detection with automatic time stamp"); U.S. Pat. No. 6,893,396 ("Wireless internet bio-telemetry monitoring system and interface"); and U.S. Pat. No. 6,656,122 ("Systems and methods for screening for adverse effects of a treatment").

Extensive operation 55 causing a retrieval of the timestamp in response to an indication of an institutional readmission after the recordation of the timestamp indicating the first device associated with and wearable by the patient and the second device associated with and wearable by the caregiver both having been in the single common location (e.g. response module 352 retrieving a record 710 including such timing data 453 from one or more records archives 820, 920 in response to a request 581 indicative of patient 1392 being readmitted to one or more hospitals 201, 202 for the same specific pathology 181 or complaint 513). This can occur, for example, in a context in which such readmission for the particular condition would otherwise trigger a reduction in payment for one or more prior hospitalizations. In some contexts, for example, one or more remote requestors 893, 993 may have initiated a prior instance of operation 55 (performed by a remote instance of invocation module 371, e.g.) in which an entity's request 581 for records included a readmission-indicative report type 521 (having a name that includes "readmission," e.g.), a readmission-indicative request authorization 522 (from an agency that monitors excessive readmissions, e.g.), a query reciting or prompted by readmission, or other such explicit or implicit indications 525 of readmission that might have been avoidable if a prior hospitalization or treatment had been executed correctly. Alternatively or additionally, response module 352 may be configured to perform operation 55 by retrieving and transmitting such a timestamp-containing record 710 (indicative of when the first and second devices 1341, 1342 were both in the single common location 1304, e.g.) to one or more remote requestors 893, 993.

Figure 20:
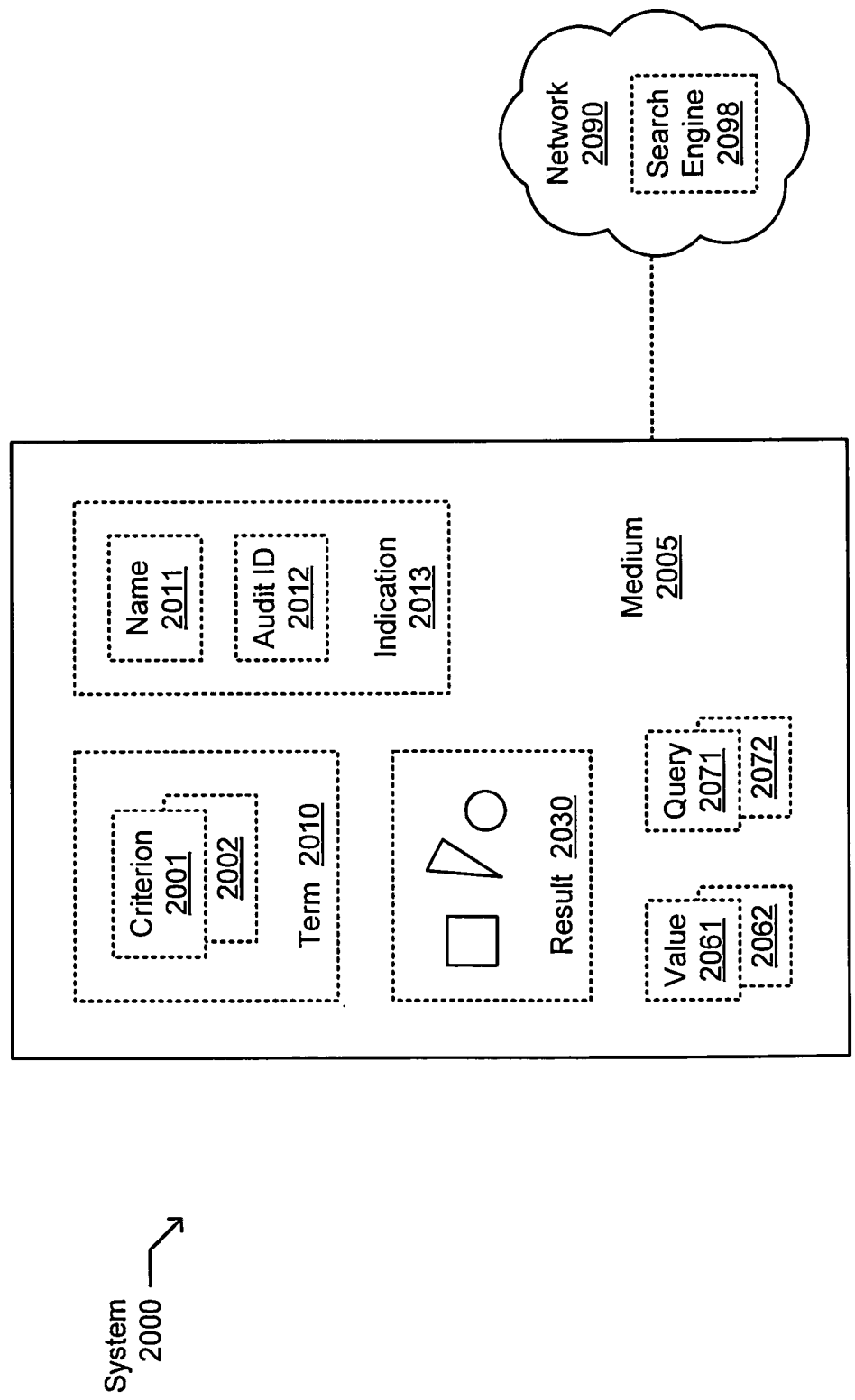
FIG. 20 depicts an exemplary environment in which one or more technologies may be implemented in one or more data-handling media on a network.

With reference now to FIG. 20, shown is context in which one or more technologies may be implemented. System 2000 includes one or more data-handling media 2005 (residing in an instance of device 305, e.g.) operably coupled with one or more search engines 2098 on networks 2090 as described above. Medium 2005 may include one or more instances of search terms 2010 (e.g. comprising criteria 2001, 2002); names 2011, audit identifiers 2012, or other such indications 2013; search results 2030; values 2061, 2062; or queries 2071, 2072 as described below.

Figure 21:
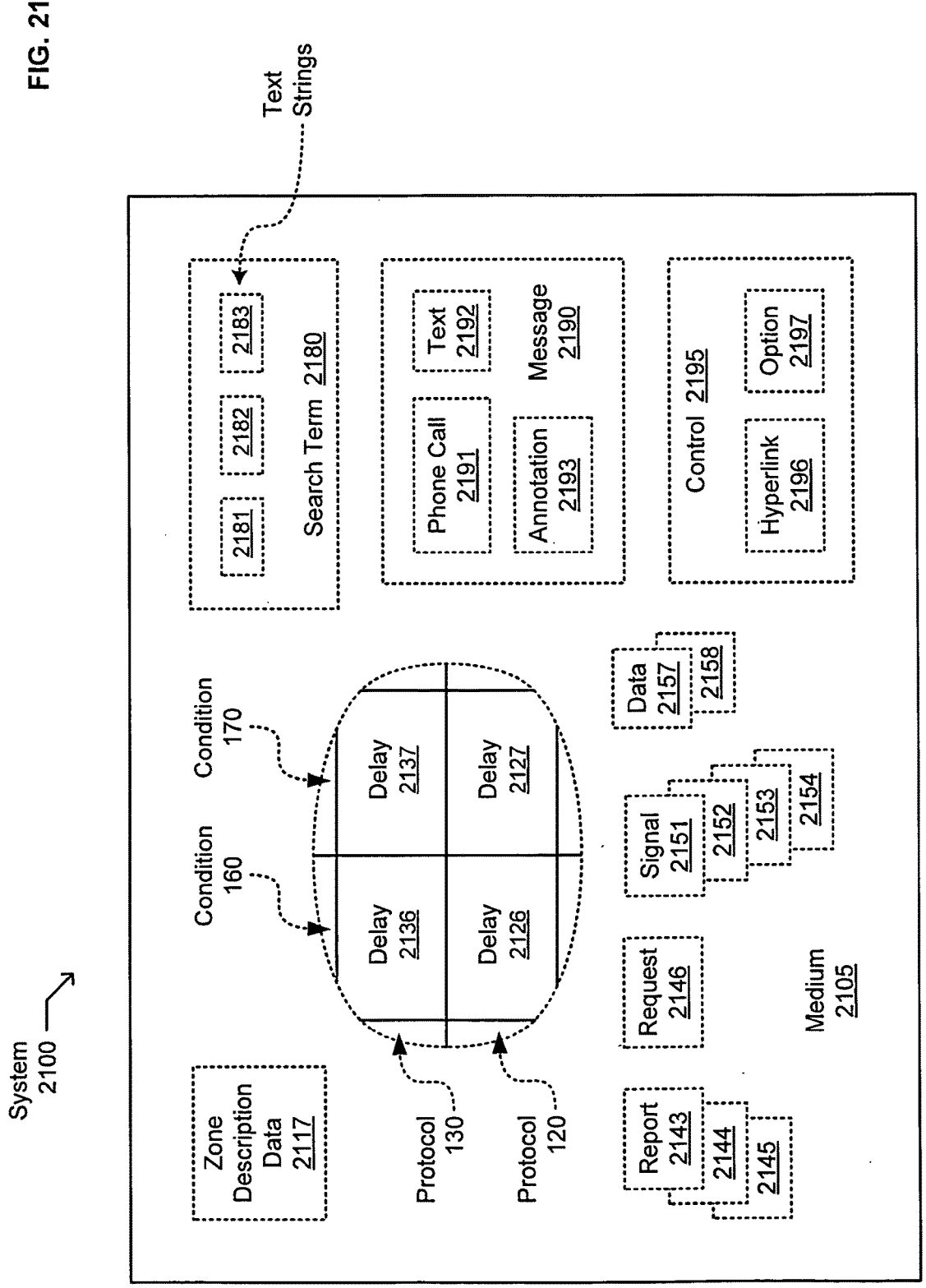
FIG. 21 depicts another exemplary environment in which one or more technologies may be implemented in one or more data-handling media.

With reference now to FIG. 21, shown is context in which one or more technologies may be implemented. System 2100 may (optionally) include one or more data-handling media 2105 (configured to transmit or store data, e.g.) residing in an instance of device 305 or otherwise on a network 290 as described above. In some variants, medium 2105 may bear one or more instances of zone description data 2117 (e.g. representing one or more service zones 207, 208 or other locations 204, 1204, 1304); data components 126, 127, 136, 137 (in tabular form, e.g.); reports 2143, 2144, 2145; requests 2146; signals 2151, 2152, 2153, 2154 (comprising audio data 2157 or other encoded data 2158, e.g.); search terms 2180 (comprising one or more text strings 2181, 2182, 2183 connected by logical operators, e.g.); messages 2190 (comprising phone calls 2191, text 2192, and annotations 2193 as described below, e.g.); and hyperlinks 2196, menu options 2197, or other such controls 2195 (comprising one or more interfaces 1001, 1002 or other devices described above, e.g.). In some contexts, data component 126 (as described above) may include one or more delays 2126 corresponding specifically to the handling of condition 160 with protocol 120; data component 127 (as described above) may include one or more delays 2127 corresponding specifically to the handling of condition 170 with protocol 120; data component 136 (as described above) may include one or more delays 2136 corresponding specifically to the handling of condition 160 with protocol 130; and data component 137 (as described above) may include one or more delays 2137 corresponding specifically to the handling of condition 170 with protocol 130. Moreover in some variants each instance of audio data 2157 may include one or more timestamps 711 as well as other data 712 (transcripts or labels of patient interview clips, recorded physician remarks, concurrent diagnostic data 490, or other events encoded as text 2192 or other annotations 2193 relating to raw auditory data with which they are archived, e.g.).

Figure 22:
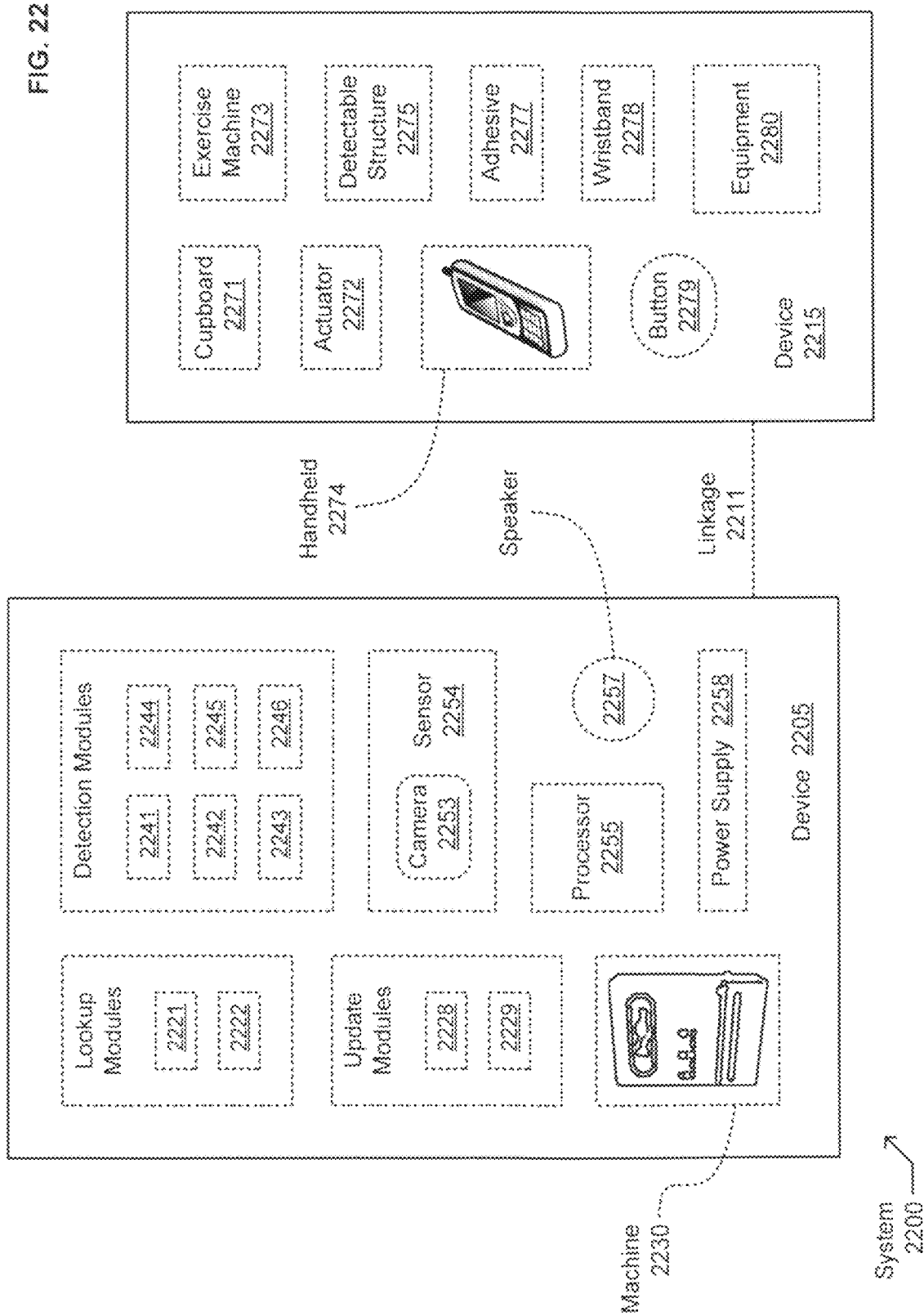
FIG. 22 depicts another exemplary environment in which one or more technologies may be configured to operate between or among respective devices.

With reference now to FIG. 22, shown is context in which one or more technologies may be implemented. System 2200 may include two or more devices 2205, 2215 having a linkage 2211 therebetween as described below. In various embodiments, device 2205 may include one or more instances of lookup modules 2221, 2222; update modules 2228, 2229; detection modules 2241, 2242, 2243, 2244, 2245, 2246; cameras 2253 or other sensors 2254; or processors 2255 as described below. Alternatively or additionally, device 2205 may comprise a machine 2230 (configured for vending or other dispensations of drugs 141, foods, or other goods 691, e.g.); a battery or other on-board power supply 2258; or one or more speakers 2257 (configured to manifest a warning 1119 or other audio data 2157 as described below, e.g.). In various implementations, device 2215 may likewise include one or more instances of food containers (refrigerators or cupboards 2271, e.g.); actuators 2272 (of a dispenser, e.g.); exercise machines 2273 (relating to a regimen 650, e.g.); handhelds 2274 (telephones, e.g.); detectable structures 2275 (transponder or barcode, e.g.); adhesives 2277; wristbands 2278; or buttons 2279. Alternatively or additionally, device 2215 may comprise medical equipment 2280 (devices configured for imaging or measurement, e.g.). One or more of devices 2205, 2215 may be configured to implement an instance of device 305 and to include one or more media 105, 405, 505, 605, 705, 2005, or 2105 depicted above.

Figure 23:
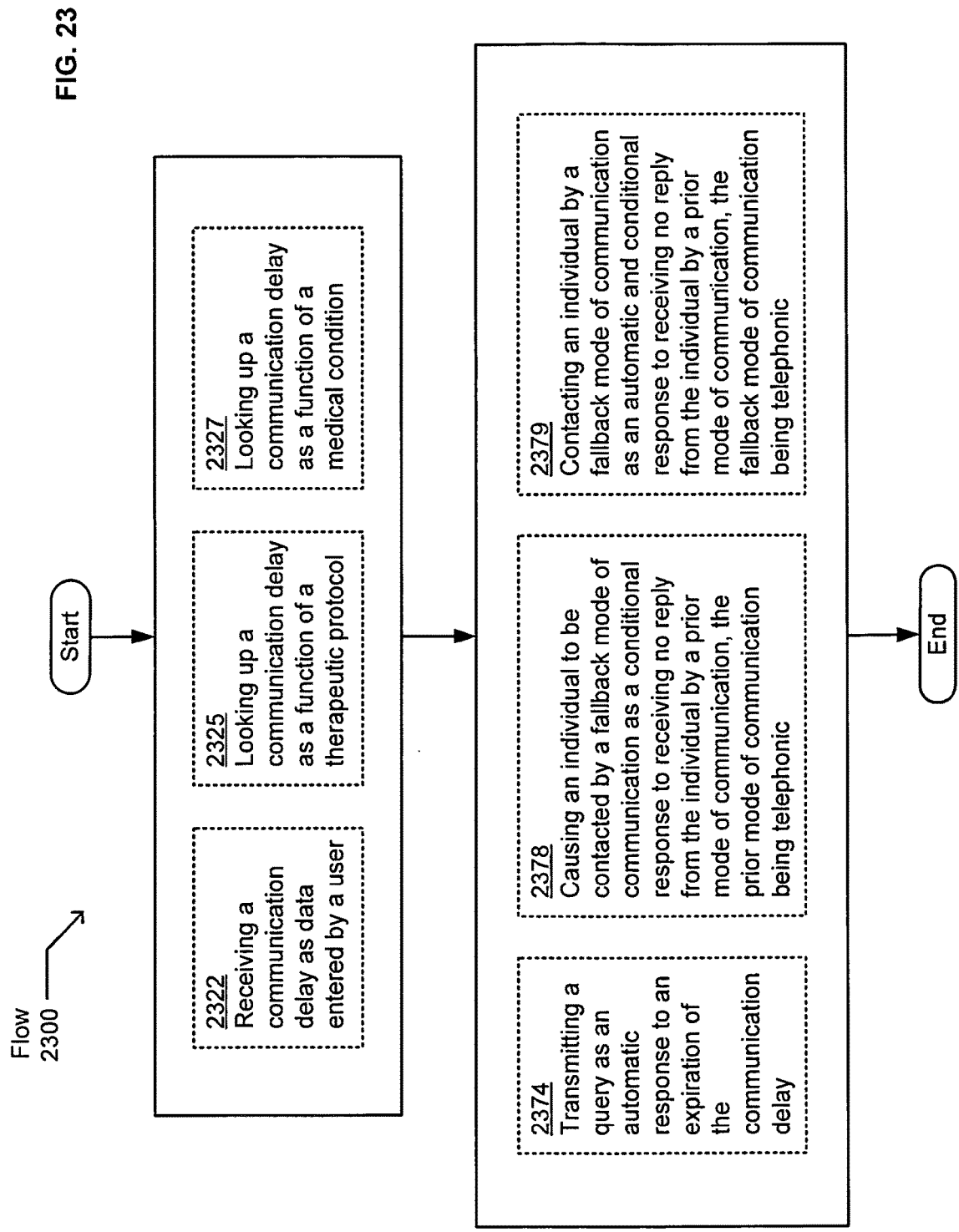
FIG. 23 depicts variants of flows shown in one or more of FIGS. 14-19.

With reference now to flow 2300 of FIG. 23 and to other flows 14-19 described above, in some variants, one or more of operations 2322, 2325 may be performed in conjunction with intensive operations described above or in preparation for one or more extensive operations described above. Alternatively or additionally, one or more of operations 2374, 2378, 2379 may likewise be performed in response to one or more intensive operations described above or in conjunction with extensive operations described above.

Intensive operation 2322 describes receiving a communication delay as data entered by a user (e.g. input module 312 receiving data 2158 that includes delay 2137 from an end user device 2215 or system 841, 941). This can occur, for example, in a context in which the user is a caregiver or patient 292 who operates an implementation of device 305; in which input module 312 can accept such data 2158 as a user preference 725 (e.g. by asking "when should we contact you?"); in which delay 2137 comprises an integer number of days; and in which means for performing one or more intensive operations 35-46 as described above include an implementation of device 305. Alternatively or additionally, one or more input modules 311-319 may be configured to obtain other such data 2158 as described herein. In one such configuration, for example, input module 317 may be configured to let the user enter an e-mail address 721, telephone number 722, or other contact information 720 manifesting one or more of the user's preferences 725 (to be used in operation 2374 described below, e.g.).

Intensive operation 2325 describes looking up a communication delay as a function of a therapeutic protocol (e.g. lookup module 2221 returning delay 2137 selectively in response to an indication that protocol 130 is being used for treating someone). This can occur, for example, in a context in which means for performing one or more intensive operations 35-46 as described above include an implementation of device 2205; in which a data component 127 associated with a different therapeutic protocol 120 includes a communication delay 2127 of 2.0 hours (as a digital expression, e.g.); in which one or more data components 137, 138 specifically associated with therapeutic protocol 130 each includes a communication delay 2137 that is more than 2.0 hours; and in which an appropriate entity (a caregiver 1391 or expert consultant, e.g.) has determined that such a communication delay 2137 will be more effective (than a shorter delay 2127, e.g.) following a triggering event (an order or administration, e.g.) for eliciting participation from a population of patients or caregivers who adopt a therapeutic protocol 130. In some contexts, for example, a table of suitable communication delays 2126, 2136, 2127, 2137 may be estimated (by a survey of experienced nurses or physician's assistants, e.g.) as a median time within which each given condition 160, 170 typically produces a detectable change in symptoms (relating to each respective protocol, e.g.). In some contexts, moreover, a slightly longer period (by 1% to 50% or 1-3 standard deviations across a survey distribution, e.g.) may be preferable. Alternatively or additionally, the lookup result (communication delay 2137, e.g.) may depend as a function of a medical condition (being shorter than a communication delay 2136 associated with the same protocol 130 but a different condition 160, e.g.). Such a configuration of tabular data may be useful, for example, in a context in which protocol 130 (taking an angiotensin-converting enzyme inhibitor, e.g.) typically provides a faster detectable response in treating condition 170 (shortness of breath, e.g.) than in treating condition 160 (leg swelling, e.g.).

In light of teachings herein, numerous existing techniques may be applied for configuring special-purpose circuitry or other structures effective for implementing lookup functions as described herein without undue experimentation. See, e.g., U.S. Pat. No. 7,940,982 ("Method and apparatus for color space conversion using per-color selection of look-up table density"); U.S. Pat. No. 7,921,088 ("Logical operations encoded by a function table for compressing index bits in multi-level compressed look-up tables"); U.S. Pat. No. 7,916,137 ("Generation of 3D look-up tables for image processing devices"); U.S. Pat. No. 7,847,989 ("Method for conversion of a colour space using separate chromatic and luminance look-up tables"); U.S. Pat. No. 7,706,034 ("Multi-Dimensional look-up table generation via adaptive node selection based upon color characteristics of an input image"); U.S. Pat. No. 7,558,961 ("Systems and methods for embedding messages in look-up tables"); U.S. Pat. No. 7,370,069 ("Numerical value conversion using a look-up table for coefficient storage"); U.S. Pat. No. 7,346,642 ("Arithmetic processor utilizing multi-table look up to obtain reciprocal operands"); and U.S. Pat. No. 6,981,080 ("Look-up table based USB identification").

Intensive operation 2327 describes looking up a communication delay as a function of a medical condition (e.g. lookup module 2222 selecting delay 2137 in response to an indication that a patient 292 is being treated for condition 170). This can occur, for example, in a context in which a data component 136, associated with a different condition 160 includes a communication delay 2136 of 2.0 calendar months (as a digital expression, e.g.); in which one or more data components 137, 147 specifically associated with medical condition 170 each includes a communication delay 2137 that is less than 2.0 calendar months; and in which an appropriate entity (a specialist or other physician, e.g.) has determined that such a communication delay 2137 will be more effective (than a longer delay 2136, e.g.) following a triggering event (an estimated delivery time, e.g.) for eliciting participation from a population of caregivers or patients who treat or suffer from medical condition 170. Alternatively or additionally, the lookup result (data component 137, e.g.) may depend as a function of a therapeutic protocol (having a communication delay 2137 longer than that of a data component 127 associated with the same condition 170 but a different protocol 120, e.g.). Such a configuration of tabular data may be useful, for example, in a context in which treating condition 170 (back pain, e.g.) with protocol 130 (a particular weightlifting exercise in a sauna, e.g.) will not generally permit an evaluation of treatment effectiveness as soon as that of protocol 120 (medication, e.g.).

Extensive operation 2374 describes transmitting a query as an automatic response to an expiration of the communication delay (e.g. statement module 381 transmitting one or more queries 571-574 relating to protocol 120 or to condition 160 only after waiting for a time interval specified by delay 2126). This can occur, for example, in a context in which one or more of operations 2322, 2325, 2327 have been performed; in which a prior communication (such as an input 551-552 or query 571-574 or request 581, 582 or order 1018, 1118) or other event described herein tolled the beginning of the time interval and in which means for performing one or more extensive operations 51-57 as described above include an implementation of device 305. Alternatively or additionally, in various embodiments, statement module 381 may be configured to trigger one or more other extensive operations as described herein upon such expiration.

Extensive operation 2378 describes causing an individual to be contacted by a fallback mode of communication as a conditional response to receiving no reply from the individual by a prior mode of communication, the prior mode of communication being telephonic (e.g. response module 354 taking no action if a reply 555 to a phone call 2191 is received before an expiration of delay 541 but otherwise initiating another message 2190 to the individual). This can occur, for example, in a context in which the delay 541 is on the order of ten seconds (within an order of magnitude, e.g.); in which the reply 555 may take the form of a key press or utterance (as indicated in FIG. 10, e.g.) during the phone call 2191; and in which the fallback mode of communication includes a delivery (by a fax or other machine 2230 installed in the individual's home 289 or office or by an automatically placed order to a third party with delivery instructions, e.g.) of a physical article (in which message 2190 comprises one or more instance of reminder letters or goods 691, e.g.) to the individual. Alternatively or additionally, in a context in which a foreseeable reply 555 may take the form of a return phone call 2191, e-mail message (containing specific text 2192, or online session (via the Internet, e.g.), the delay 541 may be on the order of one hour or one week (within 1 or 2 orders of magnitude, e.g.).

In light of teachings herein, numerous existing techniques may be applied for configuring special-purpose circuitry or other structures effective for determining whether specific input has been received from a person within a particular time interval as described herein without undue experimentation. See, e.g., U.S. Pat. No. 8,055,240 ("Method of notifying a caller of message confirmation in a wireless communication system"); U.S. Pat. No. 8,045,693 ("Message reception confirmation method, communications terminal and message reception confirmation system"); U.S. Pat. No. 7,707,624 ("System for, and method of, proving the transmission, receipt and content of a reply to an electronic message"); U.S. Pat. No. 7,483,721 ("Communication device providing diverse audio signals to indicate receipt of a call or message"); U.S. Pat. No. 7,283,807 ("Method and telecommunication system for indicating the receipt of a data message"); U.S. Pat. No. 7,031,734 ("System and method for confirming short message service (SMS) message reception in mobile communication terminal"); U.S. Pat. No. 7,020,458 ("Method and telecommunication system for indicating the receipt of a data message"); U.S. Pat. No. 6,553,341 ("Method and apparatus for announcing receipt of an electronic message"); and U.S. Pat. No. 6,122,485 ("Method and system for confirming receipt of a message by a message reception unit").

Extensive operation 2379 describes contacting an individual by a fallback mode of communication as an automatic and conditional response to receiving no reply from the individual by a prior mode of communication, the fallback mode of communication being telephonic (e.g. response module 355 taking no action if a reply 555 to a prior message 2190 is received within a time interval 538 but otherwise initiating a phone call 2191 to the individual). This can occur, for example, in a context in which the prior message 2190 (comprising text 2192 or a phone query 571, e.g.) was sent by a request module 331, 332 as described above; in which the prior message 2190 included a hyperlink 2196, menu option 2197, or other such control 2195 configured to facilitate the individual providing input 552 to response module 355 without the need to include any direct communication with other individuals; in which the time interval 538 began when the prior message 2190 was sent; in which response module 355 infers the "receiving no reply from the individual" if the time interval 538 ends without such input 552; and in which means for performing one or more extensive operations 51-57 as described above include an implementation of device 305. In some implementations, for example, the time interval 538 may be on the order of 3.0 days or of 3.0 months (within an order of magnitude, e.g.). Alternatively or additionally, response module 355 may be configured (as an auto-dialer, e.g.) to initiate a phone call 2191 between a call center 295 and the individual (a caregiver or patient 292, e.g.) as an automatic response partly based on the time interval 538 having expired and partly based on an immediate availability of a call center agent 294 (manifested as an indication 684 of the agent's current status, e.g.).

In light of teachings herein, numerous existing techniques may be applied for configuring special-purpose circuitry or other structures effective for facilitating the operation of a call center or otherwise initiating communications as described herein without undue experimentation. See, e.g., U.S. Pat. No. 8,069,213 ("Method of controlling access to network resources using information in electronic mail messages"); U.S. Pat. No. 7,860,935 ("Conditional communication"); U.S. Pat. No. 7,783,023 ("Systems and methods for providing unified collaboration systems with conditional communication handling"); U.S. Pat. No. 7,484,048 ("Conditional message delivery to holder of locks relating to a distributed locking manager"); U.S. Pat. No. 7,042,338 ("Alerting a care-provider when an elderly or infirm person in distress fails to acknowledge a periodically recurrent interrogative cue"); U.S. Pat. No. 6,307,937 ("Method and apparatus for an adapter card providing conditional access in a communication system"); and U.S. Pat. No. 6,108,709 ("System for sending an e-mail message to a first type of terminal based upon content thereof and selected conditions and selectively forwarding it to a second type of terminal").

Figure 24:
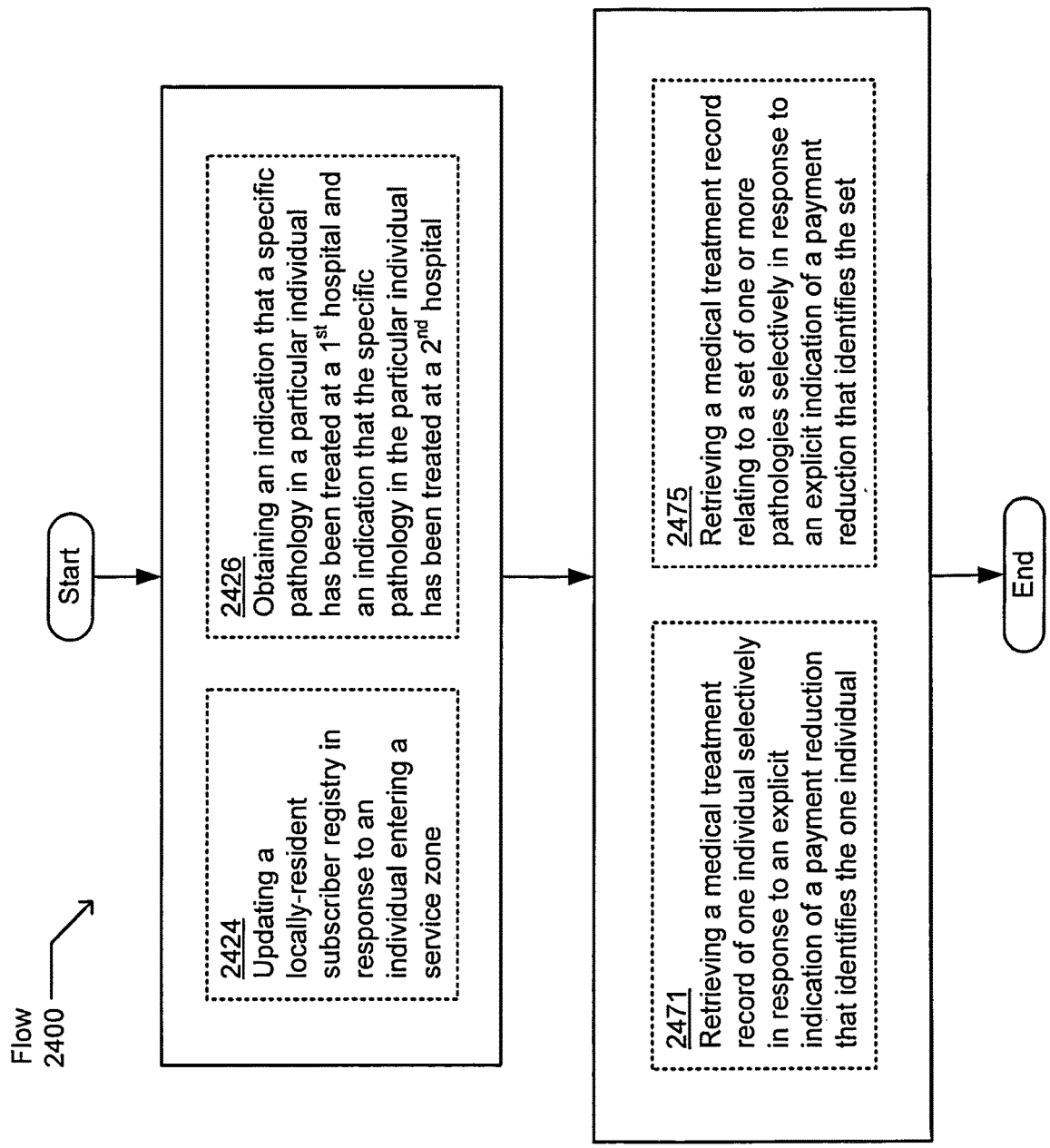
FIG. 24 depicts variants of flows shown in one or more of FIG. 14-19 or 23.

With reference now to flow 2400 of FIG. 24 and to other flows 14-19, 2300 described above, in some variants, one or more of operations 2424, 2426 may be performed in conjunction with intensive operations described above or in preparation for one or more extensive operations described above. Alternatively or additionally, one or more of operations 2471, 2475 may likewise be performed in response to one or more intensive operations described above or in conjunction with extensive operations described above.

Intensive operation 2424 describes updating a locally-resident subscriber registry in response to an individual entering a service zone (e.g. update module 2228 adding an identifier 733 of the individual to a registry 109 stored on a medium 105 in service zone 207 in response to an indication 683 that the individual has entered service zone 207). This can occur, for example, in a context in which the individual is a patient 292, 1392 as described herein; in which service zone 207 is a defined region (a county or metropolitan area, e.g.); in which device 2205 is on network 290; in which device 2215 is held or worn by patient 292; in which detection module 2242 detects that patient 292 has entered service zone 207 by comparing zone description data 2117 (defining service zone 207, e.g.) with GPS data 752 indicating a current position of device 2215; in which detection module 2242 responds by passing the indication 683 to update module 2228; and in which means for performing one or more intensive operations 35-46 as described above include an implementation of device 2205. Alternatively or additionally, detection module 2242 may determine whether the individual has entered service zone 207 simply by detecting whether device 2215 is within a direct operating range of device 2205.

In light of teachings herein, numerous existing techniques may be applied for configuring special-purpose circuitry or other structures effective for determining whether a device is in a location or region as described herein without undue experimentation. See, e.g., U.S. Pat. No. 8,019,168 ("Motion detecting device and search region variable-shaped motion detector"); U.S. Pat. No. 8,000,723 ("System of utilizing cell information to locate a wireless device"); U.S. Pat. No. 7,986,237 ("Location management method using RFID series"); U.S. Pat. No. 7,932,830 ("Method of assigning and deducing the location of articles detected by multiple RFID antennae"); U.S. Pat. No. 7,605,688 ("Vehicle location determination system using an RFID system"); U.S. Pat. No. 7,573,369 ("System and method for interrogating and locating a transponder relative to a zone-of-interest"); U.S. Pat. No. 7,525,425 ("System and method for defining an event based on relationship between an object location and a user-defined zone"); U.S. Pat. No. 7,046,162 ("Method and apparatus to locate a device in a dwelling or other enclosed space"); and U.S. Pat. No. 6,205,326 ("Method for determining when a communication unit is located within a preferred zone").

Intensive operation 2426 describes obtaining an indication that a specific pathology in a particular individual has been treated at a first hospital and an indication that the specific pathology in the particular individual has been treated at a second hospital (e.g. retrieval module 343 extracting a first record 671 indicating that patient 292 was first treated at hospital 201 for pathology 181 and a second record 672 indicating that the same patient 292 was later treated at hospital 202 for the same pathology 181). This can occur, for example, in a context in which retrieval module 343 comprises one or more of the means for performing intensive operations 35-46 as described above; in which retrieval module 343 has access to one or more records archives 820, 920 pertaining to treatments at both hospitals 201, 202; in which the institutional readmission (whichever was later, e.g.) and some suspect conditions (those that are not objectively verifiable or even supported by evidence, e.g.) or protocols (those that signal possible caprice or ulterior motivation on the part of a patient or caregiver, e.g.) together suggest a possibility of fraud or neglect that might warrant a clawback or payment reduction for one or more hospitalizations or protocols; in which the records 671, 672 identify one or more protocols 130, 140 performed in relation to the specific pathology 181; and in which such records 671, 672 pertaining to the particular individual (patient 292, e.g.) both identify pathology 181 in an identical or sufficiently similar manner. Such a context can exist, for example, where retrieval module 343 automatically recognizes identical or related pathology identifiers 511 in use at both hospitals 201, 202. Alternatively or additionally, a user who invokes retrieval module 343 (an auditor who has some cause to suspect fraud or abuse, e.g.) may provide two or more instances of pathology identifiers 511 (expressed as text strings 2181, 2182 of a search term, e.g.) that are considered related, optionally with a name or other identifiers of the particular individual (as another text string 2183 of the search term, e.g.).

Extensive operation 2471 describes retrieving a medical treatment record of one individual selectively in response to an explicit indication of a payment reduction that identifies the one individual (e.g. retrieval module 341 extracting whichever billing or other records 561-569 contain data components 127, 137, 147 pertaining to treatment of a medical condition 170 of a specific patient 292 at hospital 202 in response to an explicit indication 2013 of a potential or actual payment reduction identifying the specific patient 292). This can occur, for example, in a context in which means for performing one or more extensive operations 51-57 as described above include an implementation of device 305; in which the specific patient 292 has been identified by name 2011; in which the payment reduction is indicated "explicitly" insofar that the indication 2013 includes an audit identifier 2012 that CMS (Centers for Medicare & Medicaid Services, a federal agency within the United States Department of Health and Human Services) associates with payment reductions so that hospitals 201, 202 recognize the significance of the audit; in which one or more such records 561-569 reside in archive 820; and in which such retrieval is "selective" insofar that medical treatment records of other individuals in the same archive 820 are not included in the retrieval. This can occur, for example, in a context in which one or more remote requestors 893, 993 (federal regulators, e.g.) have singled out an individual (patient 292, e.g.) suspected of "excess" institutional readmissions. Under the healthcare system in the United States, for example, Section 3025 of Public Law 111-148 (the "Patient Protection and Affordable Care Act," sometimes called "Obamacare") states that, " . . . beginning on or after Oct. 1, 2012, in order to account for excess readmissions in the hospital, the Secretary [of Health and Human Services] shall reduce the payments that would otherwise be made to such hospital . . . ."

In light of teachings herein, numerous existing techniques may be applied for configuring special-purpose circuitry or other structures effective for managing the accounting for a hospital or other medical provider as described herein without undue experimentation. See, e.g., U.S. Pat. No. 8,065, 162 ("Provider data management and claims editing and settlement system"); U.S. Pat. No. 7,962,350 ("Payment of health care insurance claims using short-term loans"); U.S. Pat. No. 7,860,732 ("Medicare pharmacy calculator II"); U.S. Pat. No. 7,827,234 ("Privacy entitlement protocols for secure data exchange, collection, monitoring and/or alerting"); U.S. Pat. No. 7,805,318 ("Using a non-profit organization to satisfy medicare out-of-pocket/troop and product replacement"); U.S. Pat. No. 7,464,043 ("Computerized method and system for obtaining, storing and accessing medical records"); U.S. Pat. No. 7,433,827 ("System and method for displaying a health status of hospitalized patients"); U.S. Pat. No. 7,263,493 ("Delivering electronic versions of supporting documents associated with an insurance claim"); U.S. Pat. No. 6,655,545 ("Medical code system"); and U.S. Pat. No. 6,000,828 ("Method of improving drug treatment").

Extensive operation 2475 describes retrieving a medical treatment record relating to a set of one or more pathologies selectively in response to an explicit indication of a payment reduction that identifies the set (e.g. retrieval module 342 generating a report 2145 comprising numerous data components 127, 128, 137, 138 relating particularly to a list or set 107 of one or more medical conditions to be extracted from one or more records archives 820, 920 as an automatic response to a report request 2146 that effectively identifies which medical conditions are being audited pursuant to a potential or actual payment reduction). This can occur, for example, in a context in which at least one such condition 180 comprises a pathology 181 associated with one or more specific text strings 2182, 2183 (e.g. "addict" or "stress disorder" listed in the subset of data components 127, 128, 137, 138 comprising the report 2145) and in which the potential or actual payment reduction is implicitly evident in a report type 521 (a readmission audit, e.g.), a request authorization 522 (identifying a federal agency or other office responsible for identifying or preventing payment reductions, e.g.), a user identifier 523 (of a remote requestor 893, 993 who works for Medicare or Medicaid, e.g.), or other such indications 525; in which each data component in records archives 820, 920 includes one or more instances of records 561-569 described herein; and in which such retrieval is "selective" in that it excludes some records (in data component 126, e.g.) that reside in one or more records archives 820 based on their relation to a medical condition 160 that is not of interest. Alternatively or additionally, in some contexts, retrieval module 342 may implement operation 2475 by executing a request (using search term 2180, e.g.) that sets forth one or more pathological conditions 160 (e.g. "injur" or "lacerat" expressed in an "ANDNOT" clause of a search term 2010, 2180) that are to be excluded from the report 2145.

In light of teachings herein, numerous existing techniques may be applied for configuring special-purpose circuitry or other structures effective for retrieving data based on a "condition" description as described herein without undue experimentation. See, e.g., U.S. Pat. No. 7,844,470 ("Treatment order processing system suitable for pharmacy and other use"); U.S. Pat. No. 7,739,126 ("Method, system, and computer program product for physician efficiency measurement and patient health risk stratification"); U.S. Pat. No. 7,707,047 ("Method and system for generating personal/individual health records"); U.S. Pat. No. 7,664,659 ("Displaying clinical predicted length of stay of patients for workload balancing in a healthcare environment"); U.S. Pat. No. 7,640,175 ("Method for high-risk member identification"); U.S. Pat. No. 7,624,027 ("Method and system for automated medical records processing"); U.S. Pat. No. 7,613,620 ("Physician to patient network system for real-time electronic communications and transfer of patient health information"); U.S. Pat. No. 7,444,291 ("System and method for modeling of healthcare utilization"); and U.S. Pat. No. 6,266,645 ("Risk adjustment tools for analyzing patient electronic discharge records").

Figure 25:
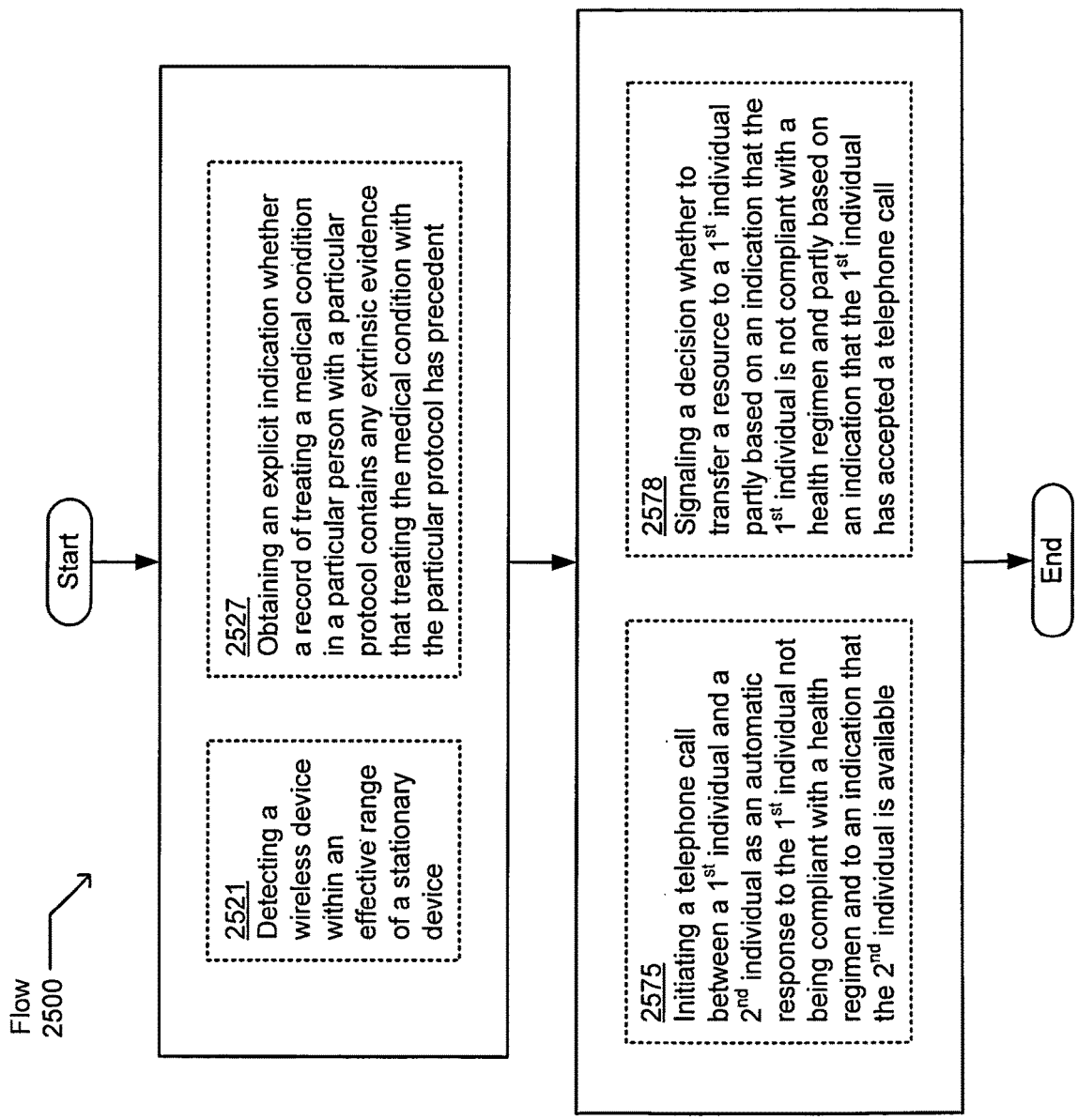
FIG. 25 likewise depicts variants of earlier-presented flows.

With reference now to flow 2500 of FIG. 25 and to other flows 14-19, 2300, 2400 described above, in some variants, one or more of operations 2521, 2527 may be performed in conjunction with intensive operations described above or in preparation for one or more extensive operations described above. Alternatively or additionally, one or more of operations 2575, 2578 may likewise be performed in response to one or more intensive operations described above or in conjunction with extensive operations described above.

Intensive operation 2521 describes detecting a wireless device within an effective range of a stationary device (e.g. detection module 2246 determining that device 2215 is within an effective range of device 2205 by establishing a wireless linkage 2211 with device 2215). This can occur, for example, in a context in which means for performing one or more intensive operations 35-46 as described above include an implementation of device 2205 as a stationary device that also implements device 242 (affixed to a building or other stationary structure, e.g.); in which device 2215 includes one or more media as described above and an implementation of device 305 that does not have a power supply (comprising a passive RFID transponder 397, e.g.); and in which device 2215 is configured to respond to a wireless signal from device 2205 by transmitting a unique wireless signal 2154 recognizable to detection module 2246 if device 2215 is within the effective range (linkage 2211, e.g.) of device 2205. Alternatively or additionally, in some contexts, device 2215 may comprise a passive USID transponder 398 in a system configured as described above, mutatis mutandis.

Intensive operation 2527 describes obtaining an explicit indication whether a record of treating a medical condition in a particular person with a particular protocol contains any extrinsic evidence that treating the medical condition with the particular protocol has precedent (e.g. configuration module 325 receiving one or more yes/no values 2061, 2062 from physicians or other caregivers 991, 1191 in response to one or more queries 2071, 2072 directed to whether a patient's records 671-675 included suitable annotations 2193 of extrinsic evidence in support of any unconventional protocols 130, 140 prescribed or used by the patient 292). This can occur, for example, in a context in which means for performing one or more intensive operations 35-46 as described above include an implementation of device 305; in which configuration module 325 directs such a query to caregivers 991, 1191 who are editing one or more data components 126, 136, 146 of the patient's medical record 674 (relating to one or more protocols 120, 130, 140 being performed, e.g.); in which configuration module 325 is configured to recognize one or more protocols 120 as conventional (standard or normal or common, e.g.); and in which configuration module 325 is configured to accept such evidentiary content 432 (scans 811 or references or annotations 2193, e.g.) documenting any applicable precedent (research studies or reports or prominence indications or anecdotal data, e.g.). In some contexts, configuration module 325 may require such content 432 or an affirmation of its existence (as value 2061, e.g.) before permitting such records 674 to be saved, for example, or before permitting any order for other protocols 130, 140 (for non-emergency treatments, e.g.) to be placed. Alternatively or additionally, configuration module 325 may be operable to send a notification message 2190 to another entity 1091 (a hospital administrator, e.g.) as an automatic response to any unconventional protocol 140 being ordered by any caregiver at a particular hospital 202 unless one or more such values 2061, 2062 are received (concerning extrinsic evidence and precedent, e.g.). In some contexts, moreover, configuration module 325 is itself configurable by such entities 1091 such that each can control what kinds of notice they receive (by selectively subscribing to receive notices of unprecedented protocols 140 being used with or without subscribing to receive notices of unconventional-but-precedented protocols 130 being used, e.g.).

In light of teachings herein, numerous existing techniques may be applied for configuring special-purpose circuitry or other structures effective for searching a collection of health-related treatments as described herein without undue experimentation. See, e.g., U.S. Pat. No. 8,010,664 ("Hypothesis development based on selective reported events"); U.S. Pat. No. 7,991,485 ("System and method for obtaining, processing and evaluating patient information for diagnosing disease and selecting treatment"); U.S. Pat. No. 7,970,552 ("Diagnostic system for selecting nutrition and pharmacological products for animals"); U.S. Pat. No. 7,959,568 ("Advanced patient management for identifying, displaying and assisting with correlating health-related data"); U.S. Pat. No. 7,853,626 ("Computational systems for biomedical data"); U.S. Pat. No. 7,630,762 ("Medical device with resuscitation prompts depending on elapsed time"); U.S. Pat. No. 7,485,095 ("Measurement and analysis of trends in physiological and/or health data"); U.S. Pat. No. 7,181,375 ("Patient data mining for diagnosis and projections of patient states"); and U.S. Pat. No. 6,665,558 ("System and method for correlation of patient health information and implant device data").

Extensive operation 2575 describes initiating a telephone call between a first individual and a second individual as an automatic response to the first individual not being compliant with a health regimen and to an indication that the second individual is available (e.g. response module 358 creating a teleconference session or other phone call 2191 that includes patient 292 and agent 294 in response to an indication 686 that patient 292 is currently not compliant with one or more components 651, 652 of a health regimen 650 contemporaneously with an indication 687 of agent 294 being available to participate in the phone call 2191). This can occur, for example, in a context in which means for performing one or more extensive operations 51-57 as described above include an implementation of device 305; in which agent 294 provides indication 687 explicitly and directly to response module 358 (by clicking an "available" button on a desktop system 841, 941 that implements an auto-dialer, e.g.); in which such components 651, 652 include at least one of a requirement (to use an exercise machine or take particular drugs or nutraceuticals, e.g.) or a restriction (to refrain from smoking, e.g.); and in which one or more devices 2205, 2215 (comprising one or more sensors 2254, e.g.) signal compliance or noncompliance with regimen 650. A sensor activation can signal noncompliance with a regimen component 651 that forbids snacking during certain hours, for example, by detecting a kitchen cupboard 2271 opening. Alternatively or additionally, an implementation of sensor 2254 can detect compliance with a regimen component 652 that requires a task (medication or exercise, e.g.) to be performed during a particular time interval 538 by detecting a movement in something associated with the task (an exercise machine 2273 or drug dispenser actuator 2272 or "task done" button 2279 on a handheld 2274, e.g.).

In light of teachings herein, numerous existing techniques may be applied for configuring special-purpose circuitry or other structures effective for detecting a movement of some or all of a device as described herein without undue experimentation. See, e.g., U.S. Pat. No. 8,082,122 ("Mobile device having a motion detector"); U.S. Pat. No. 7,973,820 ("Motion detector and image capture device, interchangeable lens and camera system including the motion detector"); U.S. Pat. No. 7,967,141 ("Device for the automatic detection of the movement of objects"); U.S. Pat. No. 7,887,493 ("Implantable device employing movement sensing for detecting sleep-related disorders"); U.S. Pat. No. 7,826,310 ("Acoustic navigation device and method of detecting movement of a navigation device"); U.S. Pat. No. 7,635,846 ("Motion detector device with rotatable focusing views and a method of selecting a specific focusing view"); U.S. Pat. No. 7,511,260 ("Encoder device for detecting movement"); U.S. Pat. No. 7,454,299 ("Device and method for detecting an end of a movement of a valve piston in a valve"); and U.S. Pat. No. 6,920,699 ("Device for and method for detecting a relative movement between two machine parts which are movable relative to one another").

Extensive operation 2578 describes signaling a decision whether to transfer a resource to a first individual partly based on an indication that the first individual is not compliant with a health regimen and partly based on an indication that the first individual has accepted a telephone call (e.g. response module 357 transferring credits 693 into an account 616 of patient 292 in response to an indication 685 that patient 292 participated in a phone call 2191 with call center 295 about regimen 650). This can occur, for example, in a context in which an agent 294 of call center 295 participates in the phone call 2191; in which the resource (incentive 694, e.g.) is effective (large enough, e.g.) to motivate a particular patient 292 sometimes to take the call but not large enough to motivate the patient to violate the regimen 650; and in which a primary purpose of call center 295 is to initiate such telephone calls in response to one or more signals 2153 (a device-generated notification or webcam feed, e.g.) directly or indirectly indicating that a patient 292 is apparently noncompliant with a time-critical component 651 (relating to dosages of an antibiotic, e.g.) of regimen 650. This can occur, for example, in a context in which patient 292 complies with the regimen component 651 in a portion of the patient's home 289 that the call center agent 294 can monitor (via a camera 2253, microphone, or other sensor 2254, e.g.); in which patient 292 has been informed of the incentives 694; in which an instance of device 305, 2205 as described above resides in the patient's home 289 and on one or more networks described above; and in which response module 357 performs operation 2578 by causing food or other goods 691 to be provided to patient 292 (delivered to the patient's home 289 by a third-party supplier who receives an order 618 from response module 357, e.g.) as an automatic response to patient 292 accepting the phone call from call center 295. Alternatively or additionally, an instance of device 305 may be configured to deliver such goods 691 (in a dispensing machine 2230 at the patient's home, e.g.).

In light of teachings herein, numerous existing techniques may be applied for configuring special-purpose circuitry or other structures effective for determining whether someone has accepted a telephone call as described herein without undue experimentation. See, e.g., U.S. Pat. No. 7,680,260

("Detecting a voice mail system answering a call"); U.S. Pat. No. 7,386,101 ("System and method for call answer determination for automated calling systems"); U.S. Pat. No. 7,260,205 ("Call waiting using external notification and presence detection"); U.S. Pat. No. 6,738,613 ("Telephone set having automatic incoming-call acknowledgement detection"); U.S. Pat. No. 6,697,456 ("Speech analysis based answer detection for IP based telephones"); U.S. Pat. No. 6,650,751 ("Answer detection for IP based telephones using passive detection"); and U.S. Pat. No. 6,111,946 ("Method and system for providing answer supervision in a switched telephone network").

In light of teachings herein, numerous existing techniques may be applied for configuring special-purpose circuitry or other structures effective for causing a vending machine actuation or other delivery of goods as described herein without undue experimentation. See, e.g., U.S. Pat. No. 8,068,933 ("Products and processes for vending a plurality of products via defined groups"); U.S. Pat. No. 8,041,454 ("Automated business system and method of vending and returning a consumer product"); U.S. Pat. No. 8,002,144 ("Drive system for a vending machine dispensing assembly"); U.S. Pat. No. 7,844,363 ("Vending machine apparatus to dispense herbal medications and prescription medicines"); U.S. Pat. No. 7,783,379 ("Automated vending of products containing controlled substances"); U.S. Pat. No. 7,753,091 ("Device and method for controlling the filling of a cup by a vending machine"); U.S. Pat. No. 7,536,360 ("Electronic purchase of goods over a communications network including physical delivery while securing private and personal information of the purchasing party"); U.S. Pat. No. 7,272,571 ("Method and apparatus for effective distribution and delivery of goods ordered on the World-Wide-Web"); U.S. Pat. No. 6,799,165 ("Apparatus and methods for inventory, sale, and delivery of digitally transferable goods"); and U.S. Pat. No. 6,536,189 ("Computerized, monitored, temperature affected, delivery system for perishable goods").

With reference now to flow 2600 of FIG. 26 and to other flows 14-19, 2300, 2400, 2500 described above, in some variants, one or more of operations 2621, 2623 may be performed in conjunction with intensive operations described above or in preparation for one or more extensive operations described above. Alternatively or additionally, one or more of operations 2674, 2677 may likewise be performed in response to one or more intensive operations described above or in conjunction with extensive operations described above.

Intensive operation 2621 describes causing a locally-resident subscriber registry to be updated (e.g. invocation module 371 triggering update module 2228 to remove an identifier 733 of the individual from a registry 109 stored on a medium 105 in service zone 207 in response to an indication 683 that the individual is not in service zone 207). This can occur, for example, in a context in which the individual is a patient 292, 1292 as described herein; in which service zone 207 is a defined region (a county or metropolitan area, e.g.); in which device 2205 is on network 290; in which device 2215 is held or worn by patient 292; in which invocation module 371 detects that patient 292 left service zone 207 by receiving an indication that patient 292 is now in another service zone 208 (at home 289, e.g.); and in which invocation module 371 responds by transmitting a request 772 for the removal of the individual from the registry 109. Alternatively or additionally, invocation module 371 and detection module 2244 may be configured jointly to determine whether the individual is still in service zone 207 simply by detecting whether device 2215 (worn or carried by the individual, e.g.) is within a direct operating range of device 2205. Alternatively or additionally, invocation module 371 may be configured to invoke one or more other functional modules as described with reference to flows herein.

Intensive operation 2623 describes determining whether a portable device is in a vicinity of another device (e.g. detection module 2241 detecting whether two devices 2205, 2215 are close enough that a sensor 2254 in one can directly detect a transponder 1225 or other detectable structure 2275 of the other). This can occur, for example, in a context in which means for performing one or more intensive operations 35-46 as described above include an implementation of device 2205; in which one or both devices 2205, 2215 implement an instance of device 305; in which detection module 2241 is configured to receive a signal 2152 from sensor 2254; in which such detection is "direct" insofar that a wireless linkage 2211 between the devices 2205, 2215 consists of free space or other passive media (air, e.g.); and in which one or both devices 2205, 2215 are portable (configured to be worn or carried in one hand, e.g.). In some contexts, for example, a camera 2253 can transmit a signal 2152 (image, e.g.) indicating a detectable structure 2275 (a barcode or other visible feature that is unique to device 2215, e.g.) that detection module 2241 is configured to recognize. Alternatively or additionally, one or more other devices 241, 242 may be configured (e.g. as a tower or satellite or wall-mounted device 1343, e.g.) to perform operation 2623 by detecting both devices 2205, 2215 in a common location 204, 1304 simultaneously and the two devices are "in a vicinity" of one another insofar that both are within 50 meters of the same point (e.g. at a "third" device 241, 242).

In light of teachings herein, numerous existing techniques may be applied for configuring special-purpose circuitry or other structures effective for determining by wireless communication which devices are in a region as described herein without undue experimentation. See, e.g., U.S. Pat. No. 8,064,884 ("System and method for provisioning a wireless device to only be able to access network services within a specific location"); U.S. Pat. No. 8,010,126 ("Surveying wireless device users by location"); U.S. Pat. No. 7,983,677 ("Location-based wireless messaging for wireless devices"); U.S. Pat. No. 7,979,086 ("Virtual visitor location register for a wireless local area network"); U.S. Pat. No. 7,809,378 ("Location visit detail services for wireless devices"); U.S. Pat. No. 7,548,158 ("First responder wireless emergency alerting with automatic callback and location triggering"); U.S. Pat. No. 7,539,500 ("Using cell phones and wireless cellular systems with location capability for toll paying and collection"); U.S. Pat. No. 7,385,516 ("Location visit confirmation services for wireless devices"); U.S. Pat. No. 7,068,992 ("System and method of polling wireless devices having a substantially fixed and/or predesignated geographic location"); and U.S. Pat. No. 6,957,076 ("Location specific reminders for wireless mobiles").

Extensive operation 2674 describes responding to an event with an audible notification (e.g. response module 353 causing speaker 2257 to signal a caregiver 1291, 1391 or other entity 1091 when one or more intensive operations 35-46 are completed). This can occur, for example, in a context in which a device 305 or system 841, 941 described above includes an implementation of device 2205. Alternatively or additionally, response module 353 may comprise one or more of the means for performing extensive operations 51-57 as described above.

In light of teachings herein, numerous existing techniques may be applied for configuring special-purpose circuitry or other structures effective for implementing a device-initiated phone call or other audible notification as described herein without undue experimentation. See, e.g., U.S. Pat. No. 8,041,017 ("Emergency call service with automatic third party notification and/or bridging"); U.S. Pat. No. 7,650,811 ("Shifting device"); U.S. Pat. No. 7,508,298 ("Automatic crash notification using prerecorded messages"); U.S. Pat. No. 7,493,281 ("Automatic notification of irregular activity"); U.S. Pat. No. 7,469,155 ("Handheld communications device with automatic alert mode selection"); U.S. Pat. No. 7,181,192 ("Handheld portable automatic emergency alert system and method"); U.S. Pat. No. 7,076,235 ("Automatic notification of personal emergency contacts from a wireless communications device"); U.S. Pat. No. 6,442,485 ("Method and apparatus for an automatic vehicle location, collision notification, and synthetic voice"); and U.S. Pat. No. 6,112,074 ("Radio communication system with automatic geographic event notification").

Extensive operation 2677 describes responding to a payment-reduction event relating to a first medical treatment by causing a selective retrieval of one or more records that lack any prominence indication relating to the first medical treatment from an archive that includes at least one prominence indication relating to a second medical treatment (e.g. response module 352 responding to a request 582 for records 565, 566 indicating that protocol 120 was administered but that lack any prominence indications 1126, 1127 relating to protocol 120). This can occur, for example, in a context in which request 582 comprises a message from an entity that pays for at least some of the first medical treatment (Medicare or Medicaid, e.g.) such as remote requestor 893 (an auditor or regulator, e.g.); in which a report type 521, request authorization 522, or other such indication 525 signals a potential or actual payment-reduction event (manifesting a reduction that has resulted or may result from a failure to justify the use of protocol 120 in treating one or more specific medical conditions 160, e.g.) and in which a single order 1018 for protocol 120 does not constitute a "prominence indication" for purposes of determining whether the use of protocol 120 itself should be scrutinized (made subject to a payment reduction, e.g.). Alternatively or additionally, response module 352 may invoke one or more retrieval modules 825, 925 configured to access at least one records archive 920 that contains a prominence indication 1137 (average evaluation 1053 or use count 1054, e.g.) for another protocol 130.

In light of teachings herein, numerous existing techniques may be applied for configuring special-purpose circuitry or other structures effective for identifying records relating to an unjustified action as described herein without undue experimentation. See, e.g., U.S. Pat. No. 7,793,835 ("System and method for identity-based fraud detection for transactions using a plurality of historical identity records"); U.S. Pat. No. 7,668,843 ("Identification of anomalous data records"); U.S. Pat. No. 7,650,321 ("Two classifier based system for classifying anomalous medical patient records"); U.S. Pat. No. 7,493,281 ("Automatic notification of irregular activity"); U.S. Pat. No. 6,944,599 ("Monitoring and automatic notification of irregular activity in a network-based transaction facility"); and U.S. Pat. No. 6,636,592 ("Method and system for using bad billed number records to prevent fraud in a telecommunication system").

With reference now to flow 2700 of FIG. 27 and to other flows 14-19, 2300, 2400, 2500, 2600 described above, in some variants, one or more of operations 2724, 2729 may be performed in conjunction with intensive operations described above or in preparation for one or more extensive operations described above. Alternatively or additionally, one or more of operations 2772, 2773, 2776 may likewise be performed in response to one or more intensive operations described above or in conjunction with extensive operations described above.

Intensive operation 2724 describes detecting a passive wireless transponder within a vicinity of a vehicle (e.g. detection module 2243 receiving a return signal 2151 from a passive device implementing a radio frequency identification transponder 397 or an ultrasound identification transponder 398). This can occur, for example, in a context in which medium 2105 comprises the passive device (a semiconductor chip or other device lacking a power supply 2258, e.g.); in which one or more detection modules 2241-2246 reside aboard an ambulance 1295 (in device 1241, e.g.) or other vehicle (in device 241, e.g.); and in which means for performing one or more intensive operations 35-46 as described above include an implementation of device 2205. Alternatively or additionally, detection module 2243 (implemented in a stationary device 242, e.g.) may be configured to perform operation 2724 by detecting a passive wireless transponder that is aboard the vehicle (in device 1241, e.g.).

In light of teachings herein, numerous existing techniques may be applied for configuring special-purpose circuitry or other structures effective for configuring a portable device to detect a passive wireless transponder as described herein without undue experimentation. See, e.g., U.S. Pat. No. 8,074,007 ("Passive client-host detection for connected peripherals"); U.S. Pat. No. 8,072,310 ("System for detecting and measuring parameters of passive transponders"); U.S. Pat. No. 8,045,929 ("Determining presence of radio frequency communication device"); U.S. Pat. No. 7,978,639 ("Systems, methods and devices for collecting data from wireless sensor nodes"); U.S. Pat. No. 7,969,143 ("Method of tracking an object having a passive transponder attached thereto"); U.S. Pat. No. 7,725,253 ("Tracking, auto-calibration, and map-building system").

Intensive operation 2729 describes obtaining an indication whether an individual is compliant with a health regimen (e.g. input module 318 receiving timing data 453 relating to when a patient is taking medications at home). This can occur, for example, in a context in which one or more caregivers 991, 1191 prescribe a home care regimen 650 and in which one or more particular components 652 of the regimen (antibiotics or other medications, e.g.) are crucial to a favorable outcome for a specific patient 292. Alternatively or additionally, input module 318 may be configured to provide additional data relevant to a determination of regimen compliance (raw data 712 with one or more timestamps 711 from a sensor 2254 in the patient's home 289, e.g.) into the patient's record 673. This can occur, for example, in a context in which there are one or more indications 685 (diagnostic data 490 or protocol data 450, e.g.) that an institutional readmission has resulted from a behavior of a patient 292 or at-home caregiver and not from anything that occurred earlier (while in-patient at hospital 201, e.g.).

In light of teachings herein, numerous existing techniques may be applied for configuring special-purpose circuitry or other structures effective for generating indications of patient compliance or noncompliance as described herein without undue experimentation. See, e.g., U.S. Pat. No. 8,032,399 ("Treatment regimen compliance and efficacy with feedback"); U.S. Pat. No. 7,917,377 ("Patient data mining for automated compliance"); U.S. Pat. No. 7,599,892

("Method for secure diagnostic screening, servicing, treatment, and compliance monitoring for sleep apnea in truck drivers"); U.S. Pat. No. 7,417,205 ("Medical item thermal treatment systems and method of monitoring medical items for compliance with prescribed requirements"); U.S. Pat. No. 6,926,667 ("Patient compliance monitor"); U.S. Pat. No. 6,790,668 ("Monitoring patient compliance and bioavailability of drugs by deproteinizing body fluids"); U.S. Pat. No. 6,380,858 ("Systems and methods for monitoring patient compliance with medication regimens"); U.S. Pat. No. 6,161,095 ("Treatment regimen compliance and efficacy with feedback"); U.S. Pat. No. 6,124,136 ("Method of monitoring compliance with methadone treatment program"); and U.S. patent application Ser. No. 13/199,053 ("Systematic distillation of status data relating to regimen compliance").

Extensive operation 2772 describes triggering a search of a particular records archive by providing a selective search criterion, one that results in an exclusion of a first element in the particular records archive and an inclusion of a second element in the particular records archive (e.g. retrieval module 344 transmitting a search term 2010 to search engine 2098 that searches records archive 820 and generates a search result 2030 that excludes one or more data components 138 therein and includes one or more other data components 126 therein). This can occur, for example, in a context in which search term 2010 identifies one or more selective inclusion criteria 2001 (e.g. words or codes identifying condition 160) and one or more selective exclusion criteria 2002 (e.g. words or codes identifying protocols 130, 140). Alternatively or additionally, retrieval module 344 may be configured to trigger a search of other search records archive 920 (by invoking retrieval module 925, e.g.) and to include the result 2030 (in report 2144, e.g.).

In light of teachings herein, numerous existing techniques may be applied for configuring special-purpose circuitry or other structures effective for performing selective data retrieval as described herein without undue experimentation. See, e.g., U.S. Pat. No. 8,068,603 ("Focused retrieval of selected data in a call center environment"); U.S. Pat. No. 7,966,532 ("Method for selectively retrieving column redundancy data in memory device"); U.S. Pat. No. 7,203,633 ("Method and system for selectively storing and retrieving simulation data utilizing keywords"); U.S. Pat. No. 6,519,327 ("System and method for selectively retrieving messages stored on telephony and data networks"); U.S. Pat. No. 6,421,726 ("System and method for selection and retrieval of diverse types of video data on a computer network"); U.S. Pat. No. 6,185,573 ("Method and system for the integrated storage and dynamic selective retrieval of text, audio and video data"); U.S. Pat. No. 6,137,914 ("Method and format for storing and selectively retrieving image data"); and U.S. Pat. No. 6,094,573 ("System and a method for selective data retrieval from a remote database on basis of caller line identification and user specific access codes").

Extensive operation 2773 describes transmitting a real-time notification to a first person as an automatic response to an interface in a vicinity of a second person detecting a particular event relating to the second person (e.g. update module 2229 transmitting one or more records 561-569, 671-675 or other data components 136-138 to the "first" person upon detecting an input 551, 552 or other action taken by the "second" person). This can occur, for example, in a context in which the "first" person is a caregiver 991, 1191, 1291 or patient 292, 992 or administrator (a call center agent 294 or other entity 1091, e.g.); in which the interface comprises one or more of the above-described devices; in which such data components 136-138 relate to the "second" person or to device 2205; in which the "particular event" comprises device 2215 entering a detection range of something carried or worn by the "second" person (manifesting the vicinity of the 2nd person, e.g.); and in which means for performing one or more extensive operations 51-57 as described above include an implementation of device 2205. Alternatively or additionally, update module 2229 may be configured to transmit such a notification (using an e-mail address 721 or telephone number 722, e.g.) in response to a "particular event" occurring within device 305 (comprising one or more computation or detection events described herein or a combination thereof, e.g.). In some contexts, for example, update module 2229 may be configured to respond to one or more records 561-569, 671-675 as described herein being saved without a prominence indication or annotation 2193 (in a context in which the "second" person is a caregiver failing to document an unconventional treatment being ordered, e.g.).

In light of teachings herein, numerous existing techniques may be applied for configuring special-purpose circuitry or other structures effective for implementing a real-time notification as described herein without undue experimentation. See, e.g., U.S. Pat. No. 8,060,562 ("Real time update notification"); U.S. Pat. No. 7,940,602 ("Real-time system and method of underwater depth discrepancy detection, recordation and alarm notification"); U.S. Pat. No. 7,924,149 ("System and method for providing alarming notification and real-time, critical emergency information to occupants in a building or emergency designed area and evacuation guidance system to and in the emergency exit route"); U.S. Pat. No. 7,899,739 ("Construction payment management system and method with real-time draw notification features"); U.S. Pat. No. 7,898,423 ("Real-time event notification"); U.S. Pat. No. 7,890,622 ("Real-time notification of device events"); U.S. Pat. No. 7,865,566 ("Method and apparatus for providing real-time notification for avatars"); U.S. Pat. No. 7,835,506 ("Method and system for real-time notification and disposition of voice services in a cable services network"); U.S. Pat. No. 7,813,481 ("Conversation recording with real-time notification for users of communication terminals"); U.S. Pat. No. 7,617,162 ("Real time push notification in an event driven network"); and U.S. Pat. No. 7,319,378 ("Anti-theft system for a vehicle with real-time notification feature").

Extensive operation 2776 describes implementing a failsafe preventing medical equipment from operating until an order associating the medical equipment with a patient is received and until an indication is received that the patient is in a vicinity of the medical equipment (e.g. detection module 2245 enabling medical equipment 2280 to function only after receiving a report 2143 or other indication 688 that an authorized caregiver has generated such an order and only after detecting that the specific patient 292, 1392 is in a vicinity of the medical equipment 2280). This can occur, for example, in a context in which one or more orders 1018, 618 as described above call for particular diagnostic data 490 in relation to patient 292; in which such orders explicitly or implicitly identify the equipment 2280 (corresponding to a particular biometric 481, test result 482, computed tomography scan 483, or other image 484, e.g.) in association with the patient for whom they are to be obtained; in which detection module 2245 is configured to determine whether a location or device that includes a patient identifier 731, 1331 is in a vicinity of the equipment 2280; and in which detection module 2245 receives indication 688 via input module 314. This can occur, for example, in a context in which one or more detection modules 2241-2246 are mounted on the equipment 2280 or in the same room (as a stationary instance of equipment 2280, e.g.). In some contexts, moreover, a single device 305 or room (office or server room, e.g.) or facility (hospital 201, e.g.) may be configured to contain an entire system described herein. Alternatively or additionally, an instance of detection module 2245 configured to detect equipment 2280 may reside on the specific patient 292 or in a location associated with the patient 292 (in the patient's room, e.g.). Alternatively or additionally, module 314 may be configured to receive other data (one or more of indications 681-687, e.g.) on data-handling media 105, 405, 505, 605, 705, 2005, 2105 as described herein.

In light of teachings herein, numerous existing techniques may be applied for configuring special-purpose circuitry or other structures effective for implementing a medical equipment failsafe as described herein without undue experimentation. See, e.g., U.S. Pat. No. 8,083,406 ("Diagnostic Delivery Service"); U.S. Pat. No. 8,070,739 ("Liquid drug transfer devices for failsafe correct snap fitting onto medicinal vials"); U.S. Pat. No. 8,068,917 ("Fail-safe programming for implantable medical device"); U.S. Pat. No. 7,752,058 ("Portable terminal and health management method and system using portable terminal"); U.S. Pat. No. 7,696,751 ("Method and apparatus for ferrous object and/or magnetic field detection for MRI safety"); U.S. Pat. No. 7,438,072 ("Portable field anesthesia machine and control therefore"); U.S. Pat. No. 7,087,036 ("Fail safe system for operating medical fluid valves"); U.S. Pat. No. 7,034,934 ("Anti-carcinogenic lights and lighting"); U.S. Pat. No. 6,768,420 ("Vehicle compartment occupancy detection system"); and U.S. Pat. No. 6,366,809 ("Defibrillator battery with memory and status indication gauge").

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will, be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

With respect to the numbered clauses and claims expressed below, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise. Also in the numbered clauses below, specific combinations of aspects and embodiments are articulated in a shorthand form such that (1) according to respective embodiments, for each instance in which a "component" or other such identifiers appear to be introduced (with "a" or "an," e.g.) more than once in a given chain of clauses, such designations may either identify the same entity or distinct entities; and (2) what might be called "dependent" clauses below may or may not incorporate, in respective embodiments, the features of "independent" clauses to which they refer or other features described above.

CLAUSES 1. (Independent) A healthcare information management system comprising:
   circuitry for obtaining an indication of a first device associated with and wearable by a patient hospitalized for a particular condition;
   circuitry for obtaining an indication of a second device associated with and wearable by a caregiver;
   circuitry for causing a recordation of a timestamp as an automatic response to the first device associated with and wearable by the patient and the second device associated with and wearable by the caregiver both being in a single common location; and
   circuitry for causing a retrieval of the timestamp in response to an indication of an institutional readmission after the recordation of the timestamp indicating the first device associated with and wearable by the patient and the second device associated with and wearable by the caregiver both having been in the single common location.

2. The healthcare information management system of any of the above SYSTEM CLAUSES, further comprising:
   circuitry for receiving a communication delay as data entered by a user.

3. The system of CLAUSE 2 in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
   circuitry for transmitting a query as an automatic response to an expiration of the communication delay.

4. The healthcare information management system of any of the above SYSTEM CLAUSES, further comprising:
   circuitry for looking up a communication delay as a function of a therapeutic protocol.

5. The system of CLAUSE 4 in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
   circuitry for transmitting a query as an automatic response to an expiration of the communication delay.

6. The healthcare information management system of any of the above SYSTEM CLAUSES, further comprising:
   circuitry for looking up a communication delay as a function of a medical condition.

7. The system of CLAUSE 6 in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
   circuitry for transmitting a query as an automatic response to an expiration of the communication delay.

8. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
   circuitry for causing an individual to be contacted by a fallback mode of communication as a conditional response to receiving no reply from the individual by a prior mode of communication, the prior mode of communication being telephonic.

9. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
   circuitry for contacting an individual by a fallback mode of communication as an automatic and conditional response to receiving no reply from the individual by a prior mode of communication, the fallback mode of communication being telephonic.

10. The healthcare information management system of any of the above SYSTEM CLAUSES, further comprising:
    circuitry for updating a locally-resident subscriber registry in response to an individual entering a service zone.

11. The healthcare information management system of any of the above SYSTEM CLAUSES, further comprising:
    circuitry for obtaining an indication that a specific pathology in a particular individual has been treated at a first hospital and an indication that the specific pathology in the particular individual has been treated at a second hospital.

12. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
    circuitry for retrieving a medical treatment record of one individual selectively in response to an explicit indication of a payment reduction that identifies the one individual.

13. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:
    circuitry for retrieving a medical treatment record relating to a set of one or more pathologies selectively in response to an explicit indication of a payment reduction that identifies the set.

14. The healthcare information management system of any of the above SYSTEM CLAUSES, further comprising:
    circuitry for detecting a wireless device within an effective range of a stationary device.

15. The healthcare information management system of any of the above SYSTEM CLAUSES, further comprising:
    circuitry for obtaining an explicit indication whether a record of treating a medical condition in a particular person with a particular protocol contains any extrinsic evidence that treating the medical condition with the particular protocol has precedent.

16. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for initiating a telephone call between a first individual and a second individual as an automatic response to the first individual not being compliant with a health regimen and to an indication that the second individual is available.

17. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for signaling a decision whether to transfer a resource to a first individual partly based on an indication that the first individual is not compliant with a health regimen and partly based on an indication that the first individual has accepted a telephone call.

18. The healthcare information management system of any of the above SYSTEM CLAUSES, further comprising:

circuitry for causing a locally-resident subscriber registry to be updated.

19. The healthcare information management system of any of the above SYSTEM CLAUSES, further comprising:

circuitry for determining whether a portable device is in a vicinity of another device.

20. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for responding to an event with an audible notification.

21. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for responding to a payment-reduction event relating to a first medical treatment by causing a selective retrieval of one or more records that lack any prominence indication relating to the first medical treatment from an archive that includes at least one prominence indication relating to a second medical treatment.

22. The healthcare information management system of any of the above SYSTEM CLAUSES, further comprising:

circuitry for detecting a passive wireless transponder within a vicinity of a vehicle.

23. The healthcare information management system of any of the above SYSTEM CLAUSES, further comprising:

circuitry for obtaining an indication whether an individual is compliant with a health regimen.

24. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for triggering a search of a particular records archive by providing a selective search criterion, one that results in an exclusion of a first element in the particular records archive and an inclusion of a second element in the particular records archive.

25. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for transmitting a real-time notification to a first person as an automatic response to an interface in a vicinity of a second person detecting a particular event relating to the second person.

26. The healthcare information management system of any of the above SYSTEM CLAUSES in which the circuitry for causing a retrieval of the timestamp in response to an indication of an institutional readmission after the recordation of the timestamp indicating the first device associated with and wearable by the patient and the second device associated with and wearable by the caregiver both having been in the single common location comprises:

circuitry for implementing a failsafe preventing medical equipment from operating until an order associating the medical equipment with a patient is received and until an indication is received that the patient is in a vicinity of the medical equipment.

27. (Independent) A healthcare information management method comprising:

obtaining an indication of a first device associated with and wearable by a patient hospitalized for a particular condition;

obtaining an indication of a second device associated with and wearable by a caregiver;

causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location.

28. The healthcare information management method of any of the above METHOD CLAUSES, further comprising:

receiving a communication delay as data entered by a user.

29. The healthcare information management method of any of the above METHOD CLAUSES, further comprising:

looking up a communication delay as a function of a therapeutic protocol.

30. The healthcare information management method of any of the above METHOD CLAUSES, further comprising:

looking up a communication delay as a function of a medical condition.

31. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

causing an individual to be contacted by a fallback mode of communication as a conditional response to receiving no reply from the individual by a prior mode of communication, the prior mode of communication being telephonic.

32. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

contacting an individual by a fallback mode of communication as an automatic and conditional response to receiving no reply from the individual by a prior mode of communication, the fallback mode of communication being telephonic.

33. The healthcare information management method of any of the above METHOD CLAUSES, further comprising:

updating a locally-resident subscriber registry in response to an individual entering a service zone.

34. The healthcare information management method of any of the above METHOD CLAUSES, further comprising:

obtaining an indication that a specific pathology in a particular individual has been treated at a first hospital and an indication that the specific pathology in the particular individual has been treated at a second hospital.

35. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

retrieving a medical treatment record of one individual selectively in response to an explicit indication of a payment reduction that identifies the one individual.

36. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

retrieving a medical treatment record relating to a set of one or more pathologies selectively in response to an explicit indication of a payment reduction that identifies the set.

37. The healthcare information management method of any of the above METHOD CLAUSES, further comprising:

detecting a wireless device within an effective range of a stationary device.

38. The healthcare information management method of any of the above METHOD CLAUSES, further comprising:

obtaining an explicit indication whether a record of treating a medical condition in a particular person with a particular protocol contains any extrinsic evidence that treating the medical condition with the particular protocol has precedent.

39. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

initiating a telephone call between a first individual and a second individual as an automatic response to the first individual not being compliant with a health regimen and to an indication that the second individual is available.

40. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

signaling a decision whether to transfer a resource to a first individual partly based on an indication that the first individual is not compliant with a health regimen and partly based on an indication that the first individual has accepted a telephone call.

41. The healthcare information management method of any of the above METHOD CLAUSES, further comprising:

causing a locally-resident subscriber registry to be updated.

42. The healthcare information management method of any of the above METHOD CLAUSES, further comprising:

determining whether a portable device is in a vicinity of another device.

43. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

responding to an event with an audible notification.

44. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

responding to a payment-reduction event relating to a first medical treatment by causing a selective retrieval of one or more records that lack any prominence indication relating to the first medical treatment from an archive that includes at least one prominence indication relating to a second medical treatment.

45. The healthcare information management method of any of the above METHOD CLAUSES, further comprising:

detecting a passive wireless transponder within a vicinity of a vehicle.

46. The healthcare information management method of any of the above METHOD CLAUSES, further comprising:

obtaining an indication whether an individual is compliant with a health regimen.

47. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

triggering a search of a particular records archive by providing a selective search criterion, one that results in an exclusion of a first element in the particular records archive and an inclusion of a second element in the particular records archive.

48. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises:

transmitting a real-time notification to a first person as an automatic response to an interface in a vicinity of a second person detecting a particular event relating to the second person.

49. The healthcare information management method of any of the above METHOD CLAUSES in which the causing a retrieval of the timestamp in response to an indication of an institutional readmission after the recordation of the timestamp indicating the first device associated with and wearable by the patient and the second device associated with and wearable by the caregiver both having been in the single common location comprises: implementing a failsafe preventing medical equipment from operating until an order associating the medical equipment with a patient is received and until an indication is received that the patient is in a vicinity of the medical equipment.

50. (Independent) A healthcare information management method comprising:

causing an electronic record of a first protocol for a particular condition to be annotated with a scan of a document; and retrieving the electronic record of the first protocol after the electronic record of the first protocol is annotated with the scan of the document partly based on an indication of a first patient undergoing the first protocol and partly based on an indication of an institutional readmission.

51. The healthcare information management method of CLAUSE 50 further comprising:

performing the operation(s) of any one or more of the above METHOD CLAUSES that depend from METHOD CLAUSE 27.

52. (Independent) A healthcare information management method comprising:

obtaining an indication that a particular condition was treated in a first patient with a first protocol;

causing a record of a second patient to include the indication that the particular condition was treated in the first patient with the first protocol; and retrieving the record of the second patient selectively in response to an association between the second patient and an indication of an institutional readmission after the record of the second patient includes the indication that the particular condition was treated in the first patient with the first protocol.

53. The healthcare information management method of CLAUSE 52 further comprising:

performing the operation(s) of any one or more of the above METHOD CLAUSES that depend from METHOD CLAUSE 27.

54. (Independent) A healthcare information management method comprising:

obtaining an indication of a first protocol being employed in relation to a particular condition in a first patient;

requesting an effectiveness indication of the first protocol from an entity partly based on the entity validating the first protocol and partly based on a first communication delay associated with the first protocol, the first communication delay exceeding one hour; and signaling a decision whether to update a prominence indication of the first protocol in response to whether the effectiveness indication of the first protocol was received from the entity after the effectiveness indication is requested from the entity partly based on the entity validating the first protocol and partly based on the first communication delay associated with the first protocol.

55. The healthcare information management method of CLAUSE 54 further comprising:

performing the operation(s) of any one or more of the above METHOD CLAUSES that depend from METHOD CLAUSE 27.

56. (Independent) A healthcare information management method comprising:

obtaining an association between a particular condition and a first protocol;

causing a comparison between a threshold and a prominence indication of treating the particular condition with the first protocol after the association between the particular condition and the first protocol is obtained; and signaling a decision whether to caution a caregiver partly based on the association between the particular condition and the first protocol and partly based on the comparison between the threshold and the prominence indication of treating the particular condition with the first protocol.

57. The healthcare information management method of CLAUSE 56 further comprising:

performing the operation(s) of any one or more of the above METHOD CLAUSES that depend from METHOD CLAUSE 27.

58. (Independent) A healthcare information management method comprising:

obtaining an association between a care administration space and a first device;

obtaining via a second device a patient consent conditionally authorizing a release of a first medical record, the second device being a mobile device; and causing the first device to receive the first medical record partly based on the second device entering the care administration space and partly based on the patient consent authorizing the release of the first medical record.

59. The healthcare information management method of CLAUSE 58 further comprising:

performing the operation(s) of any one or more of the above METHOD CLAUSES that depend from METHOD CLAUSE 27.

60. (Independent) A system comprising:

means for performing the operation(s) of any one or more of the above METHOD CLAUSES.

61. (Independent) An article of manufacture comprising:

one or more physical media configured to bear a device-detectable implementation of a method including at least obtaining an indication of a first device associated with and wearable by a patient hospitalized for a particular condition;

obtaining an indication of a second device associated with and wearable by a caregiver;

causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location.

62. The article of manufacture of CLAUSE 61 in which a portion of the one or more physical media comprises:

one or more signal-bearing media configured to transmit one or more instructions for performing the operation(s) of any one or more of the above METHOD CLAUSES.

63. (Independent) An article of manufacture comprising:

one or more physical media bearing a device-detectable output indicating an occurrence of obtaining an indication of a first device associated with and wearable by a patient hospitalized for a particular condition;

obtaining an indication of a second device associated with and wearable by a caregiver;

causing a recordation of a timestamp as an automatic response to the first device associated with and wearable by the patient and the second device associated with and wearable by the caregiver both being in a single common location; and causing a retrieval of the timestamp in response to an indication of an institutional readmission after the recordation of the timestamp indicating the first device associated with and wearable by the patient and the second device associated with and wearable by the caregiver both having been in the single common location.

64. The article of manufacture of CLAUSE 63 in which a portion of the one or more physical media comprises:

one or more signal-bearing media configured to transmit one or more instructions for performing the operation(s) of any one or more of the above METHOD CLAUSES.

65. The article of manufacture of CLAUSE 63 in which at least one of the one or more physical media comprises:

one or more signal-bearing media bearing at least one signal from an implementation having at least circuitry for causing a retrieval of the timestamp in response to an indication of an institutional readmission after the recordation of the timestamp indicating the first device associated with and wearable by the patient and the second device associated with and wearable by the caregiver both having been in the single common location.

All of the patents and other publications referred to above are incorporated herein by reference generally—including those identified in relation to particular new applications of existing techniques—to the extent not inconsistent herewith (in each respective latest edition, where applicable). While various system, method, article of manufacture, or other embodiments or aspects have been disclosed above, also, other combinations of embodiments or aspects will be apparent to those skilled in the art in view of the above disclosure. The various embodiments and aspects disclosed above are for purposes of illustration and are not intended to be limiting, with the true scope and spirit being indicated in the final claim set that follows.

What is claimed is:

1. A healthcare information management system comprising:

circuitry configured for detecting a personal mobile device identified by at least one device identifier within an effective range of at least one wireless transceiver associated with at least one healthcare administration space;

circuitry configured for associating a patient with at least one patient identifier, the patient associated with the personal mobile device identified by the at least one device identifier;

circuitry configured for causing a recordation of at least one indication of presence of the patient associated with the at least one patient identifier in the at least one healthcare administration space in at least one patient file indicating at least the patient having a particular condition, wherein the causing a recordation is an automatic response to the detection of the personal mobile device within the effective range of the at least one wireless transceiver associated with the at least one healthcare administration space;

circuitry configured for identifying at least one protocol associated with the patient and associated with the particular condition based at least partly on the at least one patient file associated with the patient, the at least one protocol associated with at least one medical equipment located within the effective range of the at least one wireless transceiver associated with the at least one healthcare administration space, the at least one medical equipment implementing a failsafe that prevents the at least one medical equipment from operating until enabled; and circuitry configured for enabling the at least one medical equipment associated with the identified at least one protocol to function including at least overriding the failsafe as an automatic response to the identification of the at least one protocol and the detection of the personal mobile device within the effective range of the at least one wireless transceiver associated with at least one healthcare administration space.

2. The healthcare information management system of claim 1, wherein the circuitry configured for detecting a personal mobile device identified by at least one device identifier within an effective range of at least one wireless transceiver associated with at least one healthcare administration space comprises:

circuitry configured for detecting the personal mobile device assigned to the patient and a second device assigned to a caregiver within a detection range of the at least one wireless transceiver associated with the at least one healthcare administration space.

3. The healthcare information management system of claim 1, wherein the circuitry configured for detecting a personal mobile device identified by at least one device identifier within an effective range of at least one wireless transceiver associated with at least one healthcare administration space comprises:

circuitry configured for detecting the personal mobile device assigned to the patient and a second device assigned to a caregiver within a detection range of a stationary device known to be present in at least one healthcare administration space associated with at least one healthcare provider.

4. The healthcare information management system of claim 1, wherein the circuitry configured for causing a recordation of at least one indication of presence of the patient associated with the at least one patient identifier in the at least one healthcare administration space comprises:
  circuitry configured for updating a patient registry as an automatic response to the detection of the personal mobile device within the effective range of the at least one wireless transceiver associated with the at least one healthcare administration space.

5. The healthcare information management system of claim 1, further comprising:
  circuitry configured for determining whether presence of the patient in the at least one healthcare administration space constitutes an institutional readmission of the patient;
  circuitry configured for determining whether the institutional readmission indicates patient non-compliance with a health regimen; and
  circuitry configured for signaling a decision whether to transfer a resource to the patient based on the determination whether the patient is compliant with the health regimen.

6. The healthcare information management system of claim 1, further comprising:
  circuitry configured for determining whether presence of the patient in the at least one healthcare administration space constitutes an institutional readmission of the patient; and
  circuitry configured for transmitting a notification to a caregiver, via an interface in a vicinity of the patient, the notification based at least partly on an indication of an institutional readmission of the patient.

7. The healthcare information management system of claim 1, further comprising:
  circuitry configured for transmitting a notification to a caregiver responsive to an interface in a vicinity of the caregiver detecting a particular event relating to the caregiver.

8. The healthcare information management system of claim 1, wherein the circuitry configured for enabling the at least one medical equipment associated with the identified at least one protocol to function comprises:
  circuitry configured for preventing the at least one medical equipment from operating until an order for the identified at least one protocol is received and until an indication is received that the personal mobile device associated with the patient is detected within the effective range of the at least one wireless transceiver associated with the at least one healthcare administration space.

9. The healthcare information management system of claim 1, wherein the circuitry configured for detecting a personal mobile device identified by at least one device identifier within an effective range of at least one wireless transceiver associated with at least one healthcare administration space comprises:
  circuitry configured for detecting, via at least one radio frequency identification device (RFID), the at least one personal mobile device assigned to the patient having the particular condition within a detection range of at least one detection device.

10. The healthcare information management system of claim 1, wherein the circuitry configured for detecting a personal mobile device identified by at least one device identifier within an effective range of at least one wireless transceiver associated with at least one healthcare administration space comprises:
  circuitry configured for detecting a global positioning system (GPS)-based location of the personal mobile device assigned to the patient having the particular condition.

11. The healthcare information management system of claim 1, wherein the circuitry configured for detecting a personal mobile device identified by at least one device identifier within an effective range of at least one wireless transceiver associated with at least one healthcare administration space comprises:
  circuitry configured for detecting a presence of at least one wearable device assigned to the patient having the particular condition within a detection range of at least one detection device.

12. The healthcare information management system of claim 1, further comprising:
  circuitry configured for storing an indication of the at least one device identifier in at least one patient file in at least one database responsive to at least one patient intake input, and wherein the circuitry for associating a patient with at least one patient identifier, the patient associated with the personal mobile device identified by the at least one device identifier includes at least:
  circuitry configured for querying the at least one database to retrieve the at least one patient file as an automatic response to the detection of the personal mobile device within the effective range of the at least one wireless transceiver associated with the at least one healthcare administration space.

13. The healthcare information management system of claim 12, wherein the circuitry configured for storing an indication of the at least one device identifier in at least one patient file in at least one database responsive to at least one patient intake input comprises:
  circuitry configured for storing a mapping of an identifier associated with the personal mobile device to an identifier associated with the patient in at least one database responsive to the at least one patient intake input.

14. The healthcare information management system of claim 1, wherein the circuitry configured for causing a recordation of at least one indication of presence of the patient associated with the at least one patient identifier in the at least one healthcare administration space in at least one patient file indicating at least the patient having a particular condition comprises:
  circuitry configured for causing a recordation of a timestamp indicative of the personal mobile device in the at least one patient file.

15. The healthcare information management system of claim 1, further comprising:
  circuitry configured for determining whether an institutional readmission is indicative of patient noncompliance to a prior protocol; and
  circuitry configured for obtaining an indication of whether treating the particular condition with at least one new protocol has precedent, wherein the circuitry for enabling the at least one medical equipment associated with the identified at least one protocol to function includes at least:
  circuitry configured for enabling at least one machine associated with the at least one new protocol.

16. The healthcare information management system of claim 1, further comprising:

circuitry configured for associating at least one particular condition with at least one prior institutional admission; and circuitry configured for determining whether presence of the patient in the at least one healthcare administration space constitutes an institutional readmission of the patient based at least partly on the associating the at least one particular condition with at least one prior institutional admission.

17. The healthcare information management system of claim 1, further comprising:

circuitry configured for providing at least one notification including one or more prior protocols associated with the particular condition to at least one healthcare provider associated with the at least one wireless transceiver.

18. The healthcare information management system of claim 1, wherein the circuitry configured for detecting a personal mobile device identified by at least one device identifier within an effective range of at least one wireless transceiver associated with at least one healthcare administration space comprises:

circuitry configured for detecting at least one wireless-enabled mobile telephone within the effective range of the at least one wireless transceiver associated with the at least one healthcare administration space.

19. The healthcare information management system of claim 1, wherein the circuitry configured for detecting a personal mobile device identified by at least one device identifier within an effective range of at least one wireless transceiver associated with at least one healthcare administration space comprises:

circuitry configured for detecting the personal mobile device within an effective range of at least one wireless transceiver associated with at least one healthcare provider.

20. The healthcare information management system of claim 1, wherein the circuitry configured for detecting a personal mobile device identified by at least one device identifier within an effective range of at least one wireless transceiver associated with at least one healthcare administration space comprises:

circuitry configured for detecting the personal mobile device has established a wireless communication link with at least one wireless transceiver associated with at least one healthcare provider.

21. The healthcare information management system of claim 1, further comprising:

circuitry configured for determining, via the at least one patient file, whether the patient has previously been institutionally admitted for the particular condition a threshold number of times, wherein the circuitry for enabling the at least one medical equipment associated with the identified at least one protocol to function includes at least:

circuitry configured for causing at least one machine to dispense at least one reward only if the determination whether the patient has previously been institutionally admitted for the particular condition the threshold number of times indicates that the patient has previously been admitted a number of times less than the threshold number of times.

22. The system of claim 1, further comprising:

circuitry configured for determining whether presence of the patient in the at least one healthcare administration space constitutes an institutional readmission of the patient;

circuitry configured for determining whether the institutional readmission of the patient is indicative of patient non-compliance to a healthcare regimen; and circuitry configured for providing, to at least one paying party, at least one indication of patient non-compliance to the healthcare regimen based at least partly on the determination whether the institutional readmission of the patient is indicative of patient non-compliance to the healthcare regimen.

23. The system of claim 1, wherein the circuitry configured for detecting a personal mobile device identified by at least one device identifier within an effective range of at least one wireless transceiver associated with at least one healthcare administration space comprises:

circuitry configured for recognizing that the personal mobile device has previously been operably coupled with at least one wireless transceiver on at least one network associated with at least one healthcare provider via one or more files stored on a computer-readable medium of the personal mobile device.

24. The system of claim 1, wherein the circuitry configured for identifying at least one protocol associated with the patient and associated with the particular condition based at least partly on the at least one patient file associated with the patient comprises:

circuitry configured for associating the particular condition with at least one protocol, wherein the circuitry for enabling the at least one medical equipment associated with the identified at least one protocol to function includes at least:

circuitry configured for causing at least one machine to dispense at least one prescription associated with the at least one protocol including at least overriding the failsafe as an automatic response to the identification of the at least one protocol and the detection of the personal mobile device within the effective range of the at least one wireless transceiver associated with at least one healthcare administration space.

25. The system of claim 1, wherein the circuitry configured for enabling the at least one medical equipment associated with the identified at least one protocol to function includes at least:

circuitry configured for accessing at least one machine located in the patient's home via at least one network associated with at least one healthcare provider; and circuitry configured for causing the at least one machine to dispense at least one prescription associated with the at least one protocol including at least overriding the failsafe, wherein the causing the at least one machine to dispense the at least one prescription is an automatic response to (a) the recordation of the at least one indication of presence of the patient in the at least one healthcare administration space, (b) the identifying the at least one protocol, and (c) the accessing the at least one machine located in the patient's home via the at least one network associated with the at least one healthcare provider.

26. A healthcare information management system comprising:

means for detecting a personal mobile device identified by at least one device identifier within an effective range of at least one wireless transceiver associated with at least one healthcare administration space;

means for associating a patient with at least one patient identifier, the patient associated with the personal mobile device identified by the at least one device identifier;

means for causing a recordation of at least one indication of presence of the patient associated with the at least one patient identifier in the at least one healthcare administration space in at least one patient file indicating at least the patient having a particular condition, wherein the causing a recordation is an automatic response to the detection of the personal mobile device within the effective range of the at least one wireless transceiver associated with the at least one healthcare administration space;

means for identifying at least one protocol associated with the patient and associated with the particular condition based at least partly on the at least one patient file associated with the patient, the at least one protocol associated with at least one medical equipment located within the effective range of the at least one wireless transceiver associated with the at least one healthcare administration space, the at least one medical equipment implementing a failsafe that prevents the at least one medical equipment from operating until enabled; and means for enabling the at least one medical equipment associated with the identified at least one protocol to function including at least overriding the failsafe as an automatic response to the identification of the at least one protocol and the detection of the personal mobile device within the effective range of the at least one wireless transceiver associated with at least one healthcare administration space.

27. A healthcare information management method comprising:

detecting a personal mobile device identified by at least one device identifier within an effective range of at least one wireless transceiver associated with at least one healthcare administration space;

associating a patient with at least one patient identifier, the patient associated with the personal mobile device identified by the at least one device identifier;

causing a recordation of at least one indication of presence of the patient associated with the at least one patient identifier in the at least one healthcare administration space in at least one patient file indicating at least the patient having a particular condition, wherein the causing a recordation is an automatic response to the detection of the personal mobile device within the effective range of the at least one wireless transceiver associated with the at least one healthcare administration space;

identifying at least one protocol associated with the patient and associated with the particular condition based at least partly on the at least one patient file associated with the patient, the at least one protocol associated with at least one medical equipment located within the effective range of the at least one wireless transceiver associated with the at least one healthcare administration space, the at least one medical equipment implementing a failsafe that prevents the at least one medical equipment from operating until enabled; and enabling the at least one medical equipment associated with the identified at least one protocol to function including at least overriding the failsafe as an automatic response to the identification of the at least one protocol and the detection of the personal mobile device within the effective range of the at least one wireless transceiver associated with at least one healthcare administration space.

28. One or more physical media configured to bear a device-detectable implementation of a method including at least detecting a personal mobile device identified by at least one device identifier within an effective range of at least one wireless transceiver associated with at least one healthcare administration space;

querying a local registry stored on a non-transitory computer readable medium to associate particular patient identifier with the personal mobile device;

causing a recordation of at least one indication of presence of the patient associated with the at least one patient identifier in the at least one healthcare administration space in at least one patient file indicating at least the patient having a particular condition, wherein the causing a recordation is an automatic response to the detection of the personal mobile device within the effective range of the at least one wireless transceiver associated with the at least one healthcare administration space;

identifying at least one protocol associated with the patient and associated with the particular condition based at least partly on the at least one patient file associated with the patient, the at least one protocol associated with at least one medical equipment located within the effective range of the at least one wireless transceiver associated with the at least one healthcare administration space, the at least one medical equipment implementing a failsafe that prevents the at least one medical equipment from operating until enabled; and causing at least one machine to dispense at least one item associated with the identified at least one protocol to the particular patient based at least partly on the circuitry for causing the recordation of the patient presence in the at least one healthcare administration space and based at least partly on the circuitry for identifying the at least one protocol scheduled for the patient.

29. One or more physical media configured to bear a device-detectable implementation of a method including at least detecting a personal mobile device identified by at least one device identifier within an effective range of at least one wireless transceiver associated with at least one healthcare administration space;

associating a patient with at least one patient identifier, the patient associated with the personal mobile device identified by the at least one device identifier;

causing a recordation of at least one indication of presence of the patient associated with the at least one patient identifier in the at least one healthcare administration space in at least one patient file indicating at least the patient having a particular condition, wherein the causing a recordation is an automatic response to the detection of the personal mobile device within the effective range of the at least one wireless transceiver associated with the at least one healthcare administration space;

identifying at least one protocol associated with the patient and associated with the particular condition based at least partly on the at least one patient file associated with the patient, the at least one protocol associated with at least one medical equipment located within the effective range of the at least one wireless transceiver associated with the at least one healthcare administration space, the at least one medical equipment implementing a failsafe that prevents the at least one medical equipment from operating until enabled; and causing at least one machine to dispense at least one prescription associated with the identified at least one protocol to the particular patient based at least partly on the circuitry for causing the recordation of the patient presence in the at least one healthcare administration space and based at least partly on the circuitry for identifying the at least one protocol scheduled for the patient.

* * * * *